United States Patent [19]

Wehrli et al.

[11] Patent Number: 4,464,366
[45] Date of Patent: Aug. 7, 1984

[54] CEPHEM COMPOUNDS HAVING A TERMINAL AMINOCARBOXYLIC ACID GROUPING AND CONTAINING AN AZACYCLYL(THIO)UREIDO GROUP

[75] Inventors: Hansuli Wehrli, Reinach; Karoly Kocsis, Olsberg; Riccardo Scartazzini, Basel, all of Switzerland

[73] Assignee: Ciba Geigy Corporation, Ardsley, N.Y.

[21] Appl. No.: 214,155

[22] Filed: Dec. 8, 1980

[30] Foreign Application Priority Data

Dec. 19, 1979 [CH] Switzerland ............. 11283/79

[51] Int. Cl.$^3$ .................. C07D 501/36; A61K 31/545
[52] U.S. Cl. ...................................... 424/246; 544/21; 544/22; 544/27; 544/25; 544/28
[58] Field of Search ............. 544/21, 16, 26, 22, 544/27, 28, 30, 25; 424/246

[56] References Cited

U.S. PATENT DOCUMENTS

| | | | |
|---|---|---|---|
| 4,087,424 | 5/1978 | Saikawa et al. | 260/268 C |
| 4,112,090 | 9/1978 | Saikawa et al. | 424/251 |
| 4,219,554 | 8/1980 | Saikawa et al. | 424/250 |
| 4,223,037 | 9/1980 | Preiss et al. | 544/22 |
| 4,338,438 | 7/1982 | Christensen et al. | 544/21 |

FOREIGN PATENT DOCUMENTS 0000500 7/1979 European Pat. Off.
0015240 3/1980 European Pat. Off.

*Primary Examiner*—Nicholas S. Rizzo
*Attorney, Agent, or Firm*—Joseph G. Kolodny

[57] ABSTRACT

Compounds of the formula

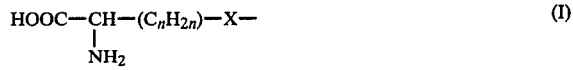

HOOC—CH—($C_nH_{2n}$)—X—   (I)
         |
         $NH_2$

-continued

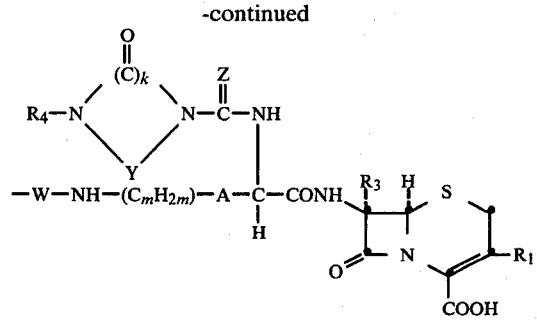

in which
the index n represents an integer of from 1 to 4,
the index m represents 0 or 1,
X represents oxygen, sulphur or the group —NH—,
W represents a group —CO—, —CO—NHSO$_2$— or —SO$_2$NH—CO—,
or X-W together represent a group —CO— or —CO—NHSO$_2$—,
A represents optionally substituted phenylene, thienylene or furylene,
Z represents oxygen or sulphur,
Y represents lower alkylene,
the index k represents the value 1 or 2,
R$_4$ represents hydrogen, an optionally substituted lower aliphatic or cycloaliphatic radical or acyl,
R$_1$ represents hydrogen, lower alkyl, lower alkoxy, halogen or a group of the formula —CH$_2$—R$_2$ in which R$_2$ represents a free, esterified or etherified hydroxy or mercapto group or a quaternary ammonium group, and
R$_3$ represents hydrogen or methoxy, and in which the carboxyl groups are optionally esterified in a form that can be split under physiological conditions, and salts of such compounds having salt-forming groups, are obtained by liberating the functional group(s) in a compound of the formula I in which at least one of the functional groups present is protected.

The compounds are effective in vitro and in vivo against gram-positive and gram-negative bacteria and cocci.

18 Claims, No Drawings

CEPHEM COMPOUNDS HAVING A TERMINAL AMINOCARBOXYLIC ACID GROUPING AND CONTAINING AN AZACYCLYL(THIO)UREIDO GROUP

The invention relates to novel acylamino-3-cephem-4-carboxylic acid compounds and their salts, processes for their manufacture, pharmaceutical agents containing these compounds and having antibiotic activity and their therapeutic use for the treatment of infections, and also new intermediates and their manufacture.

Numerous 7β-acylamino-3-cephem-4-carboxylic acid compounds are already known that differ from one another by the substituents in the 3-position of the 3-cephem structure and by the acyl group at the 7β-amino group. Surveys have been published on such compounds, processes for their manufacture and on their antibiotic activities by, for example, Edwin H. Flynn, Cephalosporins and Penicillins, Academic Press, New York and London, 1972; J. Cs. Jászberény and T. E. Gunda, Progr. Med. Chem., vol. 12, 1975, pp. 395–477, and Peter G. Sammes, Chemical Reviews, 1976, vol. 76, No. 1, pp. 113-155.

The appearance of new pathogenic germs that have developed a resistance to the antibiotics used hitherto, and the known allergic response to these antibiotics, create the need for new active compounds that do not have the mentioned disadvantages or have them only to a slight extent.

The problem underlying the present invention is to manufacture novel 7β-acylamino-3-cephem-4-carboxylic acid compounds having novel acyl groups that are characterised by the presence of a terminal α-aminocarboxylic acid grouping and an azacyclyl(thio)ureido group. The novel compounds are distinguished by a wide range of action against normal and resistant germs, especially against Pseudomonas.

The present invention relates also to the corresponding carboxylic acids and their reactive functional derivatives, in which functional groups are optionally protected, which are to be used as starting materials and contain the novel acyl groups and to processes for their manufacture.

The invention relates especially to acylamino-3-cephem-4-carboxylic acid compounds of the formula

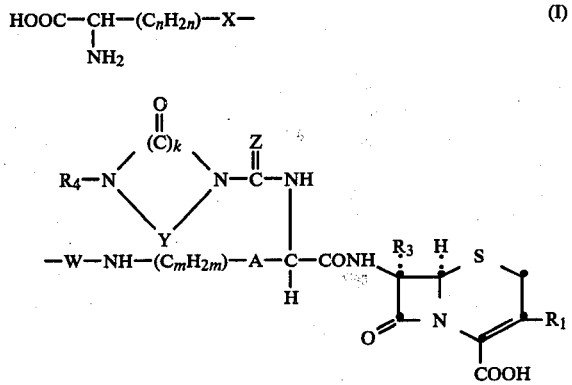

in which
the index n represents an integer of from 1 to 4,
the index m represents 0 or 1,
X represents oxygen, sulphur or the group —NH—,
W represents a group —CO—, —CO—NHSO$_2$— or —SO$_2$NH—CO—,
or X—W together represent a group —CO— or —CO—NHSO$_2$—,
A represents optionally substituted phenylene, thienylene or furylene,
Z represents oxygen or sulphur,
Y represents lower alkylene,
the index k represents the value 1 or 2,
R$_4$ represents hydrogen, an optionally substituted lower aliphatic or cycloaliphatic radical or acyl,
R$_1$ represents hydrogen, lower alkyl, lower alkoxy, halogen or a group of the formula —CH$_2$—R$_2$ in which R$_2$ represents a free, esterified or etherified hydroxy or mercapto group or a quaternary ammonium group, and
R$_3$ represents hydrogen or methoxy,
and in which functional groups are optionally in protected form, salts of such compounds having acidic and/or basic groups, processes for the manufacture of these compounds, pharmaceutical agents containing such substances and their therapeutic use.

In this description of the invention, the term "lower" in groups such as lower alkyl, lower alkylene, lower alkoxy, lower alkanoyl and the like means that the corresponding groups contain up to 7, but preferably up to 4, carbon atoms unless expressly defined otherwise.

A group —(C$_n$H$_{2n}$)— is a branched or unbranched alkylene chain and is especially methylene, 1,2-ethylene, 1,3-propylene or 1,4-butylene, but also, for example, 1,1-ethylene, 1,1-propylene, 1,2-propylene, 1,1-butylene or 1,1-isobutylene.

An optionally substituted phenylene group A is especially p-phenylene but may alternatively be o- or m-phenylene. Substituents of the phenylene group are, for example, lower alkyl, such as methyl, hydroxy, lower alkoxy, such as methoxy, and/or halogen, such as fluorine, chlorine or bromine.

An optionally substituted thienylene group A is especially 2,5-thienylene, but also 2,4- or 2,3-thienylene.

An optionally substituted furylene group A is especially 2,5-furylene, but also 2,4- or 2,3-furylene.

Substituents of the thienylene and furylene group A are, for example, lower alkyl, such as methyl, lower alkoxy, such as methoxy, and/or halogen, such as fluorine, chlorine or bromine.

The lower alkylene radical Y is optionally branched and linked by adjacent carbon atoms to the two ring nitrogen atoms. Y may contain from 2 to 7 carbon atoms and may be, for example, a correspondingly linked heptylene, for example 1,2- or 2,3-heptylene, but is preferably a corresponding radical having from 2 to 4 carbon atoms, for example 1,2- or 2,3-butylene, and especially 1,2-ethylene.

A lower aliphatic radical R$_4$ is lower alkyl, lower alkenyl or lower alkynyl.

A lower alkyl radical R$_4$ is especially a radical having from 1 to 4 carbon atoms, such as methyl, isopropyl or isobutyl and especially ethyl.

As lower alkenyl, R$_4$ has preferably from 2 to 5 carbon atoms and the double bond starts preferably from the linking carbon atom (1-position). Examples of such radicals are vinyl, propenyl, and especially 1-isobutenyl.

As lower alkynyl, R$_4$ has preferably from 2 to 4 carbon atoms and is especially ethynyl or 1-propynyl.

A cycloaliphatic radical R$_4$ is cycloalkyl having from 3 to 8, preferably from 3 to 6, carbon atoms, and is especially cyclopropyl, cyclobutyl, cyclopentyl or cyclohexyl.

Substituents of the above-mentioned radicals $R_4$, especially of a corresponding lower alkyl, are hydroxy, lower alkanoyloxy, lower alkoxycarbonyloxy, lower alkoxy, lower alkylthio, halogen, especially chlorine or bromine, optionally functionally modified carboxy and optionally lower alkylated amino, such as di-lower alkylated amino. Preferred substituents are hydroxy and lower alkoxy which are attached preferably at the linking carbon atom (i.e. in the 1-position). Examples of substituted radicals of this type are 1-hydroxyethyl, methoxymethyl, 1-methoxyethyl, 2-methoxyethyl, 4-methoxybutyl and especially 1-hydroxyisobutyl.

An acyl radical $R_4$ is an acyl radical derived from a carboxylic acid having up to 12 carbon atoms, from a semi-ester of carbonic or thiocarbonic acid, from an aromatic or lower aliphatic sulphonic acid or from an optionally N-substituted semi-amide of carbonic, thiocarbonic, iminocarbonic or sulphuric acid.

A carboxylic acid radical $R_4$ is especially an aromatic radical, such as a naphthoic or benzoic acid radical optionally substituted by halogen, for example chlorine, lower alkyl, hydroxy, lower alkoxy, di-lower alkylamino, for example dimethylamino, lower alkylsulphonylamino, for example mesylamino, lower alkanoylamino, for example acetamido, amino or nitro; a heterocyclic carboxylic acid radical optionally substituted by lower alkyl or halogen, for example chlorine, such as a corresponding pyridine-, thiophene-, furan- or pyrrole-carboxylic acid radical; or especially a lower aliphatic carboxylic acid radical optionally substituted by halogen, for example chlorine, lower alkoxy, lower alkanoyloxy, cyano or phenoxy, such as corresponding lower alkanoyl, for example corresponding acetyl. A carbonic or thiocarbonic acid semiester radical $R_4$ is, for example, lower alkoxycarbonyl, for example ethoxycarbonyl, aryl-lower alkoxycarbonyl, for example benzyloxycarbonyl, cycloalkoxycarbonyl, for example cyclohexyloxycarbonyl, or aryloxycarbonyl, for example phenoxycarbonyl, or corresponding-thiocarbonyl.

An acyl radical $R_4$ derived from an aromatic sulphonic acid is 1- or 2-naphthalenesulphonyl, or benzenesulphonyl optionally substituted by halogen, for example chlorine, or by lower alkyl, for example benzenesulphonyl, chlorobenzenesulphonyl, for example o-chlorobenzenesulphonyl, or tosyl, for example p-tosyl. An acyl radical $R_4$ derived from a lower aliphatic sulphonic acid is especially lower alkylsulphonyl, for example mesyl.

An acyl radical derived from an optionally N-substituted, such as N-lower alkylated, semi-amide of carbonic, thiocarbonic, iminocarbonic or sulphuric acid is especially a carbamoyl, thiocarbamoyl, iminocarbamoyl or sulphamoyl each optionally mono- or di-substituted at the nitrogen atom by lower alkyl, halo-lower alkyl, for example chloro-lower alkyl, or lower alkoxy-lower alkyl, for example methoxyethyl or ethoxyethyl.

A lower alkyl group $R_1$ contains from 1 to 4 carbon atoms and is, for example, ethyl, propyl, butyl or especially methyl.

A lower alkoxy group $R_1$ contains from 1 to 4 carbon atoms and is, for example, methoxy, ethoxy, propoxy or butoxy.

$R_1$ as halogen is fluorine, bromine, iodine or preferably chlorine.

An esterified hydroxy or mercapto group $R_2$ is esterified by a lower aliphatic carboxylic acid or by an optionally N-substituted carbamic acid.

Hydroxy groups $R_2$ esterified by lower aliphatic carboxylic acids are especially lower alkanoyloxy, especially acetoxy, but also formyloxy, propionyloxy, valeryloxy, hexanoyloxy, heptanoyloxy or pivaloyloxy.

Mercapto groups $R_2$ esterified by lower aliphatic carboxylic acids are lower alkanoylthio, such as acetylthio, formylthio, propionylthio, valeroylthio, hexanoylthio, heptanoylthio or pivaloylthio.

In a hydroxy or mercapto group $R_2$ esterified by an optionally N-substituted carbamic acid, N-substituents are lower alkyl optionally substituted by halogen, for example chlorine, or by lower alkanoyloxy, for example acetoxy or propionyloxy, for example methyl, ethyl, 2-chloroethyl or 2-acetoxyethyl. Hydroxy groups $R_2$ esterified in this manner are, for example, carbamoyloxy, N-methylcarbamoyloxy, N-ethylcarbamoyloxy, N-(2-chloroethyl)-carbamoyloxy or N-(2-acetoxyethyl)-carbamoyloxy. Corresponding esterified mercapto groups $R_2$ are, for example, carbamoylthio, N-methylcarbamoylthio, N-ethylcarbamoylthio, N-(2-chloroethyl)-carbamoylthio or N-(2-acetoxyethyl)-carbamoylthio.

Etherified hydroxy and mercapto groups $R_2$ are etherified by, for example, an aliphatic hydrocarbon radical and are especially lower alkoxy, especially having from 1 to 4 carbon atoms, especially methoxy, but also ethoxy, n-propoxy or isopropoxy, and also straight-chain or branched butoxy, or lower alkylthio, preferably having from 1 to 4 carbon atoms, especially methylthio, but also ethylthio, n-propylthio or isopropylthio, and also straight-chain or branched butylthio.

Etherified mercapto groups $R_2$ are etherified especially by an optionally substituted heterocyclic radical linked by a ring carbon atom to the mercapto group and having from 1 to 4 ring nitrogen atoms and optionally one further ring hetero atom selected from the group oxygen and sulphur.

Such heterocyclic radicals are especially monocyclic, five-membered and six-membered diazacyclic, triazacyclic, tetrazacyclic, thiazacyclic, thiadiazacyclic, thiatriazacyclic, oxazacyclic or oxadiazacyclic radicals of aromatic character optionally substituted, for example by the substituents mentioned below.

Substituents of such heterocyclyl radicals are, inter alia, lower alkyl, especially methyl, but also ethyl, n-propyl, isopropyl or straight-chain or branched butyl; or lower alkyl substituted by hydroxy, esterified hydroxy, such as lower alkanoyloxy, halogen, such as chlorine, carboxy, esterified carboxy, such as lower alkoxycarbonyl, sulpho, amidated sulpho, amino, mono- or di-lower alkylamino, or acylamino, such as lower alkanoylamino or lower alkanoylamino substituted, for example, by carboxy or halogen, for example 2-hydroxyethyl, 2-acetoxyethyl, 2-chloroethyl, carboxymethyl, 2-carboxyethyl, ethoxycarbonylmethyl, 2-ethoxycarbonylethyl, sulphomethyl, 2-sulphoethyl, sulphamoylmethyl, 2-sulphamoylethyl, 2-aminoethyl, 2-dimethylaminoethyl or 2-acetylaminoethyl. Further substituents of the heterocyclic radical are cycloalkyl, for example cyclopentyl or cyclohexyl; aryl, such as phenyl optionally substituted by halogen, for example chlorine, or by nitro; aryl-lower alkyl, for example benzyl; or heterocyclyl, such as furyl, for example 2-furyl, thienyl, for example 2-thienyl, or oxazolyl, for example 2- or 5-oxazolyl; or functional groups; such as halogen, for example, fluorine, chlorine or bromine; optionally substituted amino, such as amino optionally mono- or di-substituted by lower alkyl, for example amino, methylamino or dimethylamino; acylamino, such as lower alkanoylamino, or lower alkanoylamino substituted by halogen or carboxy, such as acetylamino, 3-chloropropionylamino or 3-carboxypropionylamino; nitro; hydroxy; lower alkoxy, for example methoxy, ethoxy, n-butoxy or 2-ethylhexyloxy; or optionally functionally modified carboxy, such as carboxy, esterified carboxy, such as lower alkoxycarbonyl, for example methoxycarbonyl or ethoxycarbonyl, optionally substituted carbamoyl, such as N-mono- or N,N-di-lower alkylated carbamoyl, for example N-methylcarbamoyl or N,N-dimethylcarbamoyl, or cyano, and also oxo or oxido, it being possible for one or more such substituents, which are bonded especially to ring carbon atoms but alternatively, especially in the case of lower alkyl and oxido, to ring nitrogen atoms, to be present.

Preferred heterocyclically etherified mercapto groups $R_2$ in which the heterocyclic radical represents a corresponding monocyclic, five-membered radical are, inter alia, imidazolylthio, for example 2-imidazolylthio; triazolylthio optionally substituted by lower alkyl and/or phenyl, for example 1H-1,2,3-triazol-4-ylthio, 1-methyl-1H-1,2,3-triazol-4-ylthio, 1H-1,2,4-triazol-3-ylthio, 5-methyl-1H-1,2,4-triazol-3-ylthio, 3-methyl-1-phenyl-1H-1,2,4-triazol-5-ylthio, 4,5-dimethyl-4H-1,2,4-triazol-3-ylthio or 4-phenyl-4H-1,2,4-triazol-3-ylthio; especially tetrazolylthio optionally substituted as indicated, for example 1H-tetrazol-5-ylthio, 1-methyl-1H-tetrazol-5-ylthio, 1-carboxymethyl-1H-tetrazol-5-ylthio, 1-(2-carboxyethyl)-1H-tetrazol-5-ylthio, 1-sulphomethyl-1H-tetrazol-5-ylthio, 1-(2-sulphoethyl)-1H-tetrazol-5-ylthio, 1-(2-dimethylaminoethyl)-1H-tetrazol-5-ylthio, 1-phenyl-1H-tetrazol-5-ylthio or 1-(4-chlorophenyl)-1H-tetrazol-5-ylthio; thiazolylthio or isothiazolylthio optionally substituted by lower alkyl or thienyl, for example 2-thiazolylthio, 4-(2-thienyl)-2-thiazolylthio, 4,5-dimethyl-2-thiazolylthio, 3-isothiazolylthio, 4-isothiazolylthio or 5-isothiazolylthio; especially also thiadiazolylthio optionally substituted as indicated, for example 1,2,3-thiadiazol-4-ylthio, 1,2,3-thiadiazol-5-ylthio, 1,3,4-thiadiazol-2-ylthio, 2-methyl-1,3,4-thiadiazol-5-ylthio, 2-(3-carboxypropionylamino)-1,3,4-thiadiazol-5-ylthio, 1,2,4-thiadiazol-5-ylthio or 1,2,5-thiadiazol-3-ylthio; thiatriazolylthio, for example 1,2,3,4-thiatriazol-5-ylthio; oxazolylthio or isoxazolylthio optionally substituted as indicated, for example 5-oxazolylthio, 4-methyl-5-oxazolylthio, 2-oxazolylthio, 4,5-diphenyl-2-oxazolylthio or 3-methyl-5-isoxazolylthio; or oxadiazolylthio optionally substituted as indicated, for example 1,2,4-oxadiazol-5-ylthio, 2-methyl-1,3,4-oxadiazol-5-ylthio, 2-phenyl-1,3,4-oxadiazol-5-ylthio, 5-(4-nitrophenyl)-1,3,4-oxadiazol-2-ylthio or 2-(2-thienyl)-1,3,4-oxadiazol-5-ylthio.

Preferred heterocyclically etherified mercapto groups $R_2$ in which the heterocyclic radical represents a corresponding monocyclic, six-membered radical or a corresponding partially saturated radical contain especially from 1 to 3 nitrogen atoms and are, for example, 1-oxidopyridylthio optionally substituted by halogen, for example 1-oxido-2-pyridylthio or 4-chloro-1-oxido-2-pyridylthio; pyridazinylthio optionally substituted by hydroxy, for example 3-hydroxy-6-pyridazinylthio; N-oxidopyridazinylthio optionally substituted by lower alkyl, lower alkoxy or halogen, for example 2-oxido-6-pyridazinylthio, 3-chloro-1-oxido-6-pyridazinylthio, 3-methyl-2-oxido-6-pyridazinylthio, 3-methoxy-1-oxido-6-pyridazinylthio, 3-ethoxy-1-oxido-6-pyridazinylthio, 3-n-butoxy-1-oxido-6-pyridazinylthio or 3-(2-ethylhexyloxy)-1-oxido-6-pyridazinylthio; 2-oxo-1,2-dihydropyrimidinylthio optionally substituted by lower alkyl, amino, di-lower alkylamino or carboxy, for example 2-oxo-1,2-dihydro-4-pyridmidinylthio, 5- or 6-methyl-2-oxo-1,2-dihydro-4-pyrimidinylthio, 1-amino- or 6-amino-2-oxo-1,2-dihydro-4-pyrimidinylthio, 6-dimethylamino-2-oxo-1,2-dihydro-4-pyrimidinylthio, 5-carboxy-2-oxo-1,2-dihydro-4-pyrimidinylthio or 6-carboxy-2-oxo-1,2-dihydro-4-pyrimidinylthio; or non-aromatic triazinyl optionally substituted by lower alkyl, for example methyl, carboxy-lower alkyl, for example carboxymethyl, sulpho-lower alkyl, for example sulphomethyl, or oxo, especially 5,6-dioxotetrahydro-as-triazinyl optionally substituted as indicated, for example 1- or 2-methyl-5,6-dioxo-1,2,5,6-tetrahydro-as-triazin-3-yl, 4-methyl-5,6-dioxo-1,4,5,6-tetrahydro-as-triazin-3-yl, 1- or 2-carboxymethyl-5,6-dioxo-1,2,5,6-tetrahydro-as-triazin-3-yl, 4-carboxymethyl-5,6-dioxo-1,4,5,6-tetrahydro-as-triazin-3-yl, 1- or 2-sulphomethyl-5,6-dioxo-1,2,5,6-tetrahydro-as-triazin-3-yl or 4-sulphomethyl-5,6-dioxo-1,4,5,6-tetrahydro-as-triazin-3-yl.

Quaternary ammonium groups $R_2$ are quaternary ammonium groups derived from tertiary organic bases, preferably from corresponding aliphatic amines or especially from corresponding heterocyclic nitrogen bases, and linked by the nitrogen atom to the methyl carbon atom.

In a quaternary ammonium group $R_2$, which is derived from a tertiary organic base, the nitrogen atom is bonded to the methylene carbon atom and is accordingly present in quaternised, positively charged form. Quaternary ammonium groups are, inter alia, tri-lower alkylammonium, for example trimethylammonium, triethylammonium, tripropylammonium or tributylammonium; but especially monocyclic or bicyclic azacyclic ammonium groups of aromatic character having 1 or 2 ring nitrogen atoms and optionally one ring sulphur atom, such as pyrimidinium, pyridazinium, thiazolium, quinolinium and especially pyridinium, and being optionally substituted, for example mono- or poly-substituted by lower alkyl, such as methyl; hydroxy-lower alkyl, such as hydroxymethyl; amino; substituted sulphonamido, such as 4-aminophenylsulphonamido; hydroxy; halogen, such as fluorine, chlorine, bromine or iodine; halo-lower alkyl, such as trifluoromethyl; sulpho; optionally functionally modified carboxy, such as carboxy, lower alkoxycarbonyl, for example methoxycarbonyl, cyano, carbamoyl optionally N-mono- or N,N-di-substituted by lower alkyl, for example methyl or ethyl, or by hydroxy-lower alkyl, for example hydroxymethyl, for example carbamoyl, N-methylcarbamoyl or N,N-dimethylcarbamoyl, hydrazinocarbonyl optionally N-substituted by lower alkyl, for example hydrazinocarbonyl; carboxylower alkyl, such as carboxymethyl; lower alkanoyl, such as acetyl; or by 1-lower alkylpyrrolidinyl, such as 1-methyl-2-pyrrolidinyl.

Heterocyclic ammonium groups $R_2$ are especially pyridinium optionally containing lower alkyl, hydroxy-lower alkyl, amino, substituted sulphonamido, hydroxy, halogen, trifluoromethyl, sulpho, carboxy, lower alkoxycarbonyl, cyano, lower alkanoyl, 1-lower alkylpyrrolidinyl or carbamoyl optionally N-substituted by lower alkyl or by hydroxy-lower alkyl, for example pyridinium, 2-, 3- or 4-methylpyridinium, 3,5-dimethylpyridinium, 2,4,6-trimethylpyridinium, 2-, 3- or 4-ethylpyridinium, 2-, 3- or 4-propylpyridinium or especially 4-hydroxymethylpyridinium, also 2-amino- or 2-amino- 6-methyl-pyridinium, 2-(4-aminophenylsulphonylamido)-pyridinium, 3-hydroxypyridinium, 3-fluoro-, 3-chloro-, 3-iodo- or especially 3-bromo-pyridinium, β-trifluoromethylpyridinium, 3-sulphopyridinium, 2-, 3- or 4-carboxy- or 2,3- or 3,4-dicarboxy-pyridinium, 4-methoxycarbonylpyridinium, 3- or 4-cyanopyridinium, 3-carboxymethylpyridinium, 3- or 4-acetylpyridinium, 3-(1-methyl-2-pyrrolidinyl)-pyridinium, and especially 4-carbamoyl-, 3-carbamoyl-, 3,4-dicarbamoyl-, 3- or 4-N-methylcarbamoyl-, 4-N,N-dimethylcarbamoyl-, 4-N-ethylcarbamoyl-, 3-N,N-diethylcarbamoyl-, 4-N-propylcarbamoyl-, 4-isopropylcarbamoyl- and 4-hydroxymethylcarbamoyl-pyridinium.

The functional groups present in compounds of the formula I, especially carboxyl and amino groups, but also hydroxy and sulpho groups, are optionally protected by protecting groups that are used in penicillin, cephalosporin and peptide chemistry.

Such protecting groups can be split off readily, i.e. without undesired side reactions taking place, for example by solvolysis, reduction, photolysis or alternatively under physiological conditions.

Protecting groups of this type and also the manner in which they are split off are described, for example, in "Protective Groups in Oranic Chemistry", Plenum Press, London, New York, 1973, in "The Peptides", vol. I, Schröder and Lubke, Academic Press, London, New York, 1965, and in "Methoden der organischen Chemie", Houben-Weyl, 4th edition, vol. 15/1, Georg Thieme Verlag, Stuttgart, 1974.

Thus, carboxyl groups, such as the 4-carboxyl group, are protected, for example, usually in esterified form, such ester groupings being readily splittable under mild conditions. Carboxyl groups protected in this manner contain as esterifying groups especially lower alkyl groups branched in the 1-position or suitably substituted in the 1- or 2-position. Preferred carboxyl groups present in esterified form are, inter alia, tert.-lower alkoxycarbonyl, for example tert.-butoxycarbonyl; arylmethoxycarbonyl having one or two aryl radicals, these representing phenyl radicals optionally mono- or polysubstituted, for example by lower alkyl, such as tert.-lower alkyl, for example tert.-butyl, lower alkoxy, such as methoxy, hydroxy, halogen, for example chlorine, and/or by nitro, such as benzyloxycarbonyl optionally substituted, for example as indicated above, for example 4-nitrobenzyloxycarbonyl or 4-methoxybenzyloxycarbonyl, or diphenylmethoxycarbonyl optionally substituted, for example as indicated above, for example diphenylmethoxycarbonyl or di-(4-methoxyphenyl)-methoxycarbonyl; 1-lower alkoxy-lower alkoxycarbonyl, such as methoxymethoxycarbonyl, 1-methoxyethoxycarbonyl or 1-ethoxymethoxycarbonyl; 1-lower alkylthio-lower alkoxycarbonyl, such as 1-methylthiomethoxycarbonyl or 1-ethylthioethoxycarbonyl; aroylmethoxycarbonyl in which the aroyl group represents benzoyl optionally substituted, for example by halogen, such as bromine, for example phenacyloxycarbonyl; 2-halo-lower alkoxycarbonyl, for example 2,2,2-trichloroethoxycarbonyl, 2-bromoethoxycarbonyl or 2-iodoethoxycarbonyl; or 2-(tri-substituted silyl)-ethoxycarbonyl, in which each of the substituents, independently of one another, represents an aliphatic, araliphatic, cycloaliphatic or aromatic hydrocarbon radical optionally substituted, for example by lower alkyl, lower alkoxy, aryl, halogen and/or by nitro and having, for example, up to 15 carbon atoms, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further protected carboxyl groups present in esterified form are corresponding silyloxycarbonyl groups, especially organic silyloxycarbonyl groups, and also corresponding stannyloxycarbonyl groups. In these groups, the silicon or tin atom preferably contains as substituents lower alkyl, especially methyl, but also lower alkoxy, for example methoxy, and/or halogen, for example chlorine. Suitable silyl or stannyl protecting groups are especially tri-lower alkylsilyl, especially trimethylsilyl, but also dimethyl-tert.-butyl-silyl, lower alkoxy-lower alkyl-halo-silyl, for example methoxymethyl-chloro-silyl or di-lower alkyl-halosilyl, for example dimethyl-chloro-silyl, or correspondingly substituted stannyl compounds, for example tri-n-butylstannyl.

Preferred protected carboxyl groups are tert.-lower alkoxycarbonyl, such as tert.-butoxycarbonyl, and especially benzyloxycarbonyl optionally substituted, for example as indicated above, such as 4-nitrobenzyloxycarbonyl, or diphenylmethoxycarbonyl.

An esterified carboxyl group that can be split under physiological conditions is especially an acyloxymethoxycarbonyl group in which acyl represents, for example, the radical of an organic carboxylic acid, especially of an optionally substituted lower alkane-carboxylic acid, or in which acyloxymethyl forms the radical or a lactone. Such groups are lower alkanoyloxymethoxycarbonyl, for example acetoxymethoxycarbonyl or pivaloyloxymethoxycarbonyl, amino-lower alkanoylmethoxycarbonyl, especially α-amino-lower alkanoyloxymethoxycarbonyl, for example glycyloxymethoxycarbonyl, L-valyloxymethoxycarbonyl or L-leucyloxymethoxycarbonyl, and also phthalidyloxycarbonyl, for example 2-phthalidyloxycarbonyl, or indanyloxycarbonyl, for example 5-indanyloxycarbonyl.

A protected amino group may be present, for example, in the form of a readily splittable acylamino, arylmethylamino, etherified mercaptoamino, 2-acyl-lower alk-1-en-1-ylamino, silylamino or stannylamino group or in the form of an azido group.

In a corresponding acylamino group, acyl is, for example, the acyl radical of an organic carboxylic acid having, for example, up to 18 carbon atoms, especially of an alkanecarboxylic acid optionally substituted, for example by halogen or aryl, or of a benzoic acid optionally substituted, for example by halogen, lower alkoxy or nitro, or of a carbonic acid semi-ester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl optionally substituted, for example by halogen, lower alkoxy or nitro, for example benzoyl, 4-chlorobenzoyl, 4-methoxybenzoyl or 4-nitrobenzoyl, or lower alkoxycarbonyl branched in the 1-position of the lower alkyl radical or suitably substituted in the 1- or 2-position, especially tert.-lower alkoxycarbonyl, for example tert.-butoxycarbonyl, arylmethoxycarbonyl having one or two aryl radicals that preferably represent phenyl optionally mono- or poly-substituted, for example by lower alkyl, especially tert.-lower alkyl, such as tert.-butyl, lower alkoxy, such as methoxy, hydroxy, halogen, for example chlorine, and/or by nitro, such as optionally substituted benzyloxycarbonyl, for example 4-nitrobenzyloxycarbonyl, or substituted diphenylmethoxycarbonyl, for example benzhydryloxycarbonyl or di-(4-methoxyphenyl)-methoxycarbonyl, aroylmethoxycarbonyl in which the aroyl group preferably represents benzoyl optionally substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl, in which each of the substituents, independently of one another, represents an aliphatic, araliphatic, cycloaliphatic or aromatic hydrocarbon radical optionally substituted, for example by lower alkyl, lower alkoxy, aryl, halogen or nitro, and having, for example, up to 15 carbon atoms, such as corresponding optionally substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Further acyl radicals suitable as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, optionally substituted diphenylphosphoryl, for example diphenylphosphoryl, diphenyl-lower alkylphosphoryl optionally substituted, for example by nitro, for example dibenzylphosphoryl or di-4-nitrobenzylphosphoryl, optionally substituted phenoxy-phenyl-phosphonyl, for example phenoxy-phenyl-phosphonyl, di-lower alkylphosphinyl, for example diethylphosphinyl, or optionally substituted diphenylphosphinyl, for example diphenylphosphinyl.

In an arylmethylamino group that represents a mono-, di- or especially tri-arylmethylamino, the aryl radicals are especially optionally substituted phenyl radicals. Such groups are, for example, benzylamino, diphenylmethylamino and especially tritylamino.

An etherified mercapto group in an amino group protected by such a radical is especially arylthio or aryl-lower alkylthio in which aryl is especially phenyl optionally substituted, for example by lower alkyl, such as methyl or tert.-butyl, lower alkoxy, such as methoxy, halogen, such as chlorine, and/or nitro. A corresponding amino-protecting group is, for example, 4-nitrophenylthio.

In a 2-acyl-lower alk-1-en-1-yl radical that may be used as an amino-protecting group, acyl is, for example, the corresponding radical of a lower alkanecarboxylic acid, of a benzoic acid optionally substituted, for example by lower alkyl, such as methyl or tert.-butyl, lower alkoxy, such as methoxy, halogen, such as chlorine, and/or nitro, or especially of a carbonic acid semi-ester, such as a carbonic acid lower alkyl semi-ester. Corresponding protecting groups are especially 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

A silylamino or stannylamino group is especially an organic silylamino or stannylamino group in which the silicon or tin atom contains as substituents preferably lower alkyl, especially methyl, but also lower alkoxy, for example methoxy, and/or halogen, for example chlorine. Corresponding silyl or stannyl groups are especially tri-lower alkylsilyl, especially trimethylsilyl, but also dimethyl-tert.-butyl-silyl, lower alkoxy-lower alkyl-halo-silyl, for example methoxy-methyl-chloro-silyl, or di-lower alkyl-halo-silyl, for example dimethyl-chloro-silyl, or correspondingly substituted stannyl, for example tri-n-butylstannyl.

An amino group many also be protected in protonated form; corresponding anions that come into consideration are especially those of strong inorganic acids, such as hydrohalic acids, for example the chlorine or bromine anion, or of organic sulphonic acids, such as p-toluenesulphonic acid.

Preferred amino-protecting groups are acyl radicals of carbonic acid semi-esters, especially tert.-butoxycarbonyl, benzyloxycarbonyl optionally substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl, and also trityl or formyl.

Hyroxy-protecting groups are, for example, acyl radicals, such as lower alkanoyl optionally substituted, for example by halogen, such as 2,2-dichloroacetyl, or especially the acyl radicals of carbonic acid semi-esters mentioned in connection with a protected amino group, especially 2,2,2-trichloroethoxycarbonyl, or organic silyl or stannyl radicals, also etherifying groups that can readily be split off, such as tert.-lower alkyl, for example tert.-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, 1-methylthiomethyl, 1-methylthioethyl or 1-ethylthioethyl, or 2-oxa- or 2-thia-cycloalkyl having from 5 to 7 ring atoms, for example 2-tetrahydrofuryl or 2-tetrahydropyranyl or corresponding thia analogues, and also optionally substituted 1-phenyl-lower alkyl, such as optionally substituted benzyl or diphenylmethyl, suitable substituents of the phenyl radicals being, for example, halogen, such as chlorine, lower alkoxy, such as methoxy, and/or nitro.

A protected sulpho group is especially an esterified sulpho group, such as a sulpho group esterified by an aliphatic, cycloaliphatic, cycloaliphatic-aliphatic, aromatic or araliphatic alcohol, for example a lower alkanol, or by a silyl or stannyl radical, such as tri-lower alkylsilyl. In a sulpho group, the hydroxy group may be etherified, for example in the same manner as the hydroxy group in an esterified carboxy group.

Salts of compounds according to the invention are especially pharmaceutically acceptable non-toxic salts, such as those of compounds of the formula I having acid groups, for example having free carboxyl and sulpho groups. Such salts are especially metal or ammonium salts, such as alkali metal and alkaline earth metal salts, for example sodium, potassium, magnesium or calcium salts, and also ammonium salts with ammonia or suitable organic amines, aliphatic, cycloaliphatic, cycloaliphatic-aliphatic or araliphatic primary, secondary or tertiary mono-, di- or poly-amines and also heterocyclic bases being especially suitable for salt formation, such as lower alkylamines, for example triethylamine, hydroxy-lower alkylamines, for example 2-hydroxyethylamine, bis-(2-hydroxyethyl)-amino or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, also bases of the pyridine type, for example pyridine, collidine or quinoline. Compounds of the formula I having a basic group can form acid addition salts, for example with inorganic acids such as hydrochloric acid, sulphuric acid or phosphoric acid, or with suitable organic carboxylic or sulphonic acids, for example trifluoroacetic acid, and also with amino acids, such as arginine and lysine. If several acid or basic groups are present, mono- or poly-salts can be formed. Compounds of the formula I having an acid group, for example a free carboxyl group, and a free basic group, for example an amino group, may also be in the form of internal salts, i.e. in zwitterion form, or one part of the molecule may be in the form of an internal salt and another part may be in the form of a normal salt.

For isolation and purification it is also possible to use pharmaceutically unacceptable salts. Only pharmaceutically acceptable non-toxic salts are used therapeutically and these are therefore preferred.

The acyl radical at the 7$\beta$-amino group contains two centres of asymmetry. The centre of asymmetry next to the 7-amino group is in the R,S-, the S- or preferably the R-configuration. The centre of asymmetry at the terminal aminocarboxylic acid grouping may have the R-, S- or R,S-configuration, the R-configuration being preferred in this case too.

The compounds of the formula I in which carboxyl groups are optionally esterified in a form that can be split under physiological conditions and their pharmaceutically acceptable non-toxic salts are valuable antibiotically active substances that may be used especially as antibacterial antibiotics. For example, they are effective in vitro against gram-positive and gram-negative microorganisms, such as against cocci, for example Staphylococcus, Streptococcus and Neisseria, and against *Haemophilus influenza*, in minimum doses of approximately 0.01 to 32 $\mu$g/ml, and against gram-negative bacteria, such as enterobacteria, for example *Escherichia coli*, Klebsiella, Salmonella or Proteus sp., or *Pseudomonas aeruginosa*, against Haemophilus and anaerobes in minimum doses of approximately 0.001 to 128 $\mu$g/ml. In vivo, on subcutaneous administration to mice, they are effective, for example in the case of gram-positive infections, for example caused by *Staphylococcus aureus*, in the dosage range of approximately 3 to 50 mg/kg, and in the case of gram-negative infections, for example caused by enterobacteria, such as *Escherichia coli*, Proteus sp. or Klebsiella, or *Pseudomonas aeruginosa*, in the dosage range of 2 to 100 mg/kg.

The new compounds may therefore be used accordingly, for example in the form of antiobiotically active preparations, for the treatment of systemic infections caused by gram-positive or especially gram-negative bacteria and cocci, especially by *Escherichia coli*, the minimum ED$_{50}$ in the case of subcutaneous injection being approximately 3 mg/kg.

Compounds of the formula I in which the functional groups are protected are used as starting materials for the manufacture of compounds of the formula I.

The present invention relates especially to those compounds of the formula I in which the group —($C_nH_{2n}$)— is unbranched and the indices n, m, and k have the meanings indicated, X represents oxygen or the group —NH—, W represents a group —CO— or —CO—NH-SO$_2$—, or X—W together represent a group —CO— or —CO—NHSO$_2$—, A represents p, o or m-phenylene, 2,5-thienylene or 2,5-furylene, Y represents 1,2-ethylene, R$_4$ represents hydrogen; lower alkyl optionally substituted by hydroxy, lower alkanoyloxy, lower alkoxycarbonyloxy, phenoxycarbonyloxy, lower alkoxy, lower alkylthio, halogen, optionally functionally modified carboxy or optionally mono- or di-lower alkylated amino; lower alkenyl; or acyl, Z represents oxygen or sulphur, R$_1$ represents hydrogen, lower alkyl, lower alkoxy, halogen or a group of the formula —CH$_2$—R$_2$ in which R$_2$ represents lower alkanoyloxy, carbamoyloxy, N-lower alkylcarbamoyloxy, triazolylthio, tetrazolythio, thiazolylthio, thiatriazolylthio, thiadiazolylthio, oxazolylthio, oxadiazolythio, 5,6-dioxotetrahydro-as-triazinylthio or pyridinio, in which the heterocyclic rings may optionally be substituted, for example by lower alkyl, N,N-di-lower alkylamino-lower alkyl, carboxy-lower alkyl, sulpho-lower alkyl, amino, carboxy-lower alkanoylamino or carbamoyl, and R$_3$ represents hydrogen or methoxy, pharmaceutically acceptable salts of such compounds, and the starting materials and intermediates that can be used for their manufacture.

Special mention should be made of compounds of the formula I in which the group —($C_nH_{2n}$)— is unbranched and the indices n, m and k have the meanings indicated, X represents oxygen or the group —NH—, W represents a group —CO— or —CONHSO$_2$—, or X—W together represent a group —CO— or —CONHSO$_2$—, A represents p, o or m-phenylene or, when m is 1, alternatively 2,5-thienylene or 2,5-furylene, Y represents 1,2-ethylene, R$_4$ represents hydrogen; lower alkyl optionally substituted by hydroxy, lower alkanoyloxy, lower alkoxycarbonyloxy, lower alkoxy, lower alkylthio, halogen, for example chlorine, carboxy, amino or di-lower alkylamino; lower alkenyl; lower alkanoyl optionally substituted by halogen, for example chlorine, lower alkoxy, lower alkanoyloxy, cyano or phenoxy; benzoyl optionally substituted by lower alkyl, hydroxy, lower alkoxy or chlorine; a pyridine-, pyrimidine- or pyrazine-carboxylic acid radical optionally substituted by hydroxy or chlorine; lower alkoxycarbonyl; arylsulphonyl, such as benzene-sulphonyl or naphthalenesulphonyl, optionally substituted by halogen, for example chlorine, or by lower alkyl; or carbamoyl, thiocarbamoyl, iminocarbamoyl (=guanyl) or sulphamoyl each optionally lower alkylated at the nitrogen atom, Z represents oxygen, R$_1$ represents hydrogen, methyl, methoxy, chlorine or a group of the formula —CH$_2$—R$_2$, in which R$_2$ represents acetoxy; carbamoyloxy; tetrazolylthio optionally substituted by methyl, carboxymethyl, sulphomethyl or dimethylaminoethyl, for example tetrazol-5-ylthio, 1-methyl-1H-tetrazol-5-ylthio, 1-sulphomethyl-1H-tetrazol-5-ylthio, 1-carboxymethyl-1H-tetrazol-5-ylthio or 1-(2-dimethylaminoethyl)-1H-tetrazol-5-ylthio; thiadiazolylthio, optionally substituted like tetrazolylthio, especially 2-methyl-1,3,4-thiadiazol-5-ylthio; 5,6-dioxotetrahydro-as-triazinylthio substituted by methyl, for example 2-methyl-5,6-dioxo-1,2,5,6-tetrahydro-as-triazin-3-ylthio or 4-methyl-5,6-dioxo-1,4,5,6-tetrahydro-as-triazin-3-ylthio; or carbamoylpyridinio, especially 4-carbamoylpyridinio, and R$_3$ represents hydrogen or methoxy, pharmaceutically acceptable salts of such compounds and the starting materials and intermediates that can be used for their manufacture.

Preferred compounds of the formula I are those in which the group —($C_nH_{2n}$)— represents methylene, the indices m and k have the meanings indicated, X represents oxygen and W represents a group —CO—, A represents p- or o-phenylene, Y represents 1,2-ethylene, R$_4$ represents hydrogen, lower alkyl, especially ethyl, or lower alkylsulphonyl, especially mesyl, Z represents oxygen, $R_1$ represents hydrogen, methyl, methoxy, chlorine or a group of the formula $—CH_2—R_2$, in which $R_2$ represents acetoxy; carbamoyloxy; tetrazolylthio optionally substituted by methyl, carboxymethyl, sulphomethyl or dimethylaminoethyl, especially 1-methyl-1H-tetrazol-5-ylthio, 1-sulphomethyl-1H-tetrazol-5-ylthio, 1-carboxymethyl-1H-tetrazol-5-ylthio or 1-(2-dimethylaminoethyl)-1H-tetrazol-5-ylthio; thiadiazolylthio, especially 2-methyl-1,3,4-thiadiazol-5-ylthio; 5,6-dioxotetrahydro-as-triazinylthio subsituted by methyl, for example 2-methyl-5,6-dioxo-1,2,5,6-tetrahydro-as-triazin-3-ylthio or 4-methyl-5,6-dioxo-1,4,5,6-tetrahydro-as-triazin-3-ylthio; or carbamoylpyridinio, especially 4-carbamoylpyridinio, and $R_3$ represents hydrogen or methoxy, pharmaceutically acceptable salts of such compounds and the starting materials and intermediates that can be used for their manufacture.

The invention relates especially to the compounds of the formula I described in the Examples, their pharmaceutically tolerable salts and the starting materials and intermediates described therein.

The compounds of the present invention are obtained according to processes known per se.

Compounds of the formula I in which the carboxyl groups are optionally esterified in a form that can be split under physiological conditions and their salts are manufactured by liberating the functional group(s) in a starting compound corresponding to the formula I in which at least one of the functional groups present is protected, if desired, in a resulting compound, converting a group $R_1$ into a different group $R_1$ and/or, if desired, converting a free carboxyl group into an esterified carboxyl group that can be split under physiological conditions and/or, if desired, separating a resulting mixture of isomers into the individual isomers and/or, if desired, converting a resulting compound into a salt or a resulting salt into a free compound or into a different salt.

The splitting off of protecting groups

In a resulting compound of the formula I in which one or more functional groups are protected, these, for example protected carboxyl, amino, hydroxy and/or sulpho groups, may be liberated in a manner known per se, optionally in stages or simultaneously, by means of solvolysis, especially hydrolysis, alcoholysis or acidolysis, or by means of reduction, especially hydrogenolysis or chemical reduction.

Thus, tert.-lower alkoxycarbonyl, or lower alkoxycarbonyl substituted in the 2-position by an organic silyl group or in the 1-position by lower alkoxy or lower alkylthio, or optionally substituted diphenylmethoxycarbonyl, can be converted into free carboxyl, for example by treating with a suitable acid, such as formic acid or trifluoroacetic acid, optionally with the addition of a nucleophilic compound, such as phenol or anisole. Optionally substituted benzyloxycarbonyl can be liberated, for example by means of hydrogenolysis, i.e. by treating with hydrogen in the presence of a metallic hydrogenation catalyst, such as a palladium catalyst. Furthermore, suitably substituted benzyloxycarbonyl, such as 4-nitrobenzyloxycarbonyl, can be converted into free carboxyl also by means of chemical reduction, for example by treating with an alkali metal dithionite, for example sodium dithionite, or with a reducing metal, for example zinc, or a reducing metal salt, such as a chromium(II) salt, for example chromium(II) chloride, usually in the presence of a hydrogen-yielding agent that, together with the metal, is capable of producing nascent hydrogen, such as an acid, especially a suitable carboxylic acid, such as a lower alkanecarboxylic acid optionally substituted, for example by hydroxy, for example acetic acid, formic acid, glycolic acid, diphenylglycolic acid, lactic acid, mandelic acid, 4-chloromandelic acid or tartaric acid, or of an alcohol or thiol, water preferably being added. By treating with a reducing metal or metal salt, as described above, it is also possible to convert 2-halo-lower alkoxycarbonyl, (optionally after converting a 2-bromo-lower alkoxycarbonyl group into a corresponding 2-iodo-lower alkoxycarbonyl group) or aroylmethoxycarbonyl, into free carboxyl, it also being possible to split aroylmethoxycarbonyl by treating with a nucleophilic, preferably salt-forming reagent, such as sodium thiophenate or sodium iodide. Substituted 2-silylethoxycarbonyl can also be converted into free carboxyl by treating with a salt of hydrofluoric acid yielding the fluoride anion, such as an alkali metal fluoride, for example sodium or potassium fluoride, in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic polar solvent, such as dimethyl sulphoxide or N,N-dimethylacetamide. Carboxyl esterified by an organic silyl or stannyl group, such as tri-lower alkylsilyl or tri-lower alkylstannyl, for example trimethylsilyl, can be liberated in the customary manner by solvolysis, for example by treating with water, an alcohol or an acid.

A protected amino group is liberated in a manner known per se and, depending on the type of protecting groups, in various manners, preferably by solvolysis or reduction. 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be split, for example by treating with a suitable chemical reducing agent, such as zinc in the presence of a suitable carboxylic acid, such as aqueous acetic acid. Aroylmethoxycarbonylamino can also be split by treating with a nucleophilic, preferably salt-forming reagent, such as sodium thiophenate, and 4-nitrobenzyloxycarbonylamino also by treating with an alkali metal dithionite, for example sodium dithionite. Optionally substituted diphenylmethoxycarbonylamino, tert.-lower alkoxycarbonylamino or 2-tri-substituted silylethoxycarbonylamino can be liberated by treating with a suitable acid, for example formic acid or trifluoroacetic acid, optionally substituted benzyloxycarbonylamino can be liberated, for example by hydrogenolysis, i.e. by treating with hydrogen in the presence of a suitable hydrogenation catalyst, such as a palladium catalyst, optionally substituted triarylmethylamino, formylamino or 2-acyl-lower alk-1-en-1-ylamino can be liberated, for example by treating with an acid, such as a mineral acid, for example hydrochloric acid, or an organic acid, for example formic acid, acetic acid or trifluoroacetic acid, optionally in the presence of water, and an amino group protected by an organic silyl or stannyl group can be liberated, for example by hydrolysis or alcoholysis. An amino group protected by 2-haloacetyl, for example 2-chloroacetyl, can be liberated by treating with thiourea in the presence of a base, or with a thiolate salt, such as an alkali metal thiolate, of thiourea and by subsequent solvolysis, such as alcoholysis or hydrolysis, of the resulting condensation product. An amino group protected by 2-substituted silylethoxycarbonyl can also be converted into the free amino group by treating with a salt of hydrofluoric acid yielding fluoride anions, as indicated above in connection with the liberation of a correspondingly protected carboxyl group. A phosphoramido, phosphonamido or phosphinamido group can be converted into the free amino group, for example by treating with a phosphorus-containing acid, such as a phosphoric, phosphonic or phosphinic acid, for example orthophosphoric acid or polyphosphoric acid, an acid ester thereof, for example monomethyl, monoethyl, dimethyl or diethyl phosphate, or monomethylphosphonic acid, or an anhydride thereof, such as phosphorus pentoxide.

An amino protected in the form of an azido group is converted into the free amino group, for example by reduction, for example by catalytic hydrogenation with hydrogen in the presence of a hydrogenation catalyst, such as platinum oxide, palladium or Raney nickel, or alternatively by treating with zinc in the presence of an acid, such as acetic acid. The catalytic hydrogenation is carried out preferably in an inert solvent, such as a halogenated hydrocarbon, for example methylene chloride, or alternatively in water or a mixture of water and an organic solvent, such as an alcohol or dioxan, at from approximately 20° C. to 25° C., or alternatively while cooling or heating.

A hydroxy group protected by a suitable acyl group, an organic silyl or stannyl group or by optionally substituted 1-phenyl-lower alkyl is liberated in the same manner as a correspondingly protected amino group. A hydroxy group protected by 2,2-dichloroacetyl is liberated, for example by basic hydrolysis, while a hydroxy group etherified by tert.-lower alkyl or by a 2-oxa- or 2-thia-aliphatic or -cycloaliphatic hydrocarbon radical is liberated by acidolysis, for example by treating with a mineral acid or a strong carboxylic acid, for example trifluoroacetic acid.

A protected, especially esterified, sulpho group is liberated analogously to a protected carboxyl group.

The splitting reactions described are carried out under conditions known per se, if necessary while cooling or heating, in a closed vessel and/or in an inert gas atmosphere, for example a nitrogen atmosphere.

When several protected functional groups are present, the protecting groups are preferably so chosen that more than one such group can be split off simultaneously, for example by acidolysis, such as by treating with trifluoroacetic acid or formic acid, or by reduction, such as by treating with zinc and acetic acid, or with hydrogen and a hydrogenation catalyst, such as a palladium-on-carbon catalyst.

Exchange of $R_2$ for a different $R_2$

In a compound of the formula I in which, if necessary, an amino group is protected and in which the carboxyl group in the 4-position of the cephem ring is in free form, a group $R_1$ can, in a manner known per se, be replaced by a different radical $R_1$ or converted into a different radical $R_1$. Thus, it is, for example, possible, in a compound of the formula I in which $R_1$ represents a group of the formula $—CH_2—R_2$, $R_2$ representing, for example, a radical that may be replaced by nucleophilic substituents, or in a salt thereof, to replace such a radical $R_2$ by an etherified or esterified mercapto group $R_2$ by treating with a corresponding mercaptan compound or with a thiocarboxylic acid compound. A suitable radical replaceable by an etherified mercapto group is, for example, a hydroxy group esterified by a lower aliphatic carboxylic acid. Such esterified hydroxy groups are especially acetoxy, but also formyloxy.

The reaction of such a compound with a suitable mercaptan compound can be carried out under neutral or weakly basic conditions in the presence of water and optionally a water-miscible organic solvent. The basic conditions can be established, for example by adding an inorganic base, such as an alkali metal hydroxide, carbonate or bicarbonate or an alkaline earth metal hydroxide, carbonate or bicarbonate, for example sodium, potassium or calcium hydroxide, carbonate or bicarbonate. It is possible to use as organic solvents, for example water-miscible alcohols, for example lower alkanols, such as methanol or ethanol, ketones, for example lower alkanones, such as acetone, amides, for example lower alkanecarboxylic acid amides, such as dimethylformamide, or nitriles, for example lower alkanoic acid nitriles, such as acetonitrile, and the like.

Esterified hydroxy groups $R_2$ in a compound of the formula I in which $R_1$ represents the group $—CH_2—R_2$, $R_2$ representing a hydroxy group esterified by the acyl radical of an optionally substituted semi-amide of carbonic acid, can be introduced, for example by reacting a corresponding compound of the formula I in which $R_2$ represents free hydroxy (which can be liberated, for example by splitting off the acetyl radical from an acetoxy group $R_2$, for example by hydrolysis in a weakly basic medium, such as with an aqueous sodium hydroxide solution at pH 9 to 10, or by treating with a suitable esterase, such as a corresponding enzyme from *Rhizobium tritolii, Rhizobium lupinii, Rhizobium japonicum* or *Bacillus subtilis*, or a suitable citrus esterase, for example from orange peel) with a suitable carbonic acid derivative, especially with an isocyanate compound or a carbamic acid compound, such as a silyl isocyanate, for example silyl tetraisocyanate, a sulphonyl isocyanate, for example chlorosulphonyl isocyanate, or carbamic acid halide, for example chloride, (which result in N-unsubstituted 3-aminocarbonyloxymethyl compounds), or with an N-substituted isocyanate compound or with an N-mono- or N,N-di-substituted carbamic acid compound, such as a corresponding carbamic acid halide, for example chloride, the reaction normally being carried out in the presence of a solvent or diluent and, if necessary, while cooling or heating, in a closed vessel and/or in an inert gas atmosphere, for example a nitrogen atmosphere.

In addition, it is possible to react a compound of the formula I in which $R_1$ represents a group $—CH_2—R_2$, $R_2$ representing, for example, the above-defined radical that can be replaced by nucleophilic substitution, with a tertiary organic base, especially an optionally substituted pyridine, under neutral or weakly acidic conditions, preferably at a pH of approximately 6.5, in the presence of water and optionally in a water-miscible organic solvent, and thus obtain a compound of the formula I in which $R_1$ represents the radical of the formula $—CH_2—R_2$, $R_2$ representing a quaternary ammonium group. The weakly acidic conditions can be established by adding a suitable organic or inorganic acid, for example acetic acid, hydrochloric acid, phosphoric acid or sulphuric acid. The above-mentioned water-miscible vents, for example, may be used as organic solvents. order to increase the yield, certain salts may be added the reaction mixture, for example alkali metal salts, :h as sodium and especially potassium salts, of inornic acids, such as hydrohalic acid, for example hydroloric acid and especially hydriodic acid, and of thioanic acid, or organic acids, such as lower alkanecarxylic acids, for example acetic acid. Examples of such ts are potassium iodide and potassium thiocyanate. It also possible to use for this purpose salts of suitable ion exchangers with acids, for example acetic acid, r example liquid ion exchangers in salt form, such as, r example, Amberlite LA-1 (liquid secondary amines ving a molecular weight of from 351 to 393; oil-solue and waterinsoluble; meq/g=2.5 to 2.7, for example acetate form).

Quaternary ammonium groups $R_2$ can be manufacred in an advantageous manner using an intermediate the formula I in which $R_2$ represents a substituted rbonylthio group, especially an aromatic substituted rbonylthio group and more especially the benzoylthio oup. An intermediate of this type, which can be obined, for example by reacting a compound of the forula I in which $R_2$ in the radical $R_1$ represents an esterid hydroxy group, especially a lower alkanoyloxy oup, for example an acetoxy group, with a suitable lt, such as an alkali metal salt, for example a sodium lt, of a thiocarbonic acid, such as an aromatic thiocarnic acid, for example thiobenzoic acid, is reacted with e tertiary amine, especially a tertiary heterocyclic se, such as an optionally substituted pyridine, the aternary ammonium compound being obtained. The action is usually carried out in the presence of a suitle desulphurising agent, especially a mercury salt, for ample mercury(II) perchlorate, and a suitable solvent r diluent or a mixture thereof, if necessary while coolig or heating, in a closed vessel and/or in an inert gas tmosphere, for example a nitrogen atmosphere.

Esterification of a free carboxyl group

The conversion of a free carboxyl group in a resulting ompound of the formula I into an esterified carboxyl roup that can be split under physiological conditions is arried out according to esterification methods known er se, for example by esterifying a compound of the ormula I, in which other functional groups, such as mino, hydroxy or sulpho groups, are present optionlly in protected form, or a functional derivative thereof hat is reactive with respect to the carboxyl group to be sterified, or a salt thereof, with a corresponding alcool or a reactive functional derivative thereof.

Salt formation

Salts of compounds of the formula I can be manufacured in a manner known per se. Thus, salts of compounds of the formula I having acid groups can be ormed, for example by treating with metal compounds, uch as alkali metal salts of suitable carboxylic acids, for xample the sodium salt of α-ethylcaproic acid or sodium carbonate, or with ammonia or a suitable organic amine, preferably stoichiometric quantities or only a small excess of the salt-forming agent being used. Acid addition salts of compounds of the formula I are obtained in the customary manner, for example by treating with an acid or a suitable anion exchange reagent. Internal salts of compounds of the formula I that contain a free carboxyl group can be formed, for example by neutralising salts, such as acid addition salts, to the isoelectric point, for example with weak bases, or by treating with liquid ion exchangers.

Salts can be converted in the customary manner into the free compounds; metal and ammonium salts can be converted, for example by treating with suitable acids, and acid addition salts can be converted, for example by treating with a suitable basic agent.

The process also includes those embodiments according to which compounds formed as intermediates are used as starting materials and the remaining process steps are carried out with these, or the process is interrupted at any stage; furthermore, starting materials may be used in the form of derivatives or formed during the reaction.

Preferably, the starting materials and the reaction conditions are so chosen that the compounds described above as being especially preferred are obtained.

Manufacture of protected compounds of the formula I

The invention also relates to the starting compounds of the formula I in which at least one of the functional groups is in protected form and to processes for their manufacture. These compounds and salts of such compounds having a salt-forming group can be manufactured in a manner known per se by, for example, (a) in a compound of the formula

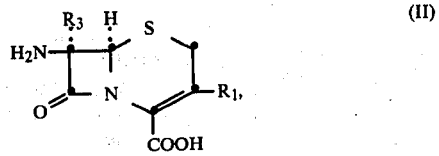

in which the amino group is optionally substituted by a group allowing acylation and in which the 4-carboxyl group and other functional groups optionally present in the radical $R_1$ may be in protected form, acylating the amino group by treating with an acid of the formula

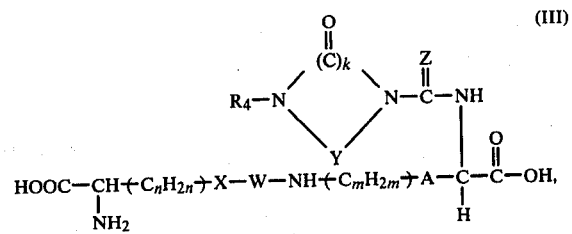

in which the aminocarboxylic acid grouping HOOC—CH(NH$_2$)— and other functional groups optionally present in the groupings A and $R_4$ are in protected form, or with a reactive functional acid derivative or a salt thereof, or (b) in a compound of the formula

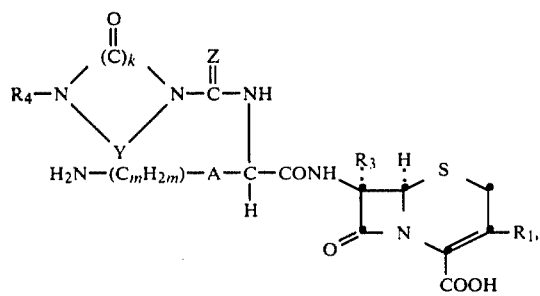

(IV)

in which the amino group may optionally be substituted by a group allowing acylation and in which the 4-carboxyl group and other functional groups optionally present in $R_1$ and in the groupings A and $R_4$ may be in protected form, acylating the amino group by treating with a reactive functional derivative of an acid of the formula

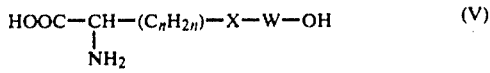

(V)

in which the aminocarboxylic acid grouping HOOC—CH($NH_2$)— is in protected form or, when X—W together represent a group —CO—, alternatively with a corresponding free acid, or with a salt thereof, or (c) in a compound of the formula

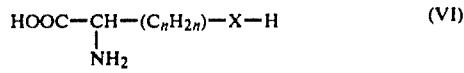

(VI)

in which X represents oxygen, sulphur or the group —NH— and in which the aminocarboxylic acid grouping HOOC—CH($NH_2$)— is in protected form, acylating the group —X—H with a reactive functional derivative of a compound of the formula

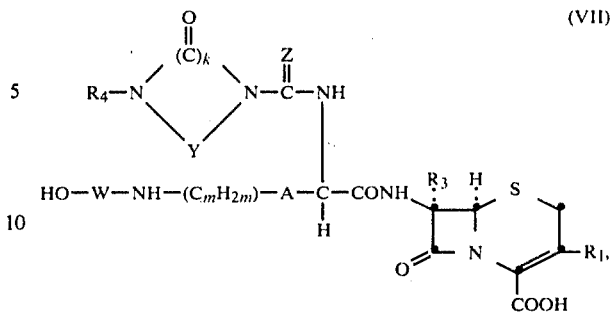

(VII)

in which the 4-carboxyl group and functional groups optionally present in the radical $R_1$ and in the groupings A and $R_4$ may be in protected form, or (d) in a compound of the formula

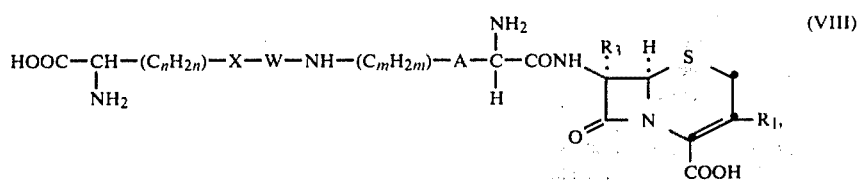

(VIII)

in which the aminocarboxylic acid grouping HOOC—CH($NH_2$)— is in protected form, the amino group to be acylated is optionally substituted by a group allowing acylation and the 4-carboxyl group and other functional groups optionally present in the radical $R_1$ and in the grouping A may be in protected form, acylating the amino group by treating with an acylating agent introducing the corresponding acyl radical of a carbonic or thiocarbonic acid of the formula

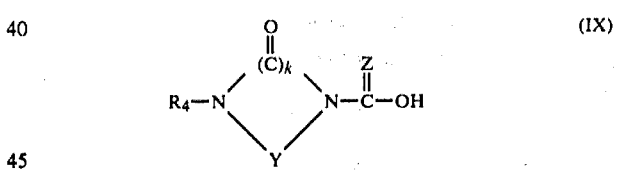

(IX)

in which functional groups optionally present in the radical $R_4$ may be in protected form, or (e) reacting a reactive derivative of a carbonic or thiocarbonic acid compound of the formula

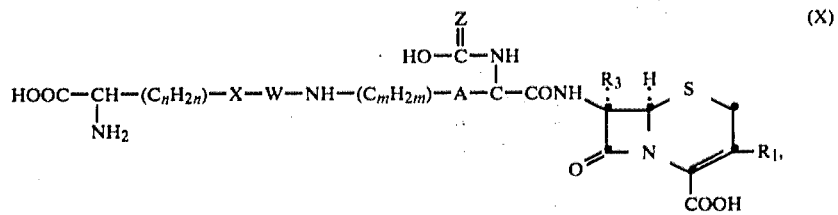

(X)

in which the aminocarboxylic acid grouping HOOC—CH($NH_2$)— is in protected form and in which the 4-carboxyl group and other functional groups optionally present in the radical $R_1$ and in the grouping A may be in protected form, with a secondary amide of the formula (XI)

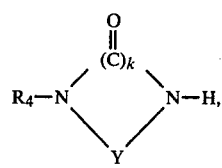

in which functional groups optionally present in the radical R$_4$ may be protected and the secondary amido group is in a form allowing acylation, or (f) carrying out in situ the acylation mentioned under (d) or (e) by allowing an amino compound of the formula VIII and an amido compound of the formula XI, each with the meanings indicated above, to act simultaneously or in succession on a bivalent reactive derivative of carbonic or thiocarbonic acid, or (g) diacylating with a bivalent acylating derivative of carbonic acid or oxalic acid with cyclisation, a compound of the formula (XII)

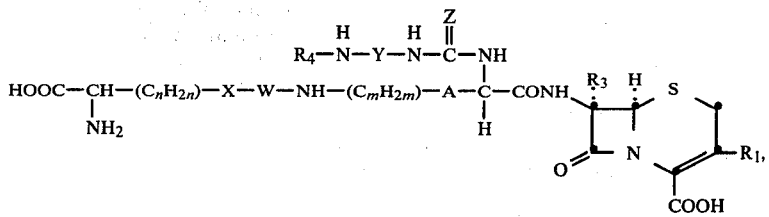

in which the aminocarboxylic acid grouping HOOC—CH(NH$_2$)— is in protected form, the 4-carboxyl group and functional groups optionally present in the radical R$_1$ and in the grouping A may be in protected form and the secondary amino/amido groups later forming the piperazine ring are optionally substituted by groups allowing N-acylation, or (h) isomerising a 2-cepham compound of the formula in which functional groups are protected, to form the corresponding 3-cephem compound of the formula I, or (i) in a compound of the formula (XIV)

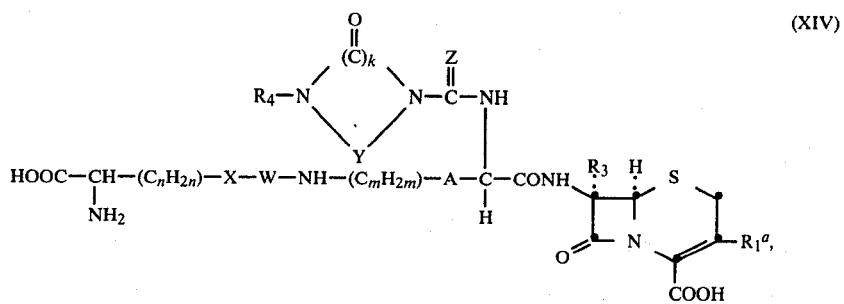

in which R$_1^a$ is a free or sulphonated hydroxy group and in which other functional groups are protected, exchanging R$_1^a$ for halogen, or (j) in a compound of the formula XIV in which R$_1^a$ is a free hydroxy group and in which other functional groups are protected, etherifying the hydroxy group, or (k) in a compound of the formula XIV in which functional groups are protected and in which R$_1^a$ represents a formyl group, decarbonylating this in the presence of decarbonylation catalysts to form a compound of the formula I in which R$_1$ represents hydrogen, or (l) in a compound of the formula XIV in which R$_1^a$ is free or esterified hydroxy or an optionally lower alkylated amino group or amino optionally cyclically disubstituted by lower alkylene or hetero-lower alkylene and in which functional groups are protected, replacing the group R$_1^a$ by hydrogen, and, if desired, in a resulting compound, protecting functional groups that are still not protected or exchanging a protecting group for a different protecting group and/or, if desired, in a radical R$_1$, exchanging a group R$_2$ for a different group R$_2$ and/or, if desired, converting a resulting compound in which R$_3$ represents hydrogen into a compound in which R$_3$ represents methoxy and/or, if desired, separating a resulting mixture of isomers into the individual isomers and/or, if desired, converting a resulting compound into a salt or converting a resulting salt into the free compound or into a different salt.

(XIII)

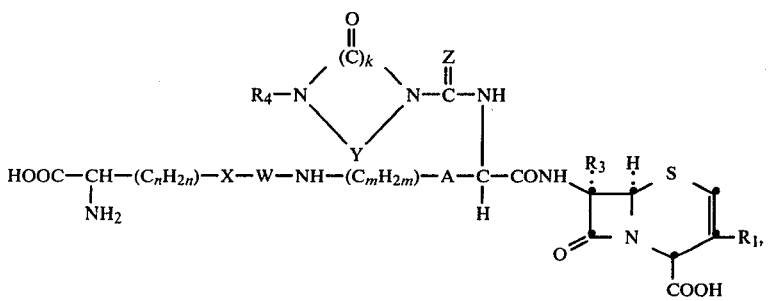

Processes (a) to (g) (acylations)

In a starting material of the formulae II, IV, VIII, XI and XII, optionally present radicals that substitute the amino group and allow the acylation thereof are, for example, organic silyl or stannyl groups and also ylidene groups which, together with the amino group, form a Schiff's base. The said organic silyl or stannyl groups are, for example, the same as those that are also capable of forming a protected carboxyl group with the 4-carboxyl group on the cephem ring. These are especially tri-lower alkylsilyl, especially trimethylsilyl. When silylating or stannylating a carboxyl group in a starting material of the formula II, IV, VIII, XI or XII it is possible, by using an excess of the silylating or stannylating agent, also to silylate or stannylate the amino group. The ylidene groups mentioned are especially 1-aryl-lower alkylidene groups, especially arylmethylene groups in wich aryl represents especially a carbocyclic, especially monocyclic, aryl radical, for example phenyl optionally substituted, for example by lower alkyl, hydroxy, lower alkoxy and/or nitro; such arylmethylene groups are, for example benzylidene, 2-hydroxybenzylidene or 4-nitrobenzylidene, and also oxacycloalkylidene optionally substituted, for example by carboxy, for example 3-carboxy-2-oxacyclohexylidene.

The functional groups present in the starting materials of the formulae II to XIV may be protected by the protecting groups already mentioned under the compounds of the formula I. All reactive functional groups not participating in the reacting reactions, but especially optionally present carboxyl, sulpho, amino, hydroxy and mercapto groups, are preferably protected.

Acylating agents introducing the acyl radical of a carboxylic acid are, for example carboxylic acid itself, if, as in the case of an acid of the formula III or V or of an oxalic acid it is sufficiently stable, or reactive functional derivatives thereof.

If according to acylation process (a), (b) or (g) a free acid of the formula III or V, in which all functional groups apart from the reacting carboxyl group are protected, or oxalic acid is used for acylation, suitable condensing agents are usually used, such as carbodiimides, for example N,N'-diethyl-, N,N'-dipropyl-, N,N'-diisopropyl-, N,N'-dicyclohexyl- or N-ethyl-N'-3-dimethylaminopropyl-carbodiimide, suitable carbonyl compounds, for example carbonyldiimidazole, or isoxazolinium salts, for example N-ethyl-5-phenylisoxazolinium 3'-sulphonate and N-tert.-butyl-5-methylisoxazolinium perchlorate, or an acylamino compound, for example 2-ethoxy-1-ethoxycarbonyl-1,2-dihydroquinoline.

The condensation reaction is carried out preferably in an anhydrous reaction medium, preferably in the presence of a solvent or diluent, for example methylene chloride, dimethylformamide, acetonitrile or tetrahydrofuran, if desired or necessary while cooling or heating, for example in a temperature range of from approximately $-40°$ C. to approximately $+100°$ C., preferably from approximately $-20°$ C. to $+50°$ C., and/or in an inert gas atmosphere.

A reactive, i.e. amide-forming, or ester-forming, functional derivative of an acid of the formula III, V, VII, IX or X, in which all functional groups apart from the reacting acid group are or may be protected, or of carbonic acid or oxalic acid, is especially an anhydride of such an acid, including and preferably a mixed anhydride, but alternatively an internal anhydride, i.e. a corresponding ketene or, in acid V, when W is the group $-SO_2NH-CO-$, or when X is the group $-NH-$ and W is the group $-CO-$ or $-CO-NH-SO_2-$, or in the case of acid X, a corresponding isocyanate. Mixed anhydrides are, for example, those with inorganic acids, such as hydrohalic acids, i.e. the corresponding acid halides, for example chlorides or bromides; and also with hydrazoic acid, i.e. the corresponding acid azides; with a phosphorus-containing acid, for example phosphoric acid or phosphorous acid; or with a sulphur-containing acid, for example sulphuric acid; or with hydrocyanic acid. Further mixed anhydrides are, for example, those with organic carboxylic acids, such as with lower alkanecarboxylic acids optionally substituted, for example by halogen, such as fluorine or chlorine, for example pivalic acid or trichloroacetic acid; or with semi-esters, especially lower alkyl semi-esters of carbonic acid, such as the ethyl or isobutyl semi-ester of carbonic acid; or with organic, especially aliphatic or aromatic, sulphonic acids, for example p-toluene-sulphonic acid.

Further acid derivatives of an acid of the formula III, V, VII, XI or X, in which all functional groups apart from the reacting carboxyl group are or may be protected, or of carbonic or oxalic acid, that are suitable for reaction with the amino, hydroxy or mercapto group, are activated esters, such as esters with vinylogous alcohols (i.e. enols), such as vinylogous lower alkenols, cyanomethyl esters, trichloromethyl esters, iminomethyl ester halides, such as dimethyliminomethyl ester chlorides (manufactured from the carboxylic acid and dimethylchloromethylideneiminium chloride of the formula $[(CH_3)_2N=CHCl]^{\oplus}Cl^{\ominus}$ which can be obtained, for example from N,N-dimethylacetamide and phosgene), or aryl esters, such as phenyl esters, preferably suitably substituted, for example by halogen, such as chlorine, and/or by nitro, for example 4-nitrophenyl esters, 2,3- or 2,4-dinitrophenyl esters or 2,3,4,5,6-pentachlorophenyl esters, N-hetero-aromatic esters, such as N-benztriazole esters, for example 1-benztriazole esters, or N-diacylimino esters, such as N-succinylimino esters or N-phthalylimino esters.

The acylation with an acid derivative, such as an anhydride, especially with an acid halide, is carried our preferably in the presence of an acid-binding agent, for example an organic base, such as an organic amine, for example a tertiary amine, such as tri-lower alkylamine, for example trimethylamine, triethylamine or ethyldiisopropylamine, or N,N-di-lower alkylaniline, for example N,N-dimethylaniline, or a cyclic tertiary amine, such as an N-lower alkylated morpholine, such as N-methylmorpholine, or a base of the pyridine type, for example pyridine, or an inorganic base, for example an alkali metal or alkaline earth metal hydroxide, carbonate or bicarbonate, for example sodium, potassium or calcium hydroxide, carbonate or bicarbonate, or an oxirane, for example a lower 1,2-alkylene oxide, such as ethylene oxide or propylene oxide. These bases play a part especially in the acylation of amino groups. In the acylation of amide groups it is more advantageous to use as the acid-binding agent a neutral proton acceptor, for example one selected from the group of oxiranes, such as a lower 1,2-alkylene oxide, for example ethylene oxide, or a reactive olefin, such as lower alkylene, for example propylene, or a molecular sieve, for example a pulverulent Type 4 Å molecular sieve, and/or the previously or in situ-silylated or stannylated, such as trilower alkyl-silylated, for example trimethyl-silylated, amide group is reacted. In the case of the mentioned amide-acylating reactions, for example mixed anhydrides, especially the corresponding acid chlorides, that is to say acid chlorides of the compounds of the formula X, and the mono- or di-acid chlorides of carbonic acid, thiocarbonic acid or oxalic acid are used.

The above acylation reactions may be carried out in an inert, optionally anhydrous solvent or mixture of solvents, for example in a carboxylic acid amide, such as a formamide, for example dimethylformamide, in a halogenated hydrocarbon, for example methylene chloride, carbon tetrachloride or chlorobenzene, in a ketone, for example acetone, in an ester, for example ethyl acetate, or in a nitrile, for example acetonitrile, or mixtures thereof, and, if necessary, at reduced or elevated temperature, for example in a temperature range of from approximately $-50°$ C. to approximately $+100°$ C., preferably from approximately $-10°$ C. to approximately $+40°$ C., and/or in an inert gas atmosphere, for example a nitrogen atmosphere. To increase the solubility of the reagents, especially the amines of the formula III to be acylated, if these are used as salts, it is also possible to add water to the solvent. For example, acetone/water in the ratio of 0.5:1 to 3:1 is an especially suitable solvent mixture.

In an acylating acid of the formula III, V or VII or in an acid derivative thereof, a protected amino group may also be in ionic form, i.e. the starting material of the formula III, V or VII may be used in the form of an acid addition salt, preferably with a strong inorganic acid, such as a hydrohalic acid, for example hydrochloric acid, or sulphuric acid.

It is also possible, if desired, to form an acid derivative in situ. For example, a mixed anhydride is obtained by treating an acid of the formula III, or an acid of the formula V in which X-W represents the group —CO—, having correspondingly protected functional groups, or by treating a suitable salt thereof, such as an ammonium salt, for example a salt with an organic amine, such as 4-methylmorpholine, or by treating a metal salt, for example an alkali metal salt, with a suitable acid derivative, such as a corresponding acid halide of an optionally substituted lower alkanecarboxylic acid, for example trichloroacetyl chloride, or with a semi-ester of a carbonic acid halide, for example ethyl chloroformate or isobutyl chloroformate, and the mixed anhydride so obtained is used without being isolated.

An acid chloride of an acid of the formula V in which X—W is a grouping —O—CO—, —S—CO— or —NH—CO— and in which the aminocarboxylic acid grouping HOOC—CH(NH$_2$)— is in protected form can be formed, for example in situ, by treating an aminocarboxylic acid of the formula VI, in which X represents oxygen, sulphur or the group —NH— and the grouping HOOC—CH(NH$_2$)— is in protected form, with phosgene in an inert organic solvent of solvent mixture in the presence of a hydrochloric acid acceptor. The hydrochloric acid acceptors, solvents and reaction conditions are the same as those given for the acylation of compounds of the formula II or IV; for example, the reaction may take place in the presence of pyridine in methylene chloride and toluene at from approximately 0° C. to approximately $+10°$ C.

In the same manner it is possible to manufacture, for example in situ, an acid chloride of an acid of the formula VII, in which W represents the group —SO$_2$NH—CO— and in which the 4-carboxyl group and further functional groups optionally present in the groups A, R$_4$ and R$_1$ are protected, from a correspondingly protected compound of the formula IV by treating with chlorosulphonyl isocyanate.

In an analogous manner, an acid chloride of an acid of the formula IX or X can be manufactured from a secondary amide of the formula XI or from an amine of the formula VIII, respectively, and phosgene.

It is even preferred to manufacture in situ the corresponding reactive acid derivatives of the carbonic or thiocarbonic acid of the general formula IX and X by allowing a bivalent reactive derivative of carbonic or thiocarbonic acid, such as one of those mentioned below, preferably a corresponding acid chloride, such as phosgene, thiophosgene or a chloroformic acid derivative to act on the corresponding amino compounds of the general formulae XI and VIII, respectively, preferably in the presence of one of the above-mentioned neutral proton acceptors.

The preferred acylating agent introducing the acyl radical of a carbonic or thiocarbonic acid of the formula IX, according to acylation process (d), is therefore the corresponding carbamic or thiocarbamic acid halide, especially chloride.

The preferred carbonic or thiocarbonic acid compound of the formula X according to acylation process (e) is likewise the corresponding carbamic or thiocarbamic acid halide, for example the corresponding chloride which, however, in contrast to the corresponding derivative of the general formula IX, can, as the derivative of a primary amine, readily form the corresponding isocyanate or isothiocyanate, respectively, while splitting off hydrogen halide, for example hydrogen chloride, and can be converted spontaneously as such with amides of the formula XI into the compound according to the invention of the formula I with the formation of the urea grouping. It is advantageous, in processes (d) and (e) too, to use nonpolar inert solvents, such as chloro-lower aliphatics, for example methylene chloride, chloroform or an optionally chlorinated aromatic solvent, such as benzene, toluene or chlorobenzene, or an inert ethereal solvent, such as tetrahydrofuran or dioxan, and to carry out the reaction at or below room temperature, that is, with cooling. Bivalent reactive derivatives of carbonic, thiocarbonic or oxalic acid, which are used for the acylation processes mentioned under (f) and (g), are the corresponding acid halides, such as acid chlorides, for example phosgene or oxalyl chloride, orthoesters, such as lower alkyl orthoesters, for example orthocarbonic acid tetramethyl ester, imidoesters, such as imidocarbonic acid lower alkyl esters, for example imidocarbonic acid dimethyl ester, ester halides, such as haloformic acid lower alkyl esters, for example chloroformic acid methyl ester, imidohalides, such as imidocarbonic acid halides, for example carbonic acid imidochloride, activated esters, such as corresponding enol or aryl esters, for example bis-(p-nitrophenyl) carbonate, or activated amides, such as corresponding heterocyclic bis-amides of carbonic acid, for example carbonyldiimidazole. Preferred compounds of this type are carbonic or thiocarbonic acid halides, for example phosgene, thiophosgene or carbonic acid dibromide, tetramethyl orthocarbonate, chlorocarbonic acid imidochloride, cyanogen chloride, chloroformic acid esters, such as the corresponding methyl, trichloromethyl, benzyl or phenyl ester, imidocarbonic acid diethyl ester or diphenyl ester, carbonyldiimidazole, carbonylditetrazole, or carbonic acid di-(p-nitrophenyl)

ester, and also corresponding compounds of oxalic acid, for example oxalyl chloride.

The acylating bivalent derivatives of carbonic acid or oxalic acid used in acylation process (g) and also the corresponding bivalent reactive derivatives used in process (f) may be used a priori in doubly reactive form or reacted in the form of a mono-reactive semi-derivative of carbonic or thiocarbonic acid (in which only one acid radical is present in reactive form), the second reactive group of which is subsequently formed or activated and reacted (with a second reaction component).

Preferably, in process (g) phosgene or oxalyl chloride, especially in a 2-10 molar excess, is placed in a non-polar inert solvent, such as methylene chloride, and the protected compound of the formula XII, which is silylated at the terminal amino groups, is allowed to act thereon. As an additional step, a second acid-binding agent, such as propylene or propylene oxide, can be used and the acylation can be carried out while cooling, for example at or below 0° C.

The acylation of a compound of the formula II can also be effected by using a suitable derivative of the acid of the formula III in the presence of a suitable acylase. Such acylases are known and can be formed by a number of micro-organisms, for example by acetobacter, such as *Acetobacter aurantium*, achromobacter, such as *Achromobacter aeris*, aeromonas, such as *Aeromonas hydrophila*, or bacillus, such as *Bacillus megaterium* 400. In such an enzymatic acylation, there are used as suitable derivatives especially amides, esters or thioesters, such as lower alkyl esters, for example methyl or ethyl ester, of the carboxylic acid of the formula III. Acylation of this kind is usually carried out in a nutrient medium containing the corresponding micro-organism, in a filtrate of the culture broth or, optionally after isolation of the acylase, including after adsorption on a carrier, in an aqueous medium optionally containing a buffer, for example in a temperature range of from approximately +20° C. to approximately +40° C., preferably at approximately +37° C.

Process (h) (Isomerisation)

In a 2-cephem starting material of the formula XIII, the optionally protected carboxyl group in the 4-position of the cephem ring is preferably in the α-configuration.

2-cephem compounds of the formula XIII can be isomerised by being treated with a weakly basic agent and isolating the corresponding 3-cephem compound. Suitable isomerising agents are, for example, organic nitrogencontaining bases, especially tertiary heterocyclic bases of aromatic character, especially bases of the pyridine type, such as pyridine itself and picolines, collidines or lutidines, and also quinoline, tertiary aromatic bases, for example those of the aniline type, such as N,N-dilower alkylanilines, for example N,N-dimethylaniline or N,N-diethylaniline, or tertiary aliphatic, azacycloaliphatic or araliphatic bases, such as N,N,N-tri-lower alkylamines, for example N,N,N-trimethylamine or N,N-diisopropyl-N-ethylamine, N-lower alkylazacycloalkanes, for example N-methylpiperidine, or N-phenyl-lower alkyl-N,N-di-lower alkylamines, for example N-benzyl-N,N-dimethylamine, and also mixtures of such basic agents, such as the mixture of a base of the pyridine type and an N,N,N-tri-lower alkylamine, for example pyridine and triethylamine. Furthermore, inorganic or organic salts of bases, especially of medium-strength to strong bases with weak acids, such as alkali metal or ammonium salts of lower alkanecarboxylic acids, for example sodium acetate, triethylammonium acetate or N-methylpiperidine acetate, and other analogous bases or mixtures of such basic agents can also be used.

Isomerisation of 2-cephem compounds of the formula XIII with basic agents is carried out preferably in an anhydrous medium, in the presence or absence of a solvent, such as an optionally halogenated, for example chlorinated, aliphatic, cycloaliphatic or aromatic hydrocarbon, or a solvent mixture, it being possible for the bases used as reagents which are liquid under the reaction conditions simultaneously to serve as solvents, optionally while cooling or heating, preferably within a temperature range of from approximately −30° C. to approximately +100° C., in an inert gas atmosphere, for example a nitrogen atmosphere, and/or in a closed vessel.

3-Cephem compounds of the formula I obtainable in this manner can be separated in a manner known per se, for example by adsorption and/or crystallisation, from 2-cephem starting materials which may optionally still be present.

The isomerisation of 2-cephem compounds of the formula XIII is preferably carried out by oxidising these in the 1-position, optionally separating isomeric mixtures of the 1-oxides formed and, if desired, reducing the resulting 1-oxides of the corresponding 3-cephem compounds.

Suitable oxidising agents for the oxidation in the 1-position of 2-cephem compounds of the formula XIII are inorganic peracids that have a reduction potential of at least 1.5 volts and consist of non-metallic elements, organic peracids or mixtures consisting of hydrogen peroxide and acids, especially organic carboxylic acids, having a dissociation constant of at least $10^{-5}$. Suitable inorganic peracids are periodic acid and persulphuric acid. Organic peracids are corresponding percarboxylic and persulphonic acids which are added as such or may be formed in situ by using at least one equivalent of hydrogen peroxide and a carboxylic acid. In this case, it is expedient to use a large excess of the carboxylic acid if, for example, acetic acid is used as solvent. Suitable peracids are, for example, performic acid, peracetic acid, trifluoroperacetic acid, permaleic acid, perbenzoic acid, 3-chloroperbenzoic acid, monoperphthalic acid or p-toluenepersulphonic acid.

The oxidation can likewise be effected using hydrogen peroxide with catalytic quantities of an acid having a dissocation constant of at least $10^{-5}$, it being possible to use low concentrations, for example 1 to 2% and lower, or alternatively larger amounts of the acid. In this case, the effectiveness of the mixture depends mainly on the strength of the acid. Suitable mixtures are, for example, those of hydrogen peroxide with acetic acid, perchloric acid or trifluoroacetic acid.

The above oxidation may be carried out in the presence of suitable catalysts. Thus, for example, the oxidation with percarboxylic acids can be catalysed by the presence of an acid having a dissocation constant of at least $10^{-5}$, the effectiveness of this acid being dependent on its strength. Acids suitable as catalysts are, for example, acetic acid, perchloric acid and trifluoroacetic acid. Usually, at least equimolar amounts of the oxidising agent, and preferably a slight excess of from approximately 10% to approximately 20%, are used, it also being possible to use larger excesses, i.e. up to 10 times the amount or more of the oxidising agent. The oxidation is carried out under mild conditions, for example at temperatures of from approximately −50° C. to approximately +100° C., preferably from approximately −10° C. to approximately +40° C.

The reduction of the 1-oxides of 3-cephem compounds can be carried out in a manner known per se by treating with a reducing agent, if necessary in the presence of an activating agent. Suitable reducing agents are, for example: catalytically activated hydrogen, there being used noble metal catalysts that contain palladium, platinum or rhodium and which are optionally employed together with a suitable carrier material, such as carbon or barium sulphate; reducing tin, iron, copper or manganese cations, which are used in the form of corresponding compounds or complexes of an inorganic or organic kind, for example in the form of tin(II) chloride, fluoride, acetate or formate, iron(II) chloride, sulphate, oxalate or succinate, copper(I) chloride, benzoate or oxide, or manganese(II) chloride, sulphate, acetate or oxide, or in the form of complexes, for example with ethylenediaminetetraacetic acid or nitrolotriacetic acid; reducing dithionite, iodide or iron(II) cyanide anions, which are used in the form of corresponding inorganic or organic salts, such as alkali metal dithionite, for example sodium or potassium dithionite, sodium or potassium iodide or sodium or potassium iron(II) cyanide, or in the form of the corresponding acids, such as hydriodic acid; reducing trivalent inorganic or organic phosphorus compounds, such as phosphines, also esters, amides and halides of phosphinous, phosphonous or phosphorous acid, and also phosphorus-sulphur compounds corresponding to these phosphorus-oxygen compounds, in which organic radicals are especially aliphatic, aromatic or araliphatic radicals, for example optionally substituted lower alkyl, phenyl or phenyl-lower alkyl, such as, for example, triphenylphosphine, tri-nbutylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide, etc.; reducing halosilane compounds that have at least one hydrogen atom bonded to the silicon atom and which may contain, apart from halogen, such as chlorine, bromine or iodine, also organic radicals, such as aliphatic or aromatic groups, for example optionally substituted lower alkyl or phenyl, such as chlorosilane, bromosilane, di- or tri-chlorosilane, di- or tri-bromosilane, diphenylchlorosilane or dimethylchlorosilane, and also halosilane compounds in which all the hydrogen atoms are replaced by organic radicals, such as a tri-lower alkylhalosilane, for example trimethylchlorosilane or trimethyliodosilane, or cyclic sulphur-containing silanes, such as 1,3-dithia2,4-disilacyclobutanes or 1,3,5-trithia-2,4,6-trisilacyclohexanes, of which the silicon atoms are substituted by hydrocarbon radicals, such as especially lower alkyl, for example 2,2,4,4-tetramethyl-1,3-dithia-2,4-disilacyclobutane or 2,2,4,4,6,6-hexamethyl-1,3,5-trithia-2,4,6-trisilacyclohexane, etc.; reducing quaternary chloromethyleneiminium salts, especially chlorides or bromides, in which the iminium group is substituted by one bivalent or two monovalent organic radicals, such as optionally substituted lower alkylene or lower alkyl, such as N-chloromethylene-N,N-diethyliminium chloride or N-chloromethylenepyrrolidinium chloride; or complex metal hydrides, such as sodium borohydrides, in the presence of suitable activating agents, such as cobalt(II) chloride, and also borane dichloride.

As activating agents which are used with those of the above-mentioned reducing agents that do not themselves have the properties of Lewis acids, i.e. those which are used mainly with the dithionite, iodide or iron(II) cyanide reducing agents and the trivalent phosphorus reducing agents that do not contain halogen, or are used in the catalytic reduction, there may be mentioned especially organic carboxylic and sulphonic acid halides but also sulphur, phosphorus or silicon halides having a second order hydrolysis constant which is the same as or greater than that of benzoyl chloride, for example phosgene, oxalyl chloride, acetyl chloride or bromide, chloroacetic acid chloride, pivaloyl chloride, 4-methoxybenzoyl chloride, 4-cyanobenzoyl chloride, p-toluenesulphonyl chloride, methanesulphonyl chloride, thionyl chloride, phosphorus oxychloride, phosphorus trichloride, phosphorus tribromide, phenyldichlorophosphine, benzenephosphonous acid dichloride, dimethylchlorosilane or trichlorosilane, also suitable acid anhydrides, such as trifluoroacetic acid anhydride, or cyclic sultones, such as ethanesultone, propanesultone, 1,3-butanesultone or 1,3-hexanesultone.

The reduction is carried out preferably in the presence of solvents or mixtures thereof, the choice of which is determined mainly by the solubility of the starting materials and the chosen reducing agent: thus, for example, lower alkanecarboxylic acids or esters thereof, such as acetic acid and ethyl acetate, in the case of catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofuran or dioxan, ketones, for example acetone, or sulphones, especially aliphatic sulphones, for example dimethylsulphone or tetramethylenesulphone, etc., together with the chemical reducing agents, these solvents preferably containing no water. The reaction is usually carried out at temperatures of from approximately −20° C. to approximately 100° C., it being possible, when using very reactive activating agents, to carry out the reaction also at lower temperatures.

Process (i) (Exchange of free or sulphonated hydroxy for halogen)

The exchange of the free hydroxy group $R_1^a$ for halogen is carried out in a manner known per se, for example by treating with a halogenating, especially chlorinating, agent. Suitable halogenating agents for introducing chlorine or bromine are, for example, phosphorus reagents, such as dihalotriorganophosphoranes, trihalodiorganophosphoranes or a mixture consisting of a triorganophosphine and a tetrahalomethane. Representative examples of the mentioned phosphoranes are dichlorotriphenylphosphorane, trichlorodiphenylphosphorane and dibromotriphenylphosphorane. Representative examples of the mentioned phosphines are triethylphosphine, tris(dimethylamino)-phosphine and especially triphenylphosphine. Tetrahalomethanes are, for example, carbon tetrabromide and especially carbon tetrachloride.

The reaction with the halogenating phosphorus reagents takes place in a manner known per se in an inert, aprotic, preferably polar, solvent, such as a chlorinated hydrocarbon, for example methylene chloride, chloroform, carbon tetrachloride, 1,2-dichloroethane, a nitrile, such as acetonitrile, or benzonitrile, or an N,N-di-substituted carboxylic acid amide, such as dimethylformamide or N,N-dimethylacetamide, or mixtures thereof, depending on the reactivity of the reagent used while cooling or heating, i.e. at temperatures between approximately −60° C. and up to the reflux temperature of the solvent used, optionally in an inert gas atmosphere, such as a nitrogen atmosphere. When using tri-lower alkylphosphines or tris-(di-lower alkylamine)-phosphines and carbon tetrachloride or carbon tetrabromide cooling, approximately to −60° C. to −20° C., is usually necessary. When halogenating with the mentioned phosphoranes, a weak base, such as pyridine or a di-lower alkylaniline, such as dimethylaniline, or a neutral proton acceptor, such as propylene, may be added to the reaction medium in order to bind resulting hydrogen halide.

Other important halogenating agents are corresponding to N,N-di-lower alkylated halo-iminium halide compounds, especially of the formula $[(CH_3)_2N=CH-Hal]^\oplus Hal^\ominus$, in which Hal is chlorine or bromine. The above reagents are usually manufactured in situ by treating a suitable N,N-di-lower alkylated amide, especially dimethylformamide, with a chlorinating or brominating agent, for example phosgene, carbonyl dibromide, oxalyl chloride, oxalyl bromide, thionyl bromide, phosphorus oxychloride, phosphorus oxybromide, phosphorus pentachloride or especially with phosphorus trichloride, phosphorus tribromide or thionyl chloride.

The above reaction is usually carried out in the presence of a solvent or diluent, and apart from the amide used as solvent and normally present in excess, usually dimethylformamide or alternatively dimethylacetamide, it is possible to use also ethers, for example tetrahydrofuran or dioxan, halogenated hydrocarbons, for example methylene chloride, or sulphoxides, for example dimethyl sulphoxide.

The chlorinating and brominating agents are normally added in quantities corresponding to two equivalents of the 3-hydroxy-3-cephem starting material. The reaction can be carried out, for example, by adding the chlorinating agent or brominating agent while cooling to a solution of the 3-hydroxy-3-cephem starting material in dimethylformamide and then leaving the reaction mixture to stand for a few hours at room temperature.

The chlorination or bromination may also be carried out by first of all mixing the chlorinating or brominating agent with the amide, especially dimethylformamide, and thus forming the halo-iminium halide, whereupon the solution of the 3-hydroxy-3-cephem starting material in the amide, especially in dimethylformamide, to which an additional solvent may be added, or in another solvent, for example tetrahydrofuran, is added.

The conversion of the free hydroxy group $R_1^a$ into fluorine can be carried out, for example, by treating with a reagent of the formula $F_3S-Am$, in which Am represents a di-substituted amino group; reagents of this type are described, inter alia, by Markovskij et al., Synthesis, 1973 volume, page 787. The group Am represents especially di-lower alkylamino, for example dimethylamino, diethylamino or diisopropylamino; lower alkylphenylamino, for example methylanilino; lower alkyleneamino, for example pyrrolidinyl or piperidino; oxa-lower alkyleneamino, for example morpholino; or optionally N-lower alkylated aza-lower alkyleneamino, for example 4-methylpiperazinyl.

The reaction is preferably carried out in a suitable inert solvent, such as an optionally chlorinated hydrocarbon, for example cyclopentane, cyclohexane, benzene, toluene, xylene, chlorobenzene, dichlorobenzene, pentane, hexane, chloroform and especially methylene chloride, or an ether, such as diethyl ether, tetrahydrofuran or, especially, dioxan, if necessary while cooling or heating, for example in a temperature range of from approximately −20° C. to approximately 80° C., preferably from approximately 0° C. to approximately 30° C., and/or in an inert gas atmosphere.

A sulphonated hydroxy group $R_1^a$ can be converted into fluorine by treating with an inorganic fluoride in the presence of a Crown ether. A sulphonated hydroxy group $R_1^a$ is especially lower alkylsulphonyloxy, especially methylsulphonyloxy, but may alternatively be arylsulphonyloxy in which aryl is preferably phenyl optionally substituted, for example by lower alkyl, such as methyl, halogen, for example bromine, or nitro, for example 4-methylphenylsulphonyloxy. An inorganic fluoride is especially a metal fluoride, wherein especially an alkali metal fluoride, for example sodium fluoride, or a heavy metal fluoride, for example silver fluoride, is used. The Crown ethers used together with the inorganic fluoride are optionally substituted 18-Crown-6-ethers, such as dicyclohexyl-18-Crown-6-ether.

The reaction is carried out in the presence of an inert solvent, especially a nitrile, for example acetonitrile or propionitrile, or a nitro-lower alkane, for example nitromethane or nitroethane, under substantially anhydrous conditions and, if necessary, while cooling, for example in a temperature range of from approximately −20° C. to approximately 20° C., preferably at approximately room temperature and optionally in an inert gas atmosphere. Corresponding processes have been described, for example, in German Offenlegungsschrift No. 2,636,962.

Process (j) (Etherification of the 3-hydroxy group)

The etherification of the free hydroxy group $R_1^a$ is carried out with a conventional etherifying agent introducing the desired hydrocarbon.

Suitable etherifying agents are, for example, corresponding diazo compounds, such as optionally substituted diazo-lower alkanes, for example diazomethane, diazo-n-butane or diphenyldiazomethane. These reagents are used in the presence of a suitable inert solvent, such as a lower aliphatic, cycloaliphatic or aromatic hydrocarbon, such as hexane, cyclohexane, benzene or toluene, a halogenated lower aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while heating slightly and also, if necessary, in a closed vessel and/or in an inert gas atmosphere, for example a nitrogen atmosphere.

Other suitable etherifying agents are esters of corresponding alcohols, especially those with strong inorganic or organic acids, such as mineral acids, for example hydrohalic acids, such as hydrochloric, hydrobromic or hydriodic acid, also sulphuric acid or halosulphonic acids, for example fluorosulphonic acid, or strong organic sulphonic acids, such as lower alkanesulphonic acids optionally substituted, for example by halogen, such as fluorine, or aromatic sulphonic acids, such as, for example, benzenesulphonic acids optionally substituted, for example by lower alkyl, such as methyl, by halogen, such as bromine, and/or by nitro, for example methanesulphonic acid, trifluoromethanesulphonic acid or p-toluenesulphonic acid, for example di-lower alkyl sulphates, such as dimethyl sulphate, also fluorosulphonic acid lower alkyl esters, for example fluorosulphonic acid methyl ester or optionally halogen-substituted methanesulphonic acid lower alkyl esters, for example trifluoromethanesulphonic acid methyl ester. They are normally used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture thereof. In this process suitable condensing agents are preferably used, such as alkali metal carbonates or bicarbonates, for example sodium or potassium carbonate or bicarbonate (usually together with a sulphate), or organic bases, such as, normally sterically hindered, tri-lower alkylamines, for example N,N-diisopropyl-N-ethylamine (preferably together with lower alkyl halosulphates or optionally halogen-substituted methanesulphonic acid lower alkyl esters), the process being carried out while cooling, at room temperature, or while heating, for example at temperatures of approximately −20° C. to approximately 50° C. and, if necessary, in a closed vessel and/or in an inert gas atmosphere, for example a nitrogen atmosphere.

The last-mentioned etherification reaction can be considerably accelerated by phase transfer catalysis (see E. V. Dehmlow, Angewandte Chemie 5, 187 (1974)). As phase transfer catalysts there may be used quaternary phosphonium salts and especially quaternary ammonium salts, such as optionally substituted tetraalkylammonium halides, for example tetrabutylammonium chloride, bromide or iodide, or also benzyl-triethylammonium chloride, in catalytic or up to equimolar quantities. Any one of the water-immiscible solvents may be used as the organic phase, for example one of the optionally halogenated, such as chlorinated, lower aliphatic, cycloaliphatic or aromatic hydrocarbons, such as trichloroethylene or tetrachloroethylene, tetrachloroethane, carbon tetrachloride, chlorobenzene or also toluene or xylene. The alkali metal carbonates or bicarbonates suitable as condensing agents, for example potassium or sodium carbonate or bicarbonate, alkali metal phosphates, for example potassium phosphate, and alkali metal hydroxides, for example sodium hydroxide, can, in the case of basesensitive compounds, be added to the reaction mixture titrimetrically, for example by means of an automatic titrating device, so that the pH value remains between approximately 7 and 8.5 during etherification.

Other etherifying agents are corresponding acetals, for example gem-lower alkoxy-lower alkanes, such as 2,2-dimethoxypropane, which are used in the presence of a strong organic sulphonic acid, such as p-toluenesulphonic acid, and a suitable solvent, such as a di-lower alkyl sulphoxide or lower alkylene sulphoxide, for example dimethyl sulphoxide; or orthoesters, for example orthoformic acid tri-lower alkyl esters, for example orthoformic acid triethyl ester, which are used in the presence of a strong organic sulphonic acid, such as p-toluenesulphonic acid, and a suitable solvent, such as an ether, for example dioxan. Other important etherifying agents are corresponding tri-$R_1^o$-oxonium salts (so-called Meerwein salts), in which $R_1^o$ represents the radical to be introduced, for example tri-lower alkyloxonium salts, especially the corresponding salts with complex fluorinecontaining acids, such as the corresponding tetrafluoroborates, hexafluorophosphates, hexafluoroantimonates or hexachloroantimonates, for example trimethyloxonium tetrafluoroborate. These etherifying agents are preferably used in an inert solvent, such as an ether or a halogenated lower aliphatic hydrocarbon, for example tetrahydrofuran or methylene chloride, or in a mixture thereof, if necessary in the presence of a base, such as an organic base, for example a preferably sterically hindered tri-lower alkylamine, for example N,N-diisopropyl-N-ethylamine, and while cooling, at room temperature or while heating slightly, for example at approximately −20° C. to approximately 50° C., if necessary in a closed vessel and/or in an inert gas atmosphere, for example a nitrogen atmosphere.

Other etherifying agents are, finally, corresponding 1-$R_1^o$-3-aryltriazene compounds, in which $R_1^o$ represents the radical to be introduced and aryl preferably represents an optionally substituted phenyl radical, for example lower alkylphenyl, such as 4-methylphenyl. Characteristic examples of triazene compounds of this type are 3-aryl1-lower alkyltriazenes, for example 3-(4-methylphenyl)-1-ethyltriazene. These reagents are usually used in the presence of inert solvents, such as optionally halogenated lower aliphatic hydrocarbons, ethers or mixtures thereof, and while cooling, at room temperature or preferably at elevated temperature, for example at approximately 20° C. to approximately 100° C. Corresponding processes have been described, for example, in German Offenlegungsschrift No. 2,636,962.

Process (k) (Decarbonylation)

The decarbonylation of the formyl group is carried out especially by treating with a carbon monoxideabsorbing heavy metal complex. Such heavy metal complexes are, especially, platinum metal complexes, a platinum metal meaning apart from platinum also iridium, rhodium, palladium and osmium.

Preferably bis-tri-substituted phosphine/platinum halides, bis-tri-substituted phosphine/carbonyliridium halides, tris-tri-substituted phosphine/iridium halides and especially tris-tri-substituted phosphine/rhodium halides are used, wherein the substituents of the phosphine are preferably lower alkyl, for example n-butyl, and especially phenyl, and the halides are especially chlorides. Phosphine/platinum metal complexes of this type that are capable of absorbing carbon monoxide by covalent bonding are, for example, bis-triphenylphosphine/platinum(II) chloride [(C$_6$H$_5$)$_3$P]$_2$PtCl$_2$ or bistriphenylphosphine/carbonyliridium(II) chloride [(C$_6$H$_5$)$_3$P]$_2$Ir(CO)Cl, and tris-triphenylphosphine/iridium(I) chloride [(C$_6$H$_5$)$_3$P]$_3$IrCl, but especially tris-triphenyl-phosphine/rhodium(I) chloride [(C$_6$H$_5$)$_3$P]$_3$RhCl.

If desired or necessary, the decarbonylation with the above-mentioned heavy metal complexes can be carried out in the presence of suitable catalysts or activating agents, for example Lewis acids, such as boron trifluoride (which can be used, for example, together with the bis-triphenylphosphine/platinum chloride), or a perchlorate, such as an alkali metal perchlorate, for example sodium perchlorate (which can be used, for example together with bis-triphenylphosphine/carbonyliridium chloride).

Preferably the process is carried out in the presence of inert solvents, especially hydrocarbons, such as aliphatic or cycloaliphatic or especially aromatic hydrocarbons, for example benzene, toluene or xylene, or halogenated, such as chlorinated, hydrocarbons, such as corresponding lower aliphatic or aromatic hydrocarbons, for example methylene chloride or chlorobenzene; ethers, such as lower aliphatic, lower aliphatic-aromatic or cyclic ethers, for example di-n-butyl ether, anisole or dioxan; nitriles, such as lower aliphatic nitriles, for example acetonitrile; or ketones, such as lower alkanones, for example acetone; or mixtures of such solvents. The reaction is carried out while cooling, at room temperature or while heating, for example at from approximately 10° C. to approximately 150° C., such as at from approximately 40° C. to approximately 120° C., and also, if necessary, in a closed vessel and/or in an inert gas atmosphere, for example in nitrogen or argon. Corresponding processes are described, for example, in German Offenlegungsschrift No. 2,151,567.

Process (I) (Exchange of a free or esterified hydroxy or optionally substituted amino group for hydrogen)

An esterified hydroxy group $R_1^a$ exchangeable for hydrogen is preferably a hydroxy group esterified by a strong organic or inorganic acid, such as a strong mineral acid, for example a hydrohalic acid, such as hydrochloric acid, or an organic sulphonic acid, such as a corresponding lower aliphatic or aromatic sulphonic acid. $R_1^a$ thus represents, for example, halogen, such as chlorine; lower alkylsulphonyloxy, for example methylsulphonyloxy or ethylsulphonyloxy; or arylsulphonyloxy, for example p-toluenesulphonyloxy. An amino radical $R_1^a$ that is optionally lower alkylated or cyclically disubstituted by lower alkylene or heterolower alkylene has the meanings given above for these radicals and is, for example, amino, methylamino, dimethylamino, diethylamino, pyrrolidinyl, piperidino or morpholino.

The replacement of the group $R_1^a$ in a compound of the formula XIV by hydrogen is carried out either in two stages by reducing the $C_3$–$C_4$-double bond and then splitting off $R_1^a$—H, or in one stage by splitting off $R_1^a$ directly by hydrogenation.

In the case of the two-stage exchange of $R_1^a$ for hydrogen, the reduction of the $C_3$–$C_4$-double bond in starting materials of the formula XIV is effected, for example by means of suitable hydride reducing agents. Suitable hydride reducing agents are especially complex metal hydrides, preferably corresponding boron hydrides, such as diborane or alkali metal borohydrides, for example sodium borohydride or lithium borohydride, also zinc borohydride, and organic alkali metal aluminium hydrides, such as tri-lower alkoxy alkali metal aluminium hydrides, for example tris-(tert.-butoxy)-lithium aluminium hydride, which are usually used in the presence of solvents, especially relatively polar solvents, such as alcohols, for example lower alkanols, such as methanol or ethanol, or ethers, such as aliphatic ethers, for example glycol and polyglycol ethers, such as ethylene glycol dimethyl ether or diethylene glycol dimethyl ether, or cyclic ethers, such as tetrahydrofuran or dioxan, or solvent mixtures, also of aqueous solvents, temperatures of approximately −20° C. to approximately 80° C. being used, if necessary in a closed vessel and/or in an inert gas atmosphere, for example a nitrogen atmosphere. If this reduction is carried out in the presence of suitable agents splitting off water, acid or amines, the desired 3-unsubstituted 3-cephem compound can be obtained directly. It is, however, also possible first of all to produce a 3-$R_1^a$-cepham compound, which can then be either isolated or further processed in situ. These 3-$R_1^a$-cepham starting compounds can also be obtained by other methods, for example by acylating a corresponding 7β-amino-3-$R_1^a$-cepham compound.

In the second process stage, the splitting off of the elements of a compound of the formula $R_1^a$-H, i.e. an acid, an amine or especially water, from a resulting 3-$R_1^a$-cepham compound, is carried out by treating preferably with suitable agents splitting off water, acids or amines. Water and amines are preferably split off by means of a strong organic carboxylic acid, such as a halo-lower alkanecarboxylic acid or sulphonic acid, for example p-toluenesulphonic acid or methanesulphonic acid. Water can also be split off especially by means of a suitable water-binding acid derivative, such as an anhydride or especially a halide, such as chloride, of an acid derived from phosphorus or sulphur, such as a corresponding inorganic acid, for example by means of phosphorus oxychloride or thionyl chloride, or a sulphonic acid, such as a lower aliphatic or aromatic sulphonic acid, for example by means of tosyl chloride or mesyl chloride. The operation is carried out preferably in the presence of a base, such as a tertiary amine, for example tri-lower alkylamine or heterocyclic amine, for example triethylamine or pyridine, or of a suitable ion exchanger, for example a sulphonated polystyrene ion exchanger charged with cations.

It is also possible to use dehydrating carbodiimide compounds for splitting off water, for example dicyclohexylcarbodiimide, or dehydrating carbonyl compounds disubstituted by way of nitrogen atoms, for example carbonyldiimidazole. These agents are in this case normally used in the presence of a solvent, such as an optionally halogenated lower aliphatic or aromatic hydrocarbon, for example benzene or toluene, or of a solvent mixture, it being possible to use simultaneously also as solvents suitable acidic agents, such as trifluoroacetic acid. If necessary, a water-adsorbing agent or a water separator is used in addition and the process is carried out while cooling or heating and/or in an inert gas atmosphere, for example a nitrogen atmosphere.

The process of splitting off in one stage by hydrogenation a group $R_1^a$ from a compound of the formula XIV is most successful if $R_1^a$ is halogen, such as chlorine, or an esterified hydroxy group, such as a hydroxy group esterified by a sulphonic acid, such as a lower aliphatic or aromatic sulphonic acid, for example methanesulphonic acid or toluenesulphonic acid. In this case hydrogenation is carried out preferably by means of metallic reducing agents ("nascent hydrogen") for example aluminium or especially zinc, or reducing metal compounds, for example corresponding metal alloys, amalgams or salts, for example aluminium amalgam, which are usually used in the presence of weak proton donors, such as water, alcohol (for example methanol or ethanol) or a lower aliphatic carboxylic acid, for example acetic acid or formic acid. Zinc is used, for example in the presence of glacial acetic acid or formic acid, an amalgam, for example in the presence of an aqueous inert organic solvent, such as an ether.

Certain esterified hydroxy groups $R_a^1$, especially sulphonyloxy, for example methylsulphonyloxy groups, can be split off in the form of an acid of the formula $R_1^a$-H also be adsorption, for example on silica gel, aluminium oxide, etc., and by elution (chromatography).

Preferably, in a compound of the formula XIV, an esterified hydroxy group $R_1^a$, such as a 3-halosulphonyloxy group, such as 3-chlorosulphonyloxy or 3-bromosulphonyloxy, a 3-toluenesulphonyloxy or a 3-methanesulphonyloxy group, can be replaced by hydrogen by treating with zinc in glacial acetic acid or formic acid and a tertiary amino group $R_1^a$, such as 3-morpholino or 3-pyrrolidinyl, can be replaced by hydrogen by treating with diborane and then with glacial acetic acid. Corresponding processes are described, for example in German Offenlegungsschrift No. 2,620,308.

The splitting off of $R_1^a$-H is normally carried out in the presence of a solvent. When using inorganic bases, the operation can be carried out in water, a watersoluble organic solvent, such as acetone or dioxan, or aqueous mixtures thereof and at a maximum pH of 9, and when using amines preferably also in an optionally halogenated, such as chlorinated, lower aliphatic, cycloaliphatic or aromatic hydrocarbon, such as methylene chloride, a lower alkanone, for example acetone, or ether, for example tetrahydrofuran or dioxan, or a corresponding solvent mixture, including an aqueous mixture, if necessary while cooling or heating and/or in an inert gas atmosphere, for example a nitrogen atmosphere.

In a resulting intermediate of the formula I in which at least one of the functional groups is in protected form, it is possible, in a customary manner known per se, to protect functional groups that are still not protected or to exchange protecting groups present for different protecting groups, for example by splitting off the protecting group present and introducing the desired different protecting group.

In a resulting intermediate of the formula I in which at least one of the functional groups is in protected form, a group $R_2$ present in the radical $R_1$ can be exchanged for a different group $R_2$ as indicated for this reaction in the case of the end products of the formula I.

Introduction of 7α-methoxy

In a resulting intermediate of the formula I in which $R_3$ is hydrogen and all functional groups are in protected form, the 7α-methoxy group $R_3$ can be introduced in a manner known per se, for example by treating the said intermediate in succession with an anion-forming agent, an N-halogenating agent and methanol.

A suitable anion-forming agent is especially an organometallic base, especially an alkali metal base and more especially an organolithium base. Such compounds are especially corresponding alcoholates, such as suitable lithium lower alkoxides, especially lithium methoxide, or corresponding metal hydrocarbon bases, such as lithium lower alkanes and phenyllithium. The reaction with the anion-forming organometallic base is usually carried out while cooling, for example at from approximately 0° C. to approximately −80° C., and in the presence of a suitable solvent or diluent, for example an ether, such as tetrahydrofuran, or, when using lithium methoxide, alternatively in the presence of methanol, and, if desired, in a closed vessel and/or in an inert gas atmosphere, for example a nitrogen atmosphere.

A sterically hindered organic hypohalite, especially hypochlorite, and more especially a corresponding aliphatic hypohalite, for example hypochlorite, such as a tert.-lower alkyl hypohalite, for example hypochlorite, is usually used as N-halogenating agent. More especially, the tert.-butyl hypochlorite is used and is reacted with the product of the anionisation reaction, which has not been isolated.

If there is an excess of the anion-forming base, especially lithium methoxide, the N-halogenated intermediate compound is converted under the reaction conditions and without being isolated into a 7-acyliminocephem compound and this is converted into a 7α-methoxycephem compound by adding methanol. If necessary, the elements of the hydrohalic acid, especially the hydrochloric acid, must be split off from the N-halogenated intermediate; this is carried out by the addition of a base that causes the splitting off of hydrogen halide, such as a suitable alkali metal lower alkoxide, for example lithium tert.-butoxide, this reaction usually taking place under the conditions of the reaction used for forming the anion and the N-halogen compound, it being possible to carry out the reaction in the presence of methanol and obtain the 7α-methoxycephem compound directly instead of the acylimino compound. The starting material is usually a compound of the formula I in which functional groups are in protected form; this compound is reacted with an excess of the anion-forming agent, for example lithium methoxide or phenyllithium, in the presence of methanol, then treated with the N-halogenating agent, for example tert.-butyl hypochlorite, and in this manner the desired compound of the formula I in which functional groups are protected is obtained directly. It is also possible to add the methanol subsequently, in which case the dehydrohalogenation and the addition of methanol can be carried out at slightly higher tempertures than the reactions for forming the anion and the N-halogen compound, for example at from approximately 0° C. to approximately −20° C., if necessary in a closed vessel and/or in an inert gas atmosphere, for example a nitrogen atmosphere.

In the case of the above reactions, which are carried out under basic conditions, 3-cephem compounds can be isomerised, optionally partially, to form 2-cephem compounds. A resulting 2-cephem compound or a mixture of a 2- and a 3-cephem compound can be isomerised in a manner known per se to form the desired 3-cephem compound.

Salt formation

Salts of compounds of the formula I having protected and salt-forming groups can be manufactured in a manner known per se, for example as indicated for the formation of salts of compounds of the formula I.

Salts can be converted in the usual manner into the free compounds; metal and ammonium salts can be converted, for example by treating with suitable acids, and acid addition salts for example by treating with a suitable basic agent.

Mixtures of isomers can be separated into the individual isomers in a manner known per se, for example by fractional crystallisation, chromatography, etc.

The process also includes those embodiments according to which compounds formed as intermediates are used as starting materials and the remaining process steps are carried out with these, or the process is interrupted at any stage; in addition, starting materials may be used in the form of derivatives or may be formed during the reaction.

Preferably, the starting materials and the reaction conditions are so chosen that the compounds mentioned above as being especially preferred are obtained.

Starting materials

The starting materials used in the process for the manufacture of the compounds of the present invention are known or, if new, can be manufactured in a manner known per se.

The starting compounds of the type of the formula II and also corresponding compounds having protected functional groups are known or can be manufactured in a manner known per se.

Compounds of the formula III in which the aminocarboxylic acid grouping HOOC—CH(NH₂)— and other functional groups optionally present in the grouping A and R₄ are in protected form, and their reactive functional acid derivatives are novel and the present invention relates to these as well as to the processes for their manufacture.

The invention accordingly relates also to a process for the manufacture of compounds of the formula

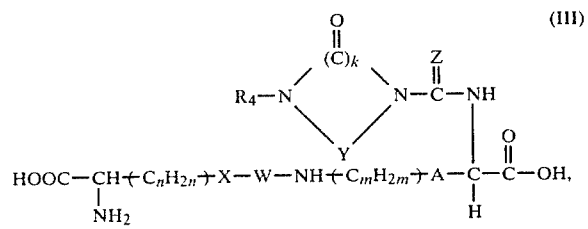

(III)

in which the aminocarboxylic acid grouping HOOC—CH(NH₂)— and other functional groups optionally present in the groupings A and R₄ are in protected form, and their reactive functional acid derivatives, characterised in that (a′) in a compound of the formula

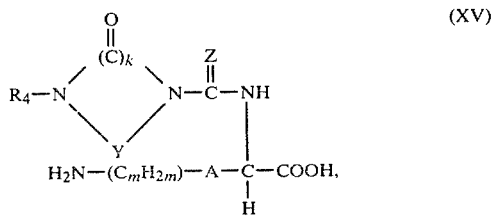

(XV)

in which the amino group may optionally be substituted by a group allowing acylation and in which the carboxyl group and other functional groups optionally present in the groupings A and R₄ may be in protected form, the amino group is acylated by treating with a reactive functional derivative of an acid of the formula

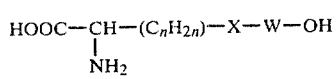

(V)

in which the aminocarboxylic acid grouping HOOC—CH(NH₂)— is in protected form, or, when X—W together represent a group —CO—, alternatively with a corresponding free acid, or with a salt thereof, or (b′) in a compound of the formula

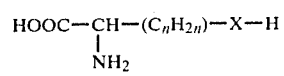

(VI)

in which X represents oxygen, sulphur or the group —NH— and in which the aminocarboxylic acid grouping HOOC—CH(NH₂)— is in protected form, the group —X—H is acylated with a reactive functional derivative of a compound of the formula

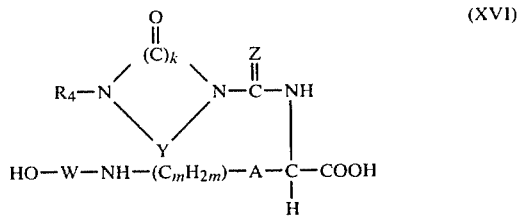

(XVI)

in which the carboxyl group and functional groups optionally present in the groupings A and R₄ may be in protected form, or (c′) in a compound of the formula

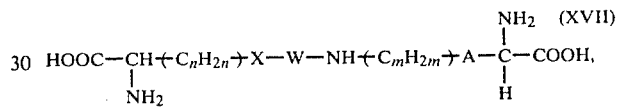

(XVII)

in which the aminocarboxylic acid grouping HOOC—CH(NH₂)— is in protected form, the amino group to be acylated is optionally substituted by a group allowing acylation and the carboxy group and other functional groups optionally present in the grouping A may be in protected form, the amino group is acylated by treating with an acylating agent introducing the corresponding acyl radical of a carbonic or thiocarbonic acid of the formula

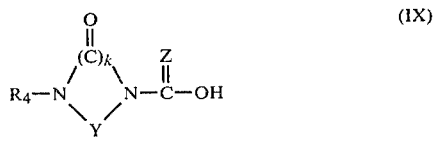

(IX)

in which functional groups optionally present in the radical R₄ may be in protected form, or (d′) a reactive derivative of a carbonic or thiocarbonic acid compound of the formula

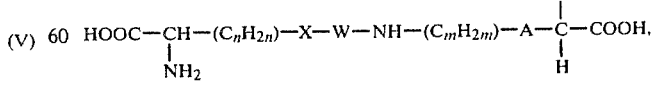

(XVIII)

in which the aminocarboxylic acid grouping HOOC—CH(NH₂)— is in protected form and in which the carboxyl group and other functional groups optionally present in the grouping A may be in protected form, is reacted with a secondary amide of the formula

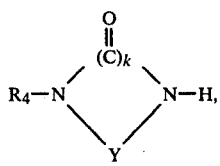

(XI)

in which functional groups optionally present in the radical $R_4$ may be protected and the secondary amido group is in a form allowing acylation, or (e') the acylation mentioned under (c') or (d') is carried out in situ by allowing an amino compound of the formula XVII and an amido compound of the formula XI, each with the meanings indicated above, to act simultaneously or in succession on a bivalent reactive derivative of carbonic or thiocarbonic acid, or (f') a compound of the formula

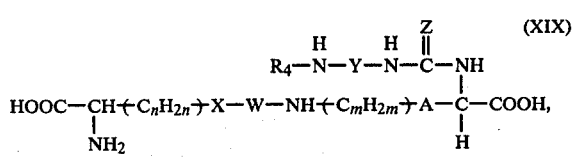

(XIX)

in which the aminocarboxylic acid grouping HOOC—CH(NH$_2$)— is in protected form and in which the carboxyl group and other functional groups optionally present in the grouping A may be in protected form and the secondary amino/amido groups later forming the piperazine ring are optionally substituted by groups allowing N-acylation, is diacylated with a bivalent acylating derivative of carbonic or oxalic acid with cyclisation, and, if desired, in a resulting compound of the formula III the protected carboxyl group is converted into a free carboxyl group or into a reactive functional derivative thereof.

The groups allowing acylation and the groups protecting the aminocarboxylic acid grouping HOOC—CH(NH$_2$)— and the protecting groups in the groupings A and $R_4$ are the same as those mentioned under the compounds of the formulae IV and I. The carboxy-protecting groups already mentioned can, per se, also be used for the intermediate protection of the carboxyl group in the compounds of the formula XV, XVI, XVII or XVIII but the carboxyl-protecting groups used for intermediate protection in the present acylation must differ from the other protecting groups, which are of necessity to remain in the compounds of the formula III, in the manner in which they are split off so that they can be split off selectively after the present acylation reactions. If, for example, a protecting group that can be split off by hydrogenolysis is used for the intermediate protection of the carboxyl group, such as one of the optionally substituted benzyl groups mentioned, for example the benzyl or p-nitrobenzyl group, then it must not be possible to split off the other protecting groups by hydrogenolysis; they may be, for example, the mentioned tert.-lower alkyl groups, such as tert.-butyl, or tert.-lower alkoxycarbonyl groups, such as tert.-butoxycarbonyl, that can be split off only by acidolysis.

Processes (a') to (f') are otherwise carried out analogously to processes (b) to (g).

In a resulting compound of the formula III having correspondingly protected functional groups, a protecting group can be split off, optionally selectively, or a functional group that has optionally become free during the acylation reaction can be protected.

Functional derivatives of compounds of the formula III which are reactive with respect to the free carboxyl group and permit the formation of the 7$\beta$-amide in process (a) and in which all the other functional groups are protected, i.e. the mentioned anhydrides, mixed anhydrides or activated esters, are manufactured in a manner known per se. For example, a mixed anhydride is obtained by reacting a compound of the formula III, in which functional groups apart from the carboxyl group to be reacted are protected, or a suitable salt, for example a metal salt, such as an alkali metal salt, or especially an ammonium salt, for example with ammonia or an organic amine, such as trilower alkylamine, for example triethylamine or 3-dimethylaminpropanol, or a cyclic amine, such as 4-methylmorpholine, of such an acid of the formula III with a suitable halogenating agent, for example with phosphorus pentachloride, thionyl chloride or oxalyl chloride, or with a halide of an optionally substituted lower alkanecarboxylic acid, for example trichloroacetyl chloride, or with a semi-ester of a carbonic acid semi-halide, for example ethyl chloroformate or isobutyl chloroformate. The activated esters are obtained, for example by reacting one of the mentioned salts of the acid of the formula III with a reactive derivative of a corresponding alcohol, for example with a halide, such as chloride, bromide or iodide, or with a sulphonyl ester, for example methanesulphonyl ester or p-toluenesulphonyl ester, or by reacting the free acid with the corresponding alcohol in the presence of a suitable condensation agent, such as one of the carbodiimide or carbonyl compounds mentioned in acylation (a), (b) or (g). The solvents and rection conditions are the same as those indicated for the acylation reaction.

Compounds of the formula IV in which the amino group may optionally be substituted by a group allowing acylation and in which the 4-carboxyl group and other functional groups optionally present in the radical $R_1$ and in the groupings A and $R_4$ may be in protected form, are novel. The invention relates also to these compounds and to the processes for their manufacture. In the novel compounds of the formula IV the indices m and k, A, $R_1$, $R_3$, Z and $R_4$ have the meanings indicated under formula I and the preferred meanings of the said symbols also correspond to the preferred meanings indicated under formula I. These novel compounds, in which the carboxyl group is optionally esterified in a form that can be split under physiological conditions, and their pharmaceutically acceptable salts also have antibiotic activity.

The said novel antibiotically active compounds of the formula IV may be used as antibacterial antibiotics. For example, they are effective in vitro against gram-positive and gram-negative micro-organisms, such as against gram-positive and gram-negative cocci, for example *Staphylococcus aureus*, Streptococcus spp. and Neisseria, in minimum doses of from approximately 0.01 to 32 $\mu$g/ml, and against gram-negative bacteria, such as enterobacteria, for example *Escherichia coli*, Proteus, Salmonella or Klebsiella, or against *Pseudomonas aeruginosa* or *Haemophilus influenzae*, in minimum doses of from approximately 0.05 to 64 $\mu$g/ml. In vivo, on subcutaneous administration to mice, they are effective, for example in the case of gram-positive infections, for example caused by *Staphylococcus aureus*, in the range of dose of from approximately 6 to 25 mg/kg, and in the case of gram-negative infections, for example caused by *Escherichia coli,* Proteus spp. or *Pseudomonas aeruginosa,* in the range of dose of from approximately 4 to 100 mg/kg.

The novel compounds of the formula IV can therefore be used accordingly, for example in the form of antibiotically active preparations, for the treatment of systemic infections caused by gram-positive or especially gram-negative bacteria and cocci, especially *Pseudomonas aeruginosa,* the minimum $ED_{50}$ in the case of subcutaneous injection being approximately 40 mg/kg.

Compounds of the formula IV in which the amino group and the other functional groups may optionally be substituted or protected as indicated and their salts can be manufactured by (a″) in a compound of the formula

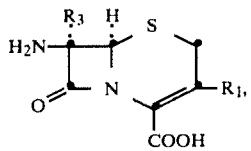
(II)

in which the amino group is optionally substituted by a group allowing acylation and in which the 4-carboxyl group and other functional groups optionally present in the radical $R_1$ may be in protected form, acylating the amino group by treating with an acid of the formula

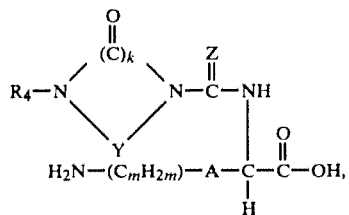
(XV)

in which the amino group and other functional groups optionally present in the groupings A and $R_4$ are in protected form, or with a reactive functional acid derivative or a salt thereof, or (b″) in a compound of the formula

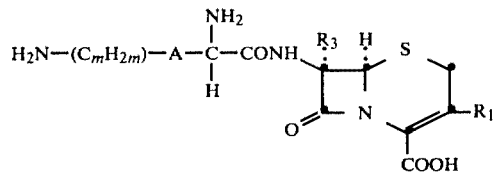
(XX)

in which the terminal amino group is in protected form, the amino group to be acylated is optionally substituted by a group allowing acylation and the 4-carboxyl group and other functional groups optionally present in the radical $R_1$ and in the grouping A may be in protected form, acylating the α-amino group by treating with an acylating agent introducing the corresponding acyl radical of a carbonic or thiocarbonic acid of the formula

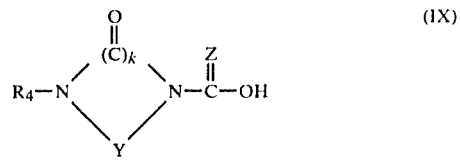
(IX)

in which functional groups optionally present in the radical $R_4$ may be in protected form, or (c″) reacting a reactive derivative of a carbonic or thiocarbonic acid compound of the formula

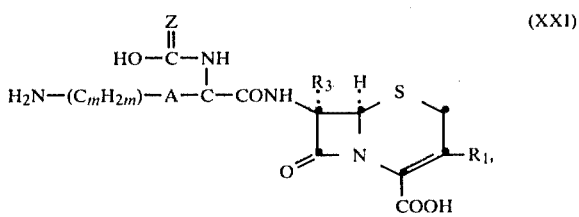
(XXI)

in which the terminal amino group is in protected form and in which the 4-carboxyl group and other functional groups optionally present in the radical $R_1$ and in the grouping A may be in protected form, with a secondary amide of the formula

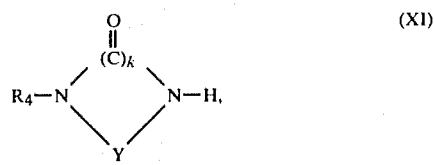
(XI)

in which functional groups optionally present in the radical $R_4$ may be protected and the secondary amido group is in a form allowing acylation, or (d″) carrying out in situ the acylation mentioned under (b″) or (c″) by allowing an amino compound of the formula XX and an amido compound of the formula XI, each with the meanings indicated above, to act simultaneously or in succession on a bivalent reactive derivative of carbonic or thiocarbonic acid, or (e″) diacylating a compound of the formula

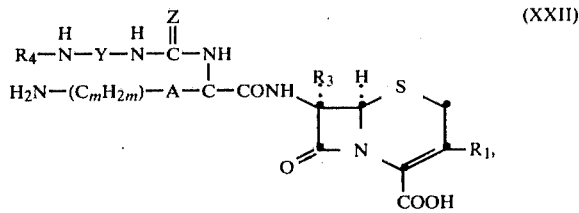
(XXII)

in which the terminal amino group is in protected form and in which the 4-carboxyl group and other functional groups optionally present in the radical $R_1$ and in the grouping A may be in protected form, and the secondary amino/amido groups later forming the diaza ring are optionally substituted by groups allowing N-acylation, with a bivalent acylating derivative of carbonic or oxalic acid with cyclisation, or (f″) isomerising a 2-cephem compound of the formula

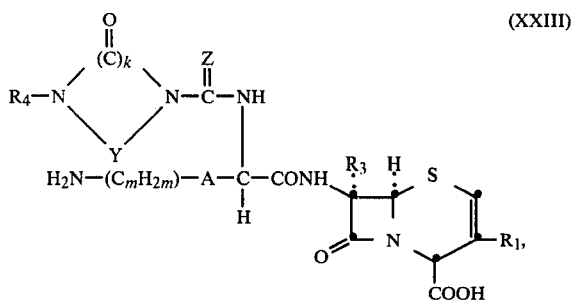

(XXIII)

in which functional groups are protected, to form the corresponding 3-cephem compound of the formula IV, or (g″) in a compound of the formula

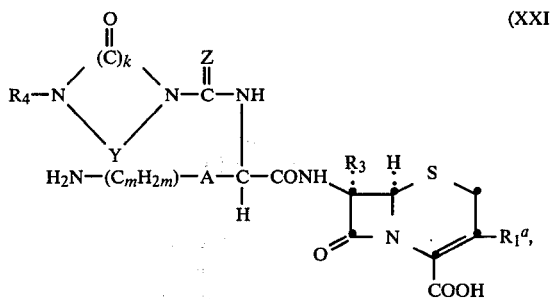

(XXIV)

in which $R_1{}^a$ is a free or sulphonated hydroxy group and in which other functional groups are protected, exchanging $R_1{}^a$ for halogen, or (h″) in a compound of the formula XXIV in which $R_1{}^a$ is a free hydroxy group and in which other functional groups are protected, etherifying the hydroxy group, or (i″) in a compound of the formula XXIV in which functional groups are protected and in which $R_1{}^a$ represents a formyl group, decarbonylating this in the presence of decarbonylation catalysts to form a compound of the formula I in which $R_1$ represents hydrogen, or (j″) in a compound of the formula XXIV in which $R_1{}^a$ represents free or esterified hydroxy or an optionally lower alkylated amino group or amino optionally cyclically disubstituted by lower alkylene or heterolower alkylene and in which functional groups are protected, replacing the group $R_1{}^a$ by hydrogen, and, if desired, in a resulting compound splitting off the protecting groups, or protecting functional groups that are still not protected, or exchanging a protecting group for a different protecting group and/or, if desired, in a radical $R_1$, exchanging a group $R_2$ for a different group $R_2$ and/or, if desired, converting a resulting compound in which $R_3$ is hydrogen into a compound in which $R_3$ is methoxy and/or, if desired, separating a resulting mixture of isomers into the individual isomers and/or, if desired, converting a resulting compound into a salt or a resulting salt into the free compound or into a different salt.

The functional groups present in the starting materials of the formulae II, XV and XX to XXIV can be protected by the protecting groups already mentioned under the compounds of the formula I. All reactive functional groups not participating in the reactions, but especially optionally present carboxyl, sulpho, amino, hydroxy and mercapto groups, are preferably protected.

The processes mentioned in processes (a″) to (j″) and the mentioned subsequent operations can be carried out in an analogous manner to processes (a) and (d) to (l) and the subsequent operations mentioned therein. The removal of protecting groups from protected compounds of the formula IV can be effected in the same manner as indicated for the removal of the same protecting groups from protected compounds of the formula I.

Acids of the formula V, reactive functional derivatives thereof, the preliminary stages of the formula $HOOC-CH(NH_2)-(C_nH_{2n})-X-H$ (VI) and correspondingly protected derivatives are known or can be manufactured according to methods known per se, for example in situ.

Reactive functional derivatives of acids of the formula VII in which the 4-carboxyl group and functional groups optionally present in the radical $R_1$ and in the groupings A and $R_4$ may be in protected form, are manufactured in a manner known per se from correspondingly protected compounds of the formula IV.

Compounds of the formulae VIII to XI and corresponding reactive functional and protected derivatives thereof are known or can be manufactured according to methods known per se.

Corresponding reactive functional and protected derivatives of compounds of the formula X can be manufactured, for example, from compounds of the formula VIII in which all functional groups are protected and the amino group to be acylated is optionally substituted in a form allowing acylation.

Protected compounds of the formula XII and their reactive derivatives are novel and the invention relates also to these as well as to the processes for their manufacture. They can be manufactured from compounds of the formula VIII or X by reacting with a diamine of the formula $R_4-NH-Y-NH_2$ or with a reactive derivative thereof of the formula $R_4-NH-Y-NH-C(=Z)-OH$, respectively, and optionally also from a compound of the formula VIII and a diamine of the formula $R_4-NH-Y-NH_2$ in the presence of a reactive derivative of carbonic or thiocarbonic acid.

The 2-cephem compounds of the formula XIII having protected functional groups are novel and the present invention relates to these also as well as to the processes for their manufacture. The compounds can be obtained from corresponding 3-cephem compounds by basic isomerisation or according to one of the processes suitable for the manufacture of compounds of the formula I, corresponding 2-cephem compounds being used as starting materials provided that the reactions are carried out under isomerising, basic conditions.

Compounds of the formula XIV in which $R_1{}^a$ has the meanings indicated and other functional groups are in protected form, are novel and the present invention relates to these also as well as to the processes for the manufacture. These compounds can be manufactured according to one of the processes (a) to (h) described for the manufacture of compounds of the formula I in which functional groups are protected, and in the starting compounds, for example of the formula XXIV, $R_1{}^a$ must, if necessary, be in protected form.

Compounds of the formula XV in which the amino group may optionally be substituted by a group allowing acylation and in which the carboxyl group and other functional groups optionally present in the groupings A and $R_4$ may be in protected form, and the derivatives thereof which are reactive with respect to the carboxyl group, are novel and the present invention relates to these also as well as to the processes for their manufacture.

These compounds can be manufactured, for example by (a''') in a compound of the formula

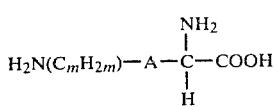

(XXV)

in which the terminal amino group is in protected form, the amino group to be acylated is optionally substituted by a group allowing acylation and the carboxyl group and other functional groups optionally present in the grouping A may be in protected form, acylating the α-amino group by treating with an acylating agent introducing the corresponding acyl radical of a carbonic or thiocarbonic acid of the formula

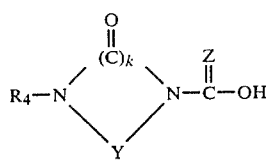

(IX)

in which functional groups optionally present in the radical $R_4$ may be in protected form, or (b''') reacting a reactive derivative of a carbonic or thiocarbonic acid compound of the formula

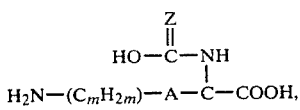

(XXVI)

in which the terminal amino group is in protected form and in which the carboxyl group and other functional groups optionally present in he grouping A may be in protected form, with a secondary amide of the formula

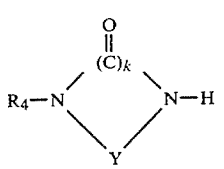

(XI)

in which functional groups optionally present in the radical $R_4$ may be protected and the secondary amido group is in a form allowing acylation, or (c''') carrying out in situ the acylation mentioned under (a''') or (b''') by allowing an amino compound of the formula XXV and an amido compound of the formula XI, each with the meanings indicated above, to act simultaneously or in succession on a bivalent reactive derivative of carbonic or thiocarbonic acid, or (d''') diacylating a compound of the formula

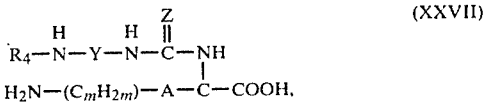

(XXVII)

in which the terminal amino group is in protected form and in which the carboxyl group and other functional groups optionally present in the grouping A may be in protected form and the secondary amino/amido groups later forming the diaza ring are optionally substituted by groups allowing N-acylation, with a bivalent acylating derivative of carbonic or oxalic acid with cyclisation, and, if desired, in a resulting compound of the formula XIV converting the protected carboxyl group into a free carboxyl group or into a reactive functional derivative thereof.

The groups allowing acylation and the protecting groups in the groupings A and $R_4$ are the same as those mentioned under the compounds of the formulae II or IV and I. For the intermediate protection of the carboxyl group in the compounds of the formulae XXV, XXVI and XXVII the carboxyl-protecting groups already mentioned can, per se, also be used but the carboxyl-protecting groups used for intermediate protection in the present acylation must differ from the other protecting groups, which are of necessity to remain in the compounds of the formula XV, in the manner in which they are split off so that they can be split off selectively after the present acylation reactions. If, for example, for the intermediate protection of the carboxyl group a protecting group is used that can be split off by hydrogenolysis, such as one of the optionally substituted benzyl groups mentioned, for example the benzyl or p-nitrobenzyl group, then it must not be possible to split off the other protecting groups by hydrogenolysis; they may be, for example, the mentioned tert.-lower alkyl groups, such as tert.-butyl, or tert.-lower alkoxycarbonyl groups, such as tert.-butoxycarbonyl, that can be split off only by acidolysis.

Processes (a''') to (d''') are otherwise carried out analogously to processes (d) to (g) or (b'') to (e'').

In a resulting compound of the formula XV having correspondingly protected functional groups a protecting group can be split off, optionally selectively, or a functional group that has optionally become free during the acylation reaction, can be protected.

Functional derivatives of compounds of the formula XV that are reactive with respect to the carboxyl group and that permit the 7β-amide formation in process (a'') and in which all other functional groups are protected, are the same as the anhydrides or activated esters mentioned under formula III and can be manufactured analogously to these.

Compounds of the formula XVI in which the group HO—W— and functional groups optionally present in the groupings A and $R_4$ are in protected form and in which the group —COOH is optionally in reactive form, can be manufactured from compounds of the formula XV by introducing the group HO—W— or alternatively they can be manufactured analogously to processes (a''') to (d'''), the amino group in the starting materials being replaced by the protected group HO—W—NH—.

Compounds of the formulae XVII and XVIII and their protected and reactive derivatives are known or can be manufactured in a manner known per se.

Compounds of the formula XIX and their protected and reactive derivatives are novel. They can be manufactured by acylating compounds of the formula XVII or amidating compounds of the formula XVIII, the starting compounds being used in protected form.

Compounds of the formulae XX and XXI and their protected derivatives and derivatives allowing acylation are known or can be manufactured in a manner known per se, for example by acylating compounds of the formula II with the acyl radical of a compound of the formula XXV or XXVI with corresponding protection of functional groups.

Compounds of the formula XXII and their protected derivatives and derivatives allowing acylation are novel. They can be manufactured in a manner known per se, for example by treating a diamine of the formula $R_4-NH-Y-NH_2$ in which the secondary amino group is in protected form with an acylating derivative of a compound of the formula XXI, or by treating a compound of the formula XX with an acylating derivative of a compound of the formula $R_4-NH-Y-NH-C(=Z)-OH$, wherein, in the starting materials, groups not participating in the acylation reaction are in protected form and the amino groups to be acylated are optionally in a form allowing acylation.

Compounds of the formula XXIII in which the amino group may optionally be substituted by a group allowing acylation and in which the 4-carboxyl group and other functional groups optionally present in the radical $R_1$ and in the groupings A and $R_4$ may be in protected form, are also novel. They can be obtained analogously to the process for the manufacture of corresponding 3-cephem compounds of the formula IV, for example according to one of processes (a'') to (j'') if either corresponding 2-cephem compounds are used as starting materials or the processes are carried out under basic conditions, or by isomerising a 3-cephem compound of the formula IV.

Compounds of the formula XXIV in which the amino group may optionally be substituted by a group allowing acylation and in which the 4-carboxyl group and other functional groups optionally present in he radical $R_1$ and in the groupings A and $R_4$ may be in protected form, are novel. They can be manufactured analogously to the process for the manufacture of compounds of the formula IV, for example according to one of processes (a'') to (f''), the radical $R_1$ in the starting materials of the formulae II, XX, XXI, XXII or XXIII being replaced by one of the inert groups $R_1{}^a$ or by a protected hydroxy group $R_1{}^a$.

Compounds of the formulae XXV to XXVII and protected and reactive derivatives thereof are known or can be manufactured in a manner known per se.

The pharmacologically acceptable compounds of the present invention can be used, for example, for the manufacture of pharmaceutical preparations that contain an effective quantity of the active substance together or in admixture with inorganic or organic, solid or liquid pharmaceutically acceptable carriers that are preferably suitable for parenteral administration.

The pharmacologically active compounds of the present invention are preferably used in the form of injectable, for example intravenously or subcutaneously, administrable preparations or in the form of infusion solutions. Such solutions are preferably isotonic aqueous solutions or suspensions, it being possible to manufacture these before use, for example from lyophilised preparations that contain the active substance alone or together with a carrier, for example mannitol. The pharmaceutical preparations may be sterilised and/or contain adjuncts, for example preservatives, stabilisers, wetting agents and/or emulsifiers, agents imparting solubility, salts for regulating the osomotic pressure and/or buffers. The present pharmaceutical preparations which may, if desired, contain other pharmacologically valuable substances, are manufactured in a manner known per se, for example by means of conventional dissolving or lyophilising processes, and contain from 0.1% to 100%, especially from approximately 1% to approximately 50%, and in the case of lyophilisates up to 100%, of the active substance. Depending on the type of infection and the condition of the infected organism daily doses of from approximately 0.5 g to approximately 5 g s.c. are used for the treatment of warm-blooded animals weighing approximately 70 kg.

The following Examples illustrate the invention; temperatures are indicated in degrees Centigrade.

The following abbreviations are use in the Examples:
BOC: tert.-butoxycarbonyl
m.p.: melting point
IR: infra-red spectrum; the numbers indicate the position of the absorption bands in $cm^{-1}$,
UV: ultra-violet spectrum; the numbers in front of the brackets indicate the position of the absorption maxima in nm; the numbers in brackets indicate the $\epsilon$ value of the maximum.

EXAMPLE 1

154 g of (R,S)-4-aminomandelic acid are made into a slurry with 850 ml of 1N aqueous NaOH, a large portion of the acid dissolving. The pH is adjusted to 7.5 with 2N aqueous NaOH by means of a titrator. Once all of the starting material has dissolved, 300 ml of di-tert.-butyl carbonate in 800 ml of dioxan are added and the mixture is stirred for 4 hours at room temperature, the pH being maintained constant at 7.5 by adding 2N aqueous NaOH by means of the titrator. The mixture is then taken up in ethyl acetate, washed twice with water, and the aqueous phases are combined and adjusted to a pH of 3 at 5° with concentrated aqueous hydrochloric acid. Extraction with ethyl acetate is then immediately carried out, followed by washing neutral with saturated aqueous NaCl solution, drying over $Na_2SO_4$ and concentrating by evaporation. Crystallisation of the crude product once from methanol/ethyl acetate/hexane yields (R,S)-4-(BOC-amino)-mandelic acid having a melting point of 137°–139° C. IR: 3520, 3420, 1725 (wide), 1615, 1595, 1520 $cm^{-1}$ ($CH_2Cl_2$). UV: 247 nm (22000) in $C_2H_5OH$.

EXAMPLE 2

A solution of 300 g of diphenyldiazomethane in 500 ml of $CH_2Cl_2$ is added dropwise in the course of 1½ hours at 5°, while stirring, to a solution of 168 g of (R,S)-4-(BOC-amino)-mandelic acid in 500 ml of methanol and stirring is continued at the same temperature for a further 1½ hours. The reaction mixture is concentrated in vacuo at room temperature to 400 ml and 500 ml of ethyl acetate are added. The solution is rendered colourless by dropwise addition of acetic acid, diluted with a further amount of ethyl acetate and washed in succession with saturated aqueous solutions of $NaHCO_3$ (until basic) and NaCl (until neutral). The solution is then dried over $Na_2SO_4$ and concentrated by evaporation in vacuo, and the resulting crude product is crystallised once from toluene. (R,S)-4-(BOC-amino)-mandelic acid diphenylmethyl ester having a melting point of 168° C. is obtained. IR: 3500, 3370, 1720, 1620, 1605, 1535 cm$^{-1}$ (Nujol). UV: 244 nm (20400) in C$_2$H$_5$OH.

EXAMPLE 3

53 ml of an 8N solution of CrO$_3$ in 8N aqueous H$_2$SO$_4$ are added dropwise in the course of 3 minutes at 0°, while stirring, to a solution of 53 g of (R,S)-4-(BOC-amino)-mandelic acid diphenylmethyl ester in 350 ml of acetone. The mixture is stirred for a further 10 minutes at 0° and then, while stirring, 2 litres of water are added and the reaction product crystallises. The crystals are filtered with suction, washed with a large amount of water (until the washing water is neutral and colourless) and dried to constant weight at 50° in a water jet vacuum. The resulting crude product is recrystallised once from acetone/hexane, yielding 2-(4-BOC-aminophenyl)-glyoxylic acid diphenylmethyl ester having a metling point of 126°-127° C. IR: 3400, 1735, 1678, 1602, 1582, 1520, 1500 cm$^{-1}$ (CH$_2$Cl$_2$).
UV: 310 nm (24750) in C$_2$H$_5$OH.

EXAMPLE 4

27 g of hydroxylamine hydrochloride are triturated well in a mortar with 50 g of sodium acetate trihydrate. The hydroxylamine liberated is leached out with 900 ml of ethanol and the solution is filtered through a glass suction filter to remove undissolved solid materials. 100 g of 2-(4-BOC-aminophenyl)-glyoxylic acid diphenylmethyl ester are added to the resulting hydroxylamine solution and the mixture is boiled under reflux for 1 hour, resulting in a clear solution. The solution is then concentrated to a volume of approximately 500 ml (until crystallisation commences), precipitated with 1 l of water, left for 2 hours at 4° C., filtered with suction and washed with water, and the crystals are dried in vacuo at 50° C. to constant weight. Recrystallisation once of the crude product yields 2-(4-BOC-aminophenyl)-2-hydroxyiminoacetic acid diphenylmethyl ester having a melting point of 185° C. (decomposition). IR: 3330 (shoulder), 3300, 1720, 1685, 1605, 1595, 1538 cm$^{-1}$ (Nujol). According to thin layer chromatogram in a system of toluene/ethyl acetate (1:1) and NMR spectrum there is present a syn-anti mixture of the oximes.

EXAMPLE 5

50 g of 2-(4-BOC-aminophenyl)-2-hydroxyiminoacetic acid diphenylmethyl ester are boiled under reflux in a mixture of 1660 ml of methanol and 250 ml of 2N aqueous NaOH for 1½ hours under nitrogen. The reaction mixture is concentrated to 300 ml, diluted with ethyl acetate and washed three times with water. The aqueous washings are combined, cooled to 0° C. and adjusted to a pH of 3 with 2N aqueous hydrochloric acid. Extraction is carried out with ethyl acetate and the organic phase is washed neutral with saturated aqueous NaCl solution, dried over Na$_2$SO$_4$ and concentrated by evaporation in vacuo. 250 ml of water are mixed with the evaporation residue and the pH is adjusted to 7 with 2N aqueous sodium hydroxide solution. The aqueous solution is then extracted with ethyl acetate, the organic phase is washed three times with water, the aqueous washings are combined and filtered through sand, the filtrate is concentrated in vacuo to approximately 50 ml and the product is precipitated by adding 150 ml of ethanol and 500 ml of ether. After filtering off and drying, 2-(4-BOC-aminophenyl)-2-hydroxyiminoacetic acid sodium salt (syn-anti mixture) is obtained.

EXAMPLE 6

70.45 g of 2-(4-BOC-aminophenyl)-2-hydroxyiminoacetic acid sodium salt are exhaustively hydrogenated (room temperature, normal pressure) in 2 l of water in the presence of 15 g of 10% Pd/C catalyst. The catalyst is filtered off, washed with water and the filtrate is concentrated in vacuo to a volume of 1 litre. The pH is then adjusted to 4 with 2N aqueous hydrochloric acid, the mixture is left for 15 minutes at room temperature and the precipitated product is then filtered off, washed twice with a little water and once with ethanol and dried at 50° C. in a water jet vacuum. (R,S)-2-(4-BOC-aminophenyl)-glycine having a melting point of 270° C. (decomposition) is obtained. IR: 3370, 3250–2200 (wide), 1700, 1620, 1595, 1535 (Nujol).

EXAMPLE 7

17.5 g of (R,S)-2-(4-BOC-aminophenyl)-glycine are made into a slurry with 250 ml of tetrahydrofuran, 19.3 ml of bis(trimethylsilyl)acetamide are added and the mixture is stirred at room temperature for 70 minutes under nitrogen, a further 19.3 ml of bis(trimethylsilyl)acetamide being added after 40 minutes. 7.3 ml of N-methylmorpholine and 10.72 g of 2-imidazolidone-1-carbonyl chloride are then added in succession. The reaction mixture is stirred for a further 5 hours at room temperature under nitrogen and then poured into water. The pH is adjusted to 3 with 1N aqueous hydrochloric acid, the mixture is extracted with ethyl acetate, and the organic phase is washed three times with saturated aqueous NaCl solution, dried over sodium sulphate and concentrated by evaporation in vacuo. The resulting amorphous (R,S)-2-(4-BOC-aminophenyl)-2-(2-imidazolidone-1-carboxamido)-acetic acid is further processed without purification. IR: 3430, 3300 partly covered by 3500–2200 (wide), 1740–1660 (wide), 1610, 1595, 1520 cm$^{-1}$ (CH$_2$Cl$_2$).

EXAMPLE 8

(R,S)-2-(4-BOC-aminophenyl)-2-(3-methanesulphonyl-2-imidazolidone-1-carboxamido)-acetic acid, which is further processed without purification, is produced in a manner analogous to that in the preceding Example from 15 g of (R,S)-2-(4-BOC-aminophenyl)-glycine and 21.58 g of 3-methanesulphonyl-3-imidazolidone-1-carbonyl chloride.

EXAMPLE 9

(R,S)-2-(4-BOC-aminophenyl)-2-(4-ethyl-2,3-dioxopiperazine-1-carboxamido)-acetic acid, which is further processed without purification, is produced in a manner analogous to that in the two preceding Examples from (R,S)-2-(4-BOC-aminophenyl)-glycine and 25.3 g of 2,3-dioxo-4-ethylpiperazine-1-carbonyl chloride.

EXAMPLE 10

12.7 g of (R,S)-2-(4BOC-aminophenyl)-2-(2-imidazolidone-1-carboxamido)-acetic acid are dissolved in 100 ml of tetrahydrofuran and cooled to −20° C., and 3.85 ml of N-methylmorpholine and 3.6 ml of chloroformic acid isobutyl ester are added in succession. The mixture is stirred for 3 hours at −20° C., the temperature is then lowered to −40° C. 13.5 g of 3-[(1-methyl-1H-tetrazol-5-yl)-thiomethyl]-7β-amino-3-cephem-4- carboxylic acid diphenylmethyl ester in solid form are added and the mixture is stirred for 10 minutes at −40° C. and for 2½ hours at 0° C. and then worked up as follows: The reaction mixture is taken up in ethyl acetate and washed in succession with 1N aqueous hydrochloric acid, saturated aqueous NaCl solution and saturated aqueous NaHCO$_3$ solution and again with NaCl solution until neutral. The organic phase is dried over Na$_2$SO$_4$ and concentrated by evaporation in vacuo and the residue is chromatographed over 900 g of silica gel (eluant: toluene/ethyl acetate (1:1); fraction size 500 ml). 3-[(1-methyl-1H-tetrazol-5-yl)-thiomethyl]-7β-[(2R)-(4-BOC-aminophenyl)-2-(2-imidazolidone-1-carboxamido)-acetamido]-3-cephem-4-carboxylic acid diphenylmethyl ester is obtained from fractions 18–50 by reprecipitation from CH$_2$Cl$_2$/diethyl ether/hexane. $[\alpha]_D^{20} = -108° \pm 1°$ (0.814% in CHCl$_3$).

IR: 3440, 3300, 1792, 1725, 1705, 1690, 1670, 1620, 1600, 1515 cm$^{-1}$ (CH$_2$Cl$_2$). UV: 246 (29600, EtOH).

Later fractions consist of a binary mixture of the above compound with the corresponding 2S-derivative.

EXAMPLE 11

5 g of 3-[(1-methyl-1H-tetrazol-5-yl)-thiomethyl]-7β-[(2R)-2-(4-BOC-aminophenyl)-2-(2-imidazolidone-1-carboxamido)-acetamido]-3-cephem-4-carboxylic acid diphenylmethyl ester are stirred at room temperature for 2½ hours with 2.3 g of p-toluenesulphonic acid monohydrate in 50 ml of acetonitrile. After adding 500 ml of ether, filtering the precipitate with suction, washing with 300 ml of ether and drying in vacuo, 3-[(1-methyl-1H-tetrazol-5-yl)-thiomethyl]-7β-[(2R)-2-(4-aminophenyl)-2-(2-imidazolidone-1-carboxamido)-acetamido]-3-cephem-4-carboxylic acid diphenylmethyl ester p-toluenesulphonate is obtained $[\alpha]_D^{20} = -37° \pm 1°$ (0.758% in CH$_3$OH).

IR: 3420, 3320, 2640, 1785, 1730, 1662, 1540, 1520, 1470, 1385 cm$^{-1}$ (Nujol). UV: 250 (16200, EtOH).

EXAMPLE 12

5.01 g of 3-[(1-methyl-1H-tetrazol-5-yl)-thiomethyl]-7β-[(2R)-2-(4-aminophenyl)-2-(2-imidazolidone-1-carboxamido)-acetamido]-3-cephem-4-carboxylic acid diphenylmethyl ester p-toluenesulphonate are stirred at 0° for 1 hour in 150 ml of tetrahydrofuran together with 1.04 ml of pyridine and 4.15 g of (2R)-2-BOC-amino-2-diphenylmethoxycarbonylethoxycarbonyl chloride. The mixture is taken up in ethyl acetate, washed in succession with 1N aqueous hydrochloric acid, saturated aqueous NaCl solution and saturated aqueous NaHCO$_3$ solution and again with NaCl solution until neutral. The crude product obtained by drying over sodium sulphate and concentrating by evaporation is chromatographed over 400 g of silica gel (eluant: toluene/ethyl acetate (1:1); 500 ml fractions). Combination of the product-containing fractions yields 3-[(1-methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester. $[\alpha]_D^{20} = -19° \pm 1°$ (1.006% in DMSO). IR: 3420, 3330, 1785, 1752, 1725, 1703, 1690, 1620, 1605, 1527, 1487 cm$^{-1}$ (Nujol). UV: 246 (30100; CH$_3$OH).

EXAMPLE 13

1.2 g of 3-[(1-methyl-1H-tetrazol-5-yl)-thiomethyl]-7β-[(2R)-2-(4-BOC-aminophenyl)-2-(2-imidazolidone-1-carboxamido)-acetamido]-3-cephem-4-carboxylic acid diphenylmethyl ester are dissolved in a mixture of 3.24 ml of CH$_2$Cl$_2$ and 1.164 ml of anisole at room temperature. 15.36 ml of trifluoroacetic acid, cooled to 0°, are added to the solution and the mixture is stirred for 15 minutes without external cooling. After adding 250 ml of hexane/ether (2:1), stirring is carried out for 5 minutes and the precipitate is filtered with suction and then washed with 200 ml of a hexane/ether mixture (2:1). The filter residue is dissolved in 100 ml of methanol, 100 ml of water are added, the pH is adjusted to 7 by the addition of 1N aqueous sodium hydroxide solution and extraction is carried out with ethyl acetate. The organic phase is washed three times with water. All of the aqueous phases are combined and concentrated in vacuo to approximately 10 ml. The addition of approximately 300 ml of ethanol results in a white precipitate, which is filtered with suction, washed twice with ethanol and twice with ether and dried in vacuo. The product is 3-[(1-methyl-1H-tetrazol-5-yl)-thiomethyl]-7β-[(2R)-2-(4-aminophenyl)-2-(2-imidazolidone-1-carboxamido)-acetamido]-3-cephem-4-carboxylic acid sodium salt. Decomposition from 170° C. $[\alpha]_D^{20} = -17° \pm 1°$ (0.995% in DMSO). IR: 3310, 1770, 1725 (wide), 1665, 1612, 1520 cm$^{-1}$ (Nujol). UV: 245 (16550; H$_2$O).

EXAMPLE 14

2.2 g of 3-[(1-methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester are reacted in 3.75 ml of CH$_2$Cl$_2$ and 1.35 ml of anisole with 17.7 ml of trifluoroacetic acid and worked up analogously to the manner described in Example 13. 3-[(1-methyl-1H-tetrazol-5-yl)-thiomethyl]-7β-{(2R)-2-[4-((2R)-2-amino-2-carboxyethoxycarbonylamino)-phenyl]-2-(2-imidazolidone-1-carboxamido)-acetamido}-3-cephem-4-carboxylic acid sodium salt is obtained. Decomposition from 175° C. $[\alpha]_D^{20} = -3° \pm 1°$ (0.775% in H$_2$O). IR: 3450 (shoulder), 3300, 1770, 1730, 1655, 1560, 1537 cm$^{-1}$ (Nujol). UV: 244 (25750; H$_2$O).

EXAMPLE 15

In the manner described in Example 10, 9.17 g of (R,S)-2-(4-BOC-aminophenyl)-2-(3-methanesulphonyl-2-imidazolidone-1-carboxamido)-acetic acid and 8 g of 3-[(1-methyl-1H-tetrazol-5-yl)-thiomethyl]-7β-amino-3-cephem-4-carboxylic acid diphenylmethyl ester are reacted with 2.155 ml of chloroformic acid isobutyl ester in 2.31 ml of N-methylmorpholine and 100 ml of tetrahydrofuran and worked up. Filtration of the crude product over 400 g of silica gel in ethyl acetate and then reprecipitation of the eluates from CH$_2$Cl$_2$/ether/hexane yields 3-[(1-methyl-1H-tetrazol-5-yl)-thiomethyl]-7β-[(2R,S)-2-(4-BOC-aminophenyl)-2-(3-methanesulphonyl-2-imidazolidone-1-carboxamido)-acetamido]-3-cephem-4-carboxylic acid diphenylmethyl ester (epimeric mixture).

IR: 3400, 3300, 1785, 1735, 1720, 1705, 1690, 1670, 1605, 1515, 1355, 1165 (CH$_2$Cl$_2$). UV: 248 (18100; EtOH).

EXAMPLE 16

In the manner described in Example 11, 7.86 g of 3-[(1-methyl-1H-tetrazol-5-yl)-thiomethyl]-7β-[(2R,S)-2-(4-BOC-aminophenyl)-2-(3-methanesulphonyl-2-imidazolidone-1-carboxamido)-acetamido]-3-cephem-4-carboxylic acid diphenylmethyl ester are reacted with 3.2 g of p-toluenesulphonic acid monohydrate in 70 ml of acetonitrile and worked up. 3-[(1-methyl-1H-tetrazol-5-yl)-thiomethyl]-7β-[(2R,S)-2-(4-aminophenyl)-2-(3-methanesulphonyl-2-imidazolidone-1-carboxamido)-acetamido]-3-cephem-4-carboxylic acid diphenylmethyl ester p-toluenesulphonate is obtained. IR: 3450 (shoulder), 3320, 2620 (shoulder), 1780, 1740, 1705 (shoulder), 1693 (shoulder), 1670, 1630, 1600 (shoulder), 1530, 1512 cm$^{-1}$ (Nujol). UV: 250 (16200; EtOH).

EXAMPLE 17

In the manner described in Example 12, 7.3 g of 3-[(1-methyl-1H-tetrazol-5-yl)-thiomethyl]-7β-[(2R,S)-2-(4-aminophenyl)-2-(3-methanesulphonyl-2-imidazolidone-1-carboxamido)-acetamido]-3-cephem-4-carboxylic acid diphenylmethyl ester p-toluenesulphonate are reacted with 6.05 g of (2R)-2-BOC-amino-2-diphenylmethoxycarbonylethoxycarbonyl chloride and 1.52 ml of pyridine in 150 ml of tetrahydrofuran and worked up. The resulting crude product is chromatographed over 400 g of silica gel (fraction size 500 ml). Elution is carried out as follows: fractions 1–24 with toluene/ethyl acetate mixture (2:1), fractions 25–31 with toluene/ethyl acetate mixture (1:1) and fractions 32–36 with ethyl acetate. Fractions 10–16 are concentrated by evaporation and reprecipitated from CH$_2$Cl$_2$/ether/hexane, yielding 3-[(1-methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(3-methanesulphonyl-2-imidazolidone-1-carboxamido)-acetamido}-3-cephem-4-carboxylic acid diphenylmethyl ester. Decomposition from 140° C. [α]$_D^{20}$ = −9° ± 1° (0.860% in DMSO). IR: 3330, 1790, 1735 (wide), 1680, 1610, 1605, 1530, 1382, 1170 cm$^{-1}$ (Nujol). UV: 246 (29200; EtOH).

3-[(1H-methyl-1H-tetrazol-5-yl)-thiomethyl]-7β-{(2S)-2-[4-((2R)-2-BOC-amino-2-diphenylmethoxycarbonylethoxycarbonylamino)-phenyl]-2-(3-methanesulphonyl-2-imidazolidone-1-carboxamido)-acetamido}-3-cephem-4-carboxylic acid diphenylmethyl ester is obtained in an analogous manner from fractions 29–32. Decomposition from 150°. [α]$_D^{20}$ = +16° ± 1° (0.681% in DMSO).

IR: 3330, 1790, 1738, 1720 (shoulder), 1700 (shoulder), 1683 (shoulder), 1615, 1605, 1533, 1380, 1170 cm$^{-1}$ (Nujol). UV: 246 (28500; EtOH).

EXAMPLE 18

In the manner described in Example 13, 1.2 g of 3-[(1-methyl-1H-tetrazol-5-yl)-thiomethyl]-7β-[(2R,S)-2-(4-BOC-aminophenyl)-2-(3-methanesulphonyl-2-imidazolidone-1-carboxamido)-acetamido]-3-cephem-4-carboxylic acid diphenylmethyl ester are reacted in 3.24 ml of CH$_2$Cl$_2$ and 1.164 ml of anisole with 15.4 ml of trifluoroacetic acid and worked up. 3-[(1-Methyl-1H-tetrazol-5-yl)-thiomethyl]-7β-[(2R,S)-2-(4-aminophenyl)-2-(3-methanesulphonyl-2-imidazolidone-1-carboxamido)-acetamido]-3-cephem-4-carboxylic acid sodium salt (epimeric mixture) is obtained. Decomposition from 170°. [α]$_D^{20}$ = +17° ± 1° (0.686% in H$_2$O). IR: 3380, 1770, 1740, 1680, 1620, 1522, 1383, 1170 cm$^{-1}$ (Nujol).

UV: 246 (18300; H$_2$O).

EXAMPLE 19

1.2 g of 3-[(1-methyl-1H-tetrazol-5-yl)-thiomethyl]-7β-{(2R)-2-[4-((2R)-2-BOC-amino-2-diphenyl-methoxycarbonylethoxycarbonylamino)-phenyl]-2-(3-methanesulphonyl-2-imidazolidone-1-carboxamido)-acetamido}-3-cephem-4-carboxylic acid diphenylmethyl ester are dissolved in 2 ml of CH$_2$Cl$_2$ and 0.74 ml of anisole and, in a manner analogous to that described in Example 13, treated with 9.6 ml of trifluoroacetic acid and worked up. 3-[(1-Methyl-1H-tetrazol-5-yl)-thiomethyl]-7β-{(2R)-2-[4-((2R)-2-amino-2-carboxyethoxycarbonylamino)-phenyl]-2-(3-methanesulphonylamino-2-imidazolidone-1-carboxamido)-acetamido}-3-cephem-4-carboxylic acid sodium salt is obtained. Decomposition from 189°; [α]$_D^{20}$ = +19° ± 1° (0.662% in H$_2$O). IR: 3350, 1770, 1740, 1662, 1612, 1536, 1383, 1170 cm$^{-1}$ (Nujol). UV: 244 (25200; H$_2$O).

EXAMPLE 20

In a manner analogous to that described in Example 13, 0.9 g of 3-[(1-methyl-1H-tetrazol-5-yl)-thiomethyl]-7β-{(2S)-2-[4-((2R)-2-BOC-amino-2-diphenyl-methoxycarbonylethoxycarbonylamino)-phenyl]-2-(3-methanesulphonyl-2-imidazolidone-1-carboxamido)-acetamido}-3-cephem-4-carboxylic acid diphenylmethyl ester are treated in 1.5 ml of CH$_2$Cl$_2$ and 0.56 ml of anisole with 7.2 ml of trifluoroacetic acid and worked up. 3-[(1-methyl-1H-tetrazol-5-yl)-thiomethyl]-7β-{(2S)-2-[4-((2R)-2-amino-2-carboxyethoxycarbonylamino)-phenyl]-2-(3-methanesulphonyl-2-imidazolidone-1-carboxamido)-acetamido}-3-cephem-4-carboxylic acid sodium salt is obtained. Decomposition from 184°; [α]$_D^{20}$ = +59° ± 1° (0.735% in H$_2$O); IR: 3360, 1770, 1738, 1674, 1613, 1535, 1397, 1382, 1363, 1170 cm$^{-1}$ (Nujol). UV: 243 (25700; H$_2$O).

EXAMPLE 21

10 g of (R,S)-2-(4-BOC-aminophenyl)-2-(4-ethyl-2,3-dioxopiperazine-1-carboxamido)-acetic acid and 9.07 g of 3-[(1-methyl-1H-tetrazol-5-yl)-thiomethyl]-7β-amino-3-cephem-4-carboxylic acid diphenylmethyl ester are reacted in the manner described in Example 10 (2.46 ml of chloroformic acid isobutyl ester; 2.64 ml of N-methylmorpholine and 243 ml of tetrahydrofuran) and worked up analogously to that Example. The resulting crude product is chromatographed over 400 g of silica gel. 500 ml Fractions are taken. Fractions 1–37 are eluted with toluene/ethyl acetate (1:1), and the later fractions with ethyl acetate. Fractions 8–13 are combined and concentrated by evaporation and the evaporation residue is reprecipitated once from CH$_2$Cl$_2$/ether/hexane. 3-[(1-Methyl-1H-tetrazol-5-yl)-thiomethyl]-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester is obtained. [α]$_D^{20}$ = −95° ± 1° (0.915% in CHCl$_3$). IR: 3410, 3280, 1785, 1715, 1690, 1615, 1592, 1508 cm$^{-1}$ (CH$_2$Cl$_2$).

UV: 248 (31800; EtOH).

The following fractions 14–29 consist, according to a thin layer chromatogram (system: ethyl acetate), of a mixture of the above R-compound and the corresponding S-derivative, which can be further separated by another analogous chromatography. From the final fractions 30–44 there is obtained, after concentration by evaporation and reprecipitation once from CH$_2$Cl$_2$/ether/hexane, 3-[(1-methyl-1H-tetrazol-5-yl)-thiomethyl]-7β-[(2S)-2-(4-BOC-aminophenyl)-2-(4-ethyl-2,3-dioxopiperazine-1-carboxamido)-acetamido]-3-cephem-4-carboxylic acid diphenylmethyl ester. [α]$_D^{20}$ = −116° ± 1° (0.951% in CHCl$_3$). IR: 3400, 3280, 1783, 1712, 1687, 1608, 1590, 1507 cm$^{-1}$ (CH$_2$Cl$_2$); UV: 248 (32400; EtOH).

EXAMPLE 22

In the manner described in Example 11, 3.40 g of 3-[(1-methyl-1H-tetrazol-5-yl)-thiomethyl]-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester are reacted with 1.38 g of p-toluenesulphonic acid monohydrate in 30 ml of acetonitrile and worked up. 3-[(1-Methyl-1H-tetrazol-5-yl)-thiomethyl]-7β-[(2R)-2-(4-aminophenyl)-2-(4-ethyl-2,3-dioxopiperazine-1-carboxamido)-acetamido]-3-cephem-4-carboxylic acid diphenylmethyl ester p-toluenesulphonate is obtained. $[\alpha]_D^{20} = -32° \pm 1°$ (0.96% in DMSO).

IR: 3450, 3320, 2625, 1785, 1718, 1683, 1515 cm$^{-1}$ (Nujol). UV: 248 (20700; EtOH).

EXAMPLE 23

In the manner described in Example 11, 1.58 g of 3-[(1-methyl-1H-tetrazol-5-yl)-thiomethyl]-7β-[(2S)-2-(4-N-BOC-aminophenyl)-2-(4-ethyl-2,3-dioxopiperazine-1-carboxamido)-acetamido]-3-cephem-4-carboxylic acid diphenylmethyl ester are reacted with 0.70 g of p-toluenesulphonic acid monohydrate in 15 ml of acetonitrile and worked up. 3-[(1-Methyl-1H-tetrazol-5-yl)-thiomethyl]-7β-[(2S)-2-(4-aminophenyl)-2-(4-ethyl-2,3-dioxopiperazine-1-carboxamido)-acetamido]-3-cephem-4-carboxylic acid diphenylmethyl ester p-toluenesulphonate is obtained. IR: 3450, 3315, 2620, 1782, 1715, 1685, 1515 cm$^{-1}$ (Nujol). UV: 247 (21000; EtOH).

EXAMPLE 24

In the manner described in Example 12, 3.2 g of 3-[(1-methyl-1H-tetrazol-5-yl)-thiomethyl]-7β-[(2R)-2-(4-aminophenyl)-2-(4-ethyl-2,3-dioxopiperazine-1-carboxamido)-acetamido]-3-cephem-4-carboxylic acid diphenylmethyl ester p-toluenesulphonate are reacted with 2.65 g of (2R)-2-BOC-amino-2-diphenylmethoxycarbonylethoxycarbonyl chloride and 0.67 ml of pyridine in 65 ml of tetrahydrofuran and worked up. The resulting crude product is chromatographed over 400 g of silica gel, and 500 ml fractions are taken. The fractions are eluted with toluene/ethyl acetate (1:1). By repreciptitating fractions 7-28 from CH$_2$Cl$_2$/ether/hexane, 3-[(1-methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained. $[\alpha]_D^{20} = -69° \pm 1°$ (1.00% in CDCl$_3$).

IR: 3400, 3300, 1785, 1715 (wide), 1690 (shoulder), 1615, 1598, 1510 cm$^{-1}$ (CH$_2$Cl$_2$). UV: 246 (33300; EtOH).

EXAMPLE 25

In the manner described in Example 12, 1.61 g of 3-[(1-methyl-1H-tetrazol-5-yl)-thiomethyl]-7β-[(2S)-2-(4-aminophenyl)-2-(4-ethyl-2,3-dioxopiperazine-1-carboxamido)-acetamido]-3-cephem-4-carboxylic acid diphenylmethyl ester p-toluenesulphonate are reacted with 1.33 g of (2R)-2-BOC-amino-2-diphenylmethoxycarbonylethoxycarbonyl chloride and 0.34 ml of pyridine in 40 ml of tetrahydrofuran and worked up. The resulting crude product is chromatographed over 250 g of silica gel and 250 ml fractions are taken. The fractions are eluted with toluene/ethyl acetate (1:1). By reprecipitating fractions 16-37 from CH$_2$Cl$_2$/ether/hexane, 3-[(1-methyl-1H-tetrazol-5-yl)-thiomethyl]-7β-{(2S)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained. IR: 3405, 3302, 1782, 1715 (wide), 1690 (shoulder), 1610, 1595, 1510 cm$^{-1}$ (CH$_2$Cl$_2$).

UV: 247 (33000; EtOH).

EXAMPLE 26

1.5 g of 3-[(1-methyl-1H-tetrazol-5-yl)-thiomethyl]-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester are dissolved in 4.05 ml of CH$_2$Cl$_2$ and 1.455 ml of anisole and, in the manner described in Example 13, treated with 19.25 ml of CF$_3$COOH and worked up. 3-[(1-Methyl-1H-tetrazol-5-yl)-thiomethyl]-7β-[(2R)-2-(4-aminophenyl)-2-(4-ethyl-2,3-dioxopiperazine-1-carboxamido)-acetamido]-3-cephem-4-carboxylic acid sodium salt is obtained. Decomposition from 200° C. $[\alpha]_D^{20} = -6° \pm 1°$ (1.072% in H$_2$O). IR: 3350, 1770, 1712, 1680, 1610, 1520 cm$^{-1}$ (Nujol). UV: 245 (22000; H$_2$O).

EXAMPLE 27

1.5 g of 3-[(1-methyl-1H-tetrazol-5-yl)-thiomethyl]-7β-[(2S)-2-(4-BOC-aminophenyl)-2-(4-ethyl-2,3-dioxopiperazine-1-carboxamido)-acetamido]-3-cephem-4-carboxylic acid diphenylmethyl ester are dissolved in 4.05 ml of CH$_2$Cl$_2$ and 1.455 ml of anisole and, in the manner described in Example 13, reacted with 19.25 ml of CF$_3$COOH and worked up. 3-[(1-Methyl-1H-tetrazol-5-yl)-thiomethyl]-7β-[(2S)-2-(4-aminophenyl)-2-(4-ethyl-2,3-dioxopiperazine-1-carboxamido)-acetamido]-3-cephem-4-carboxylic acid sodium salt is obtained. Decomposition from 205°; $[\alpha]_D^{20} = +32° \pm 1°$ (0.910% in H$_2$O).

IR: 3380, 1770, 1715, 1680, 1612, 1518 cm$^{-1}$ (Nujol). UV: 244 (20800; H$_2$O).

EXAMPLE 28

1.5 g of 3-[(1-methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are dissolved in 2.5 ml of CH$_2$Cl$_2$ and 0.925 ml of anisole and, in the manner described in Example 13, reacted with 12 ml of trifluoroacetic acid and worked up. 3-[(1-Methyl-1H-tetrazol-5-yl)-thiomethyl]-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. Decomposition from 195°; $[\alpha]_D^{20} = +7° \pm 1°$ (0.964% in H$_2$O);

IR: 3440 (shoulder), 3300, 1770, 1720, 1682, 1615, 1520 (wide) cm$^{-1}$ (Nujol). UV: 244 (29700; EtOH).

EXAMPLE 29

0.58 g of 3-[(1-methyl-1H-tetrazol-5-yl)-thiomethyl]-7β-{(2S)-2-[4-((2R)-2-BOC-amino-2-diphenylmethoxyethoxycarbonylamino)-phenyl]-2-(4-ethyl-2,3-dioxopiperazine-1-carboxamido)-acetamido}-3-cephem-4-carboxylic acid diphenylmethyl ester are dissolved in 1 ml of CH$_2$Cl$_2$ and 0.2 ml of anisole and, in the manner described in Example 13, reacted with 5 ml of trifluoroacetic acid and worked up. 3-[(1-Methyl-1H-tetrazol-5-yl)-thiomethyl]-7β-{(2S)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. Decomposition from 195°; $[\alpha]_D^{20} = +35° \pm 1°$ (0.995% in H$_2$O);

IR: 3440 (shoulder), 3300, 1770, 1715, 1678, 1610, 1515 (wide) cm$^{-1}$ (Nujol). UV: 244 (30000; H$_2$O).

EXAMPLE 30

10 ml of acetone are added to a solution of 0.61 g of 3-[(1-methyl-1H-tetrazol-5-yl)-thiomethyl]-7β-[(2R)-2-(4-aminophenyl)-2-(2-imidazolidone-1-carboxamido)-acetamido]-3-cephem-4-carboxylic acid sodium salt in 10 ml of water and then, while stirring, a solution of 0.43 g of (2R)-2-BOC-amino-2-diphenylmethoxycarbonylethoxycarbonyl chloride in 10 ml of acetone is added dropwise at room temperature in the course of 40 minutes, the pH value of the reaction solution being maintained constant at 7.5 by the addition of 1N aqueous sodium hydroxide solution. After the dropwise addition, the reaction mixture is stirred for 10 minutes under the same conditions, extracted with ethyl acetate, and then washed twice with water. The combined aqueous washings are concentrated in vacuo to a volume of approximately 10 ml. The product is precipitated by adding 200 ml of ethanol, filtered with suction, washed twice with ethanol and twice with ether and dried in vacuo at 50° to constant weight. 3-[(1-Methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid sodium salt is obtained. UV: 248 nm (26000; H$_2$O).

EXAMPLE 31

2.3 g of 3-[(1-methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid sodium salt are made into a slurry at room temperature in a mixture of 3.75 ml of CH$_2$Cl$_2$ and 1.35 ml of anisole, 17.7 ml of trifluoroacetic acid cooled to 0° are added, and the mixture is stirred for 15 minutes without external cooling (slurry turns into solution). Precipitation and working up are then carried out in the manner described in Example 13. 3-[(1-Methyl-1H-tetrazol-5-yl)-thiomethyl]-7β-{(2R)-2-[4-((2R)-2-amino-2-carboxyethoxycarbonylamino)-phenyl]-2-(2-imidazolidone-1-carboxamido)-acetamido}-3-cephem-4-carboxylic acid sodium salt, which is identical to the preparation described in Example 14, is obtained.

EXAMPLE 32

0.68 g of 3-[(1-methyl-1H-tetrazol-5-yl)-thiomethyl]-7β-[(2R,S)-2-(4-aminophenyl)-2-(3-methanesulphonylamino-2-imidazolidone-1-carboxamido)-acetamido]-3-cephem-4-carboxylic acid sodium salt is reacted in the manner described in Example 30. 3-[(1--Methyl-1H-tetrazol-5-yl)-thiomethyl]-7β-{(2R,S)-2-[4-((2R)-2-BOC-amino-2-diphenylmethoxycarbonylethoxycarbonylamino)-phenyl]-2-(3-methanesulphonyl-2-imidazolidone-1-carboxamido)-acetamido}-3-cephem-4-carboxylic acid sodium salt is obtained. UV: 247 (25500; H$_2$O).

EXAMPLE 33

2.3 g of 3-[(1-methyl-1H-tetrazol-5-yl)-thiomethyl]-7β-{(2R,S)-2-[4-((2R)-2-BOC-amino-2-diphenylmethoxycarbonylethoxycarbonylamino)-phenyl]-2-(3-methanesulphonyl-2-imidazolidone-1-carboxamido)-acetamido}-3-cephem-4-carboxylic acid sodium salt are reacted in the manner described in Example 31. 3-[(1-Methyl-1H-tetrazol-5-yl)-thiomethyl]-7β-{(2R,S)-2-[4-((2R)-2-amino-2-carboxyethoxycarbonylamino)-phenyl]-2-(3-methanesulphonyl-2-imidazolidone-1-carboxamido)-acetamido}-3-cephem-4-carboxylic acid sodium salt is obtained. IR: 3355, 1770, 1739, 1668, 1612, 1536, 1383, 1363, 1170 cm$^{-1}$ (Nujol). UV: 244 (25400; H$_2$O).

EXAMPLE 34

0.66 g of 3-[(1-methyl-1H-tetrazol-5yl)-thiomethyl]-7β-[(2R)-2-(4-aminophenyl)-2-(4-ethyl-2,3-dioxopiperazine-1-carboxamido)-acetamido]-3-cephem-4-carboxylic acid sodium salt is reacted in the manner described in Example 30. 3-[(1-Methyl-1H-tetrazol-5-yl)-thiomethyl]-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid sodium salt is obtained.

UV: 249 (26500; H$_2$O).

EXAMPLE 35

2.25 g of 3-[(1-methyl-1H-tetrazol-5-yl)thiomethyl]-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid sodium salt are reacted in the manner described in Example 31. 3-[(1-Methyl-1H-tetrazol-5-yl)-thiomethyl]-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt, which is identical to the preparation obtained according to Example 28, is obtained.

EXAMPLE 36

0.66 g of 3-[(1-methyl-1H-tetrazol-5-yl)-thiomethyl]-7β-{(2S)-2-[4-aminophenyl]-2-(4-ethyl-2,3-dioxopiperazine-1-carboxamido)-acetamido}-3-cephem-4-carboxylic acid sodium salt is reacted in the manner described in Example 30. 3-[(1-Methyl-1H-tetrazol-5-yl)-thiomethyl]-7β-{(2S)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid sodium salt is obtained.

UV: 249 (26500; H$_2$O).

EXAMPLE 37

2.20 g of 3-[(1-methyl-1H-tetrazol-5yl)-thiomethyl]-7β-{(2S)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid sodium salt are reacted in the manner described in Example 31. 3-[(1-Methyl-1H-tetrazol-5-yl)-thiomethyl]-7β-{(2S)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt, which is identical to the preparation obtained according to Example 29, is obtained.

EXAMPLE 38

A solution of 434.5 g of di-tert.-butyl dicarbonate in 250 ml of dioxan is added to a solution of 120 g of p-aminomethylacetophenone ethylene ketal in 1 liter of dioxan/water (1:1). The reaction mixture is stirred for 2 hours at room temperature, the pH being kept constant at 8.5 by the continuous addition of 2N NaOH (titrator). The reaction mixture is then taken up in ethyl acetate, washed neutral with aqueous NaCl solution, dried and concentrated by evaporation. The resulting crude product is chromatographed over 400 g of silica gel and, by crystallising the toluene eluates from hexane, N-BOC-p-aminomethylacetophenone ethylene ketal is obtained. Melting point 105°–107° C. IR: 3450, 1710, 1500 cm$^{-1}$ ($CH_2Cl_2$).

EXAMPLE 39

125 g of N-BOC-p-aminomethylacetophenone ethylene ketal are heated for 15 minutes at 65° in 250 ml of methanol and 250 ml of acetic acid as well as 50 ml of water. The reaction mixture is cooled to 0°, adjusted to a pH of 10 with 10N aqueous NaOH, extracted with ethyl acetate and washed neutral with saturated aqueous NaCl solution. The crude product obtained after drying and concentrating by evaporation is crystallised from hexane. N-BOC-p-aminomethylacetophenone having a melting point of 73°–75° is obtained. IR: 3420, 1707, 1680, 1607, 1500 cm$^{-1}$ ($CH_2Cl_2$). UV: 250 nm (15700) in $C_2H_5OH$.

EXAMPLE 40

106 g of N-BOC-p-aminomethylacetophenone and 79.7 g of $SeO_2$ are stirred in 520 ml of pyridine for 15 hours at 80° C. under nitrogen. The mixture is cooled, precipitated selenium is filtered off and washed with acetone, the filtrate is evaporated to dryness in vacuo, and the residue is taken up in 500 ml of toluene and evaporated to dryness in vacuo again. The residue is then suspended in 300 ml of methanol and 500 ml of water, adjusted to a pH of 3 with 2N hydrochloric acid, extracted with ethyl acetate and washed neutral with saturated aqueous NaCl solution, and the organic phase is dried and concentrated by evaporation in vacuo. The resulting crude product is crystallised from a mixture of 100 ml of ethyl acetate, 300 ml of ether and 200 ml of hexane, yielding N-BOC-p-aminomethylphenylglyoxylic acid having a melting point of 176°–178° (decomposition).

EXAMPLE 41

34.1 g of sodium acetate.$3H_2O$ and 17.7 g of hydroxylamine hydrochloride are triturated in a mortar into a slurry. The free hydroxylamine is leached out of the slurry with 400 ml of ethanol. The solution is freed of solid material by filtration and boiled under reflux for 2 hours together with 41.8 g of N-BOC-p-aminomethylphenylglyoxylic acid. The mixture is evaporated to dryness in vacuo, taken up in ethyl acetate and extracted twice with 150 ml of saturated aqueous $NaHCO_3$ solution each time. The combined bicarbonate solutions are cooled to 0°, adjusted to a pH of 2 with 2N hydrochloric acid and extracted with ethyl acetate. After washing neutral the ethyl acetate phase with saturated NaCl solution, drying and concentrating by evaporation, N-BOC-p-aminomethylphenylglyoxylic acid oxime (syn+anti) is obtained (melting point 253°, decomposition), which is further processed without purification.

EXAMPLE 42

31.8 g of N-BOC-p-aminomethylphenylglyoxylic acid oxime (syn+anti) are made into a slurry with 1 liter of water, and brought into solution by adding the calculated amount of 2N sodium hydroxide solution, a pH of 7 being reached when the addition of the latter solution is complete. The resulting solution is hydrogenated in the presence of 2 g of 10% Pd/C catalyst until the absorption of hydrogen is complete. The hydrogenation solution is filtered off from the catalyst which is washed with water, the filtrate is concentrated in vacuo to approximately 500 ml and adjusted to a pH of 4.5 with 2N hydrochloric acid, and the resulting product is filtered off. The filter residue is washed with a little ice-water and repeatedly with hexane and is dried in vacuo at 70°. N-BOC-p-aminomethyl-(R,S)-phenylglycine having a melting point of 248° (decomposition) is obtained.

EXAMPLE 43

(2R,S)-2-[4-(N-BOC-aminomethyl)-phenyl]-2-(4-ethyl-2,3-dioxopiperazine-1-carboxamido)-acetic acid is produced analogously to the manner described in Example 9 from 18 g of N-BOC-p-aminomethyl-(R,S)-phenylglycine and 28.9 g of 1-chlorocarbonyl-2,3-dioxo-4-ethylpiperazine.

EXAMPLE 44

In the manner described in Example 21, 16 g of (2R,S)-2-(4-N-BOC-aminomethylphenyl)-2-(4-ethyl-2,3-dioxopiperazine-1-carboxamido)-acetic acid and 14.1 g of 7β-amino-3-[(1-methyl-1H-tetrazol-5-yl)-thiomethyl]-3-cephem-4-carboxylic acid diphenylmethyl ester are reacted and worked up. 7β-[(2R)-2-(4-N-BOC-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester is obtained. $[\alpha]_D^{20} = -84° \pm 1°$ (0.794% in $CHCl_3$).

IR: 3480, 1800, 1720 (wide), 1620, 1505 cm$^{-1}$ ($CH_2Cl_2$).

UV: 262 nm (12550) in $C_2H_5OH$.

7β-[(2S)-2-(4-N-BOC-Aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester is obtained as a second product. $[\alpha]_D^{20} = -85° \pm 1°$ (0.947% in $CHCl_3$).

IR: 3420, 1795, 1720, 1700, 1620, 1515 cm$^{-1}$ ($CH_2Cl_2$).

UV: 258 nm (12220) in $C_2H_5OH$.

EXAMPLE 45

In the manner described in Example 22, 3.3 g of 7β-[2-((2R)-4-N-BOC-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester are reacted with 1.3 g of p-toluenesulphonic acid monohydrate and worked up. 7β-[(2R)-2-(4-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester p-toluenesulphonate is obtained. $[\alpha]_D^{20} = -34° \pm 1°$ (0.903% in $CH_3OH$). IR: 3500–2500 (wide), 1790, 1722, 1685, 1515 cm$^{-1}$ (Nujol). UV: 255 nm (11200) in $C_2H_5OH$.

EXAMPLE 46

In the manner described in Example 23, 3.8 g of 7β-[(2S)-2-(4-N-BOC-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester are reacted with 1.5 g of p-toluenesulphonic acid monohydrate and worked up. 7β-[(2S)-2-(4-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester p-toluenesulphonate is obtained. $[\alpha]_D^{20} = -10° \pm 1°$ (1.046% in $CH_3OH$).

IR: 3500–2500 wide, 1790, 1718, 1685, 1517 cm$^{-1}$ (Nujol).
UV: 260 nm (11400) in $C_2H_5OH$.

EXAMPLE 47

In the manner described in Example 24, 3.45 g of 7β-[(2R)-2-(4-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester p-toluenesulphonate are reacted with (2R)-2-BOC-amino-2-diphenylmethoxycarbonylethoxycarbonyl chloride and worked up. 7β-{(2R)-2-[4-((2R)-2-BOC-Amino-2-diphenylmethoxycarbonylethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid diphenylmethyl ester is obtained. $[\alpha]_D = -61° \pm 1°$ (0.85% in $CHCl_3$).

IR: 3400, 3370, 1785, 1710, 1690 (shoulder), 1500 cm$^{-1}$ ($CH_2Cl_2$). UV: 256 nm (13600) in $C_2H_5OH$.

EXAMPLE 48

3.9 g of 7β-[(2S)-2-(4-aminomethylphenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid diphenylmethyl ester p-toluenesulphonate are reacted in the manner described in Example 25. 7β-{(2S)-2-[4-((2R)-2-BOC-Amino-2-diphenylmethoxycarbonylethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid diphenylmethyl ester is obtained. $[\alpha]_D^{20} = -40° \pm 1°$ (0.975% in $CHCl_3$). IR: 3400, 3250, 1785, 1710, 1695 (shoulder), 1610, 1500 cm$^{-1}$ ($CH_2Cl_2$).
UV: 258 nm (13100) in $C_2H_5OH$.

EXAMPLE 49

1.0 g of 7β-{(2R)-2-[4-((2R)-2-BOC-amino-2-diphenylmethoxycarbonylethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid diphenylmethyl ester is reacted in the manner described in Example 28. 7β-{(-2R)-2-[4-((2R)-Amino-2-carboxyethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid sodium salt is obtained. $[\alpha]_D^{20} = +6° \pm 1°$ (0.805% in $H_2O$). IR: 3500–2500 (wide), 1775, 1715, 1680, 1615, 1515 cm$^{-1}$ (Nujol). UV: 245 nm (26200) in $H_2O$.

EXAMPLE 50

1.0 g of 7β-{(2S)-2-[4-((2R)-BOC-amino-2-diphenylmethoxycarbonylethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid diphenylmethyl ester is reacted in the manner described in Example 29. 7β-{(2S)-2-[4-((2R)-2-Amino-2-carboxyethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid sodium salt is obtained. $[\alpha]_D^{20} = +50° \pm 1°$ (0.817% in $H_2O$). IR: 3500–2500 wide, 1775, 1713, 1682, 1614, 1512 cm$^{-1}$ (Nujol). UV: 245 nm (26200) in $H_2O$.

EXAMPLE 51

In the manner described in Example 21, 13.7 g of (2R,S)-2-(4-BOC-aminophenyl)-2-(4-ethyl-2,3-dioxopiperazine-1-carboxamido)-acetic acid and 11.04 g of 7β-amino-3-carbamoyloxymethyl-3-cephem-4-carboxylic acid diphenylmethyl ester are reacted, worked up and chromatographed. Crystallisation from acetone/hexane yields 7β-[(2R)-2-(4-BOC-aminophenyl-2-(4-ethyl-2,3-dioxopiperazine-1-carboxamido)-acetamido]-3-carbamoyloxymethyl-3-cephem-4-carboxylic acid diphenylmethyl ester. $[\alpha]_D^{20} = 8° \pm 1°$ (0.873% in $CHCl_3$). IR: 3500, 3395, 3260, 1786, 1720, 1693, 1615, 1590, 1518 cm$^{-1}$ ($CH_2Cl_2$).
UV: 248 nm (32200) in $C_2H_5OH$.

There is obtained as a second product after recrystallisation from acetone/hexane, 7β-[(2S)-2-(4-BOC-aminophenyl)-2-(4-ethyl-2,3-dioxopiperazine-1-carboxamido)-acetamido]-3-carbamoyloxymethyl-3-cephem-4-carboxylic acid diphenylmethyl ester. $[\alpha]_D^{20} = -61° \pm 1°$ (0.823% in $CHCl_3$). IR: 3480, 3395, 3260, 1782, 1725, 1690, 1615, 1595, 1517 cm$^{-1}$ ($CH_2Cl_2$). UV: 248 nm (32600) in $C_2H_5OH$.

EXAMPLE 52

5.5 g of 7β-[(2R)-2-(4-BOC-aminophenyl)-2-(4-ethyl-2,3-dioxopiperazine-1-carboxamido)-acetamido]-3-carbamoyloxymethyl-3-cephem-4-carboxylic acid diphenylmethyl ester are reacted in 200 ml of acetonitrile with 2.44 g of p-toluenesulphonic acid monohydrate in the manner described in Example 22. 7β-[(2R)-2-(4-Aminophenyl)-2-(4-ethyl-2,3-dioxopiperazine-1-carboxamido)-acetamido]-3-carbamoyloxymethyl-3-cephem-4-carboxylic acid diphenylmethyl ester p-toluenesulphonate is obtained. $[\alpha]_D^{20} = +11° \pm 1°$ (1.098% in $CH_3OH$);

IR: 3500–2500 wide with shoulders at 3300 and 2620, 1780, 1710, 1680, 1610, 1510 cm$^{-1}$ (Nujol). UV: 250 nm (19600) in $CH_3OH$.

EXAMPLE 53

3.3 g of 7β-[(2S)-2-(4-BOC-aminophenyl)-2-(4-ethyl-2,3-dioxopiperazine-1-carboxamido)-acetamido]-3-carbamoyloxymethyl-3-cephem-4-carboxylic acid diphenylmethyl ester are reacted in 100 ml of acetonitrile with 1.46 g of p-toluenesulphonic acid monohydrate in the manner described in Example 22. 7β-[(2S)-2-(4-Aminophenyl)-2-(4-ethyl-2,3-dioxopiperazine-1-carboxamido)-acetamido]-3-carbamoyloxymethyl-3-cephem-4-carboxylic acid diphenylmethyl ester p-toluenesulphonate is obtained. $[\alpha]_D^{20} = +27° \pm 1°$ (0.954% in $CH_3OH$);

IR: 3500–2500 wide with shoulders at 3300 and 2620, 1781, 1712, 1679, 1610, 1513 cm$^{-1}$ (Nujol). UV: 250 nm (19700) in $CH_3OH$.

EXAMPLE 54

5.0 g of 7β-[(2R)-2-(4-aminophenyl)-2-(4-ethyl-2,3-dioxopiperazine-1-carboxamido)-acetamido]-3-carbamoyloxymethyl-3-cephem-4-carboxylic acid diphenylmethyl ester p-toluenesulphonate are reacted in the manner described in Example 24 with (2R)-2-BOC-amino-2-diphenylmethoxycarbonylethoxycarbonyl chloride. 7β-{(2R)-2-[4-((2R)-2-BOC-Amino-2-diphenylmethoxycarbonylethoxycarbonylamino)-phenyl]-2-(4-ethyl-2,3-dioxopiperazine-1-carboxamido)-acetamido}-3-carbamoyloxymethyl-3-cephem-4-carboxylic acid diphenylmethyl ester is obtained. $[\alpha]_D^{20} = +8° \pm 1°$ (0.895% in CHCl$_3$). IR: 3610, 3500, 3320, 1790, 1720, 1690, 1605, 1525 cm$^{-1}$ (CH$_2$Cl$_2$).

EXAMPLE 55

3.3 g of 7β-[(2S)-2-(4-aminophenyl)-2-(ethyl-2,3-dioxopiperazine-1-carboxamido)-acetamido]-3-carbamoyloxymethyl-3-cephem-4-carboxylic acid diphenylmethyl ester p-toluenesulphonate are reacted in the manner described in Example 24 with (2R)-2-BOC-amino-2-diphenylmethoxycarbonylethoxycarbonyl chloride. 7β-{(2S)-2-[4-((2R)-2-BOC-Amino-2-diphenylmethoxycarbonylethoxycarbonylamino)-phenyl]-2-(4-ethyl-2,3-dioxopiperazine-1-carboxamido)-acetamido}-3-carbamoyloxymethyl-3-cephem-4-carboxylic acid diphenylmethyl ester is obtained. $[\alpha]_D^{20} = 37° \pm 1°$ (0.865% in CHCl$_3$). IR: 3610, 3500, 3320, 1789, 1718, 1689, 1603, 1523 cm$^{-1}$ (CH$_2$Cl$_2$).

EXAMPLE 56

2.25 g of 7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-carbamoyloxymethyl-3-cephem-4-carboxylic acid diphenylmethyl ester are reacted in the manner described in Example 28. 7β-{(2R)-2-[4-((2R)-2-Amino-2-carboxyethoxycarbonylamino)-phenyl]-2-(4-ethyl-2,3-dioxopiperazine-1-carboxamido)-acetamido}-3-carbamoyloxymethyl-3-cephem-4-carboxylic acid sodium salt is obtained. Decomposition from 205°. $[\alpha]_D^{20} = +42° \pm 1°$ (1.027% in H$_2$O). IR: 3600-2500 (wide), 1772, 1686, 1619, 1520 cm$^{-1}$ (Nujol).

EXAMPLE 57

0.9 g of 7β-{(2S)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-carbamoyloxymethyl-3-cephem-4-carboxylic acid diphenyl-methyl ester is reacted in the manner described in Example 28. 7β-{(2S)-2-[4-((2R)-2-Amino-2-carboxyethoxycarbonylamino)-phenyl]-2-(4-ethyl-2,3-dioxopiperazine-1-carboxamido)-acetamido}-3-carbamoyloxymethyl-3-cephem-4-carboxylic acid sodium salt is obtained. Decomposition from approximately 240°. $[\alpha]_D^{20} = +64° \pm 1°$ (0.524% in H$_2$O). IR: 3600-2500 (wide), 1770, 1717, 1685, 1617, 1521 cm$^{-1}$ (Nujol).

EXAMPLE 58

5.2 g of 7β-[(2R)-2-(4-BOC-aminophenyl)-2-(4-ethyl-2,3-dioxopiperazine-1-carboxamido)-acetamido]-3-cephem-4-carboxylic acid diphenylmethyl ester are reacted with 2.01 g of p-toluenesulphonic acid monohydrate in 100 ml of acetonitrile in the manner described in Example 22. 7β-[(2R)-2-(4-Aminophenyl)-2-(4-ethyl-2,3-dioxopiperazine-1-carboxamido)-acetamido]-3-cephem-4-carboxylic acid diphenylmethyl ester p-toluenesulphonate is obtained. IR: 3500-2500 wide, 1779, 1712, 1681, 1609, 1510 cm$^{-1}$ (Nujol).

UV: 248 nm (21200) in C$_2$H$_5$OH.

EXAMPLE 59

4.9 g of 7β-[(2R)-2-(4-aminophenyl)-2-(4-ethyl-2,3-dioxopiperazine-1-carboxamido)-acetamido]-3-cephem-4-carboxylic acid diphenylmethyl ester p-toluenesulphonate are reacted in the manner described in Example 24. 7β-{(2R)-2-[4-((2R-2-BOC-Amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained. IR: 3400, 3310, 1787, 1714 (wide), 1691 (shoulder), 1615, 1599, 1511 cm$^{-1}$ (CH$_2$Cl$_2$). UV: 247 nm (32800) in C$_2$H$_5$OH.

EXAMPLE 60

2.09 g of 7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are reacted in the manner described in Example 28. 7β-{(2R)-2-[4-((2R)-Amino-2-carboxyethoxycarbonylamino)-phenyl]-2-(4-ethyl-2,3-dioxopiperazine-1-carboxamido)-acetamido}-3-cephem-4-carboxylic acid sodium salt is obtained.

IR: 3380, 1771, 1716, 1681, 1613, 1519 cm$^{-1}$ (Nujol). UV: 244 nm (19800) in H$_2$O.

EXAMPLE 61

In the manner described in Example 10, 15 g of (R,S)-2-(4-BOC-aminophenyl)-2-(4-ethyl-2,3-dioxopiperazine-1-carboxamido)-acetic acid and 12.1 g of 3-acetoxymethyl-7β-amino-3-cephem-4-carboxylic acid diphenylmethyl ester are reacted (3.7 ml of chloroformic acid isobutyl ester, 3.96 ml of N-methylmorpholine, 300 ml of tetrahydrofuran) and worked up. The resulting crude product is chromatographed over 900 g of silica gel (1 liter fractions). Fractions 1-12 are eluted with toluene/ethyl acetate (7:3), fractions 13-18 with toluene/ethyl acetate (3:2), fractions 19-43 with toluene/ethyl acetate (1:1) and the later fractions with ethyl acetate. Fractions 23-27 are combined and concentrated by evaporation and the evaporation residue is reprecipitated once from CH$_2$Cl$_2$/ether/hexane. 3-Acetoxymethyl-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester is obtained. $[\alpha]_D^{20} = +8° \pm 1°$ (0.92% in CHCl$_3$).

IR: 3380, 3270, 1785, 1718, 1690, 1612, 1595, 1515 cm$^{-1}$ (CH$_2$Cl$_2$). UV: 248 (31800; C$_2$H$_5$OH).

The following fractions 28-35 consist of a mixture of the above R-compound and the corresponding S-derivative, which can be further separated by further analogous chromatography. By concentrating by evaporation the final fractions 36-48 and reprecipitating once from CH$_2$Cl$_2$/ether/hexane, 3-acetoxymethyl-7β-[(2S)-2-(4-BOC-aminophenyl)-2-(4-ethyl-2,3-dioxopiperazine-1-carboxamido)-acetamido]-3-cephem-4-carboxylic acid diphenylmethyl ester is obtained. $[\alpha]_D^{20} = +22° \pm 1°$ (0.65% in CHCl$_3$), IR: 3380, 3270, 1785, 1720, 1692, 1615, 1600, 1515 cm$^{-1}$ (CH$_2$Cl$_2$). UV: 248 (32600; C$_2$H$_5$OH).

EXAMPLE 62

In the manner described in Example 11, 4.815 g of 3-acetoxymethyl-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester are reacted with 2.2 g of p-toluenesulphonic acid monohydrate in 40 ml of acetonitrile and worked up. 3-Acetoxymethyl-7β-[(2R)-2-(4-aminophenyl)-2-(4-ethyl-2,3-dioxopiperazine-1-carboxamido)-acetamido]-3-cephem-4-carboxylic acid diphenylmethyl ester p-toluenesulphonate is obtained. $[\alpha]_D^{20} = +15° \pm 1°$ (0.94% in $CH_3OH$).

IR: 3480 (shoulder), 3330, 2690, 1790, 1725, 1703, 1691, 1621, 1519 cm$^{-1}$ (Nujol). UV: 250 (22000; $C_2H_5OH$).

EXAMPLE 63

In the manner described in Example 11, 3.883 g of 3-acetoxymethyl-7β-[(2S)-2-(4-BOC-aminophenyl)-2-(4-ethyl-2,3-dioxopiperazine-1-carboxamido)-acetamido]-3-cephem-4-carboxylic acid diphenylmethyl ester are reacted with 1.75 g of p-toluenesulphonic acid monohydrate in 30 ml of acetonitrile and worked up. 3-Acetoxymethyl-7β-[(2S)-2-(4-aminophenyl)-2-(4-ethyl-2,3-dioxopiperazine-1-carboxamido)-acetamido]-3-cephem-4-carboxylic acid diphenylmethyl ester p-toluenesulphonate is obtained. $[\alpha]_D^{20} = +32° \pm 1°$ (0.90% in $CH_3OH$).

IR: 3480 (shoulder), 3335, 2650, 1795, 1727, 1685, 1622, 1518 cm$^{-1}$ (Nujol). UV: 250 (22000; $C_2H_5OH$).

EXAMPLE 64

In the manner described in Example 12, 4.56 g of 3-acetoxymethyl-7β-[(2R)-2-(4-aminophenyl)-2-(4-ethyl-2,3-dioxopiperazine-1-carboxamido)-acetamido]-3-cephem-4-carboxylic acid diphenylmethyl ester p-toluenesulphonate are reacted with 3.8 g of (2R)-2-BOC-amino-2-diphenylmethoxycarbonylethoxycarbonyl chloride and 0.95 ml of pyridine in 135 ml of tetrahydrofuran and worked up. Th resulting crude product is chromatographed over 400 g of silica gel (500 ml fractions), fractions 1–12 being eluted with toluene/ethyl acetate (3:2) and the later fractions with toluene/ethyl acetate (1:1). By reprecipitating fractions 9–23 from $CH_2Cl_2$/ether/hexane, 3-acetoxymethyl-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained. $[\alpha]_D^{20} = +8° \pm 1°$ (0.82% in $CHCl_3$).

IR: 3570, 3400, 1795, 1750–1700 (wide), 1620, 1607, 1510 cm$^{-1}$ ($CH_2Cl_2$). UV: 246 (32100; $C_2H_5OH$).

EXAMPLE 65

In the manner described in Example 12, 3.63 g of 3-acetoxymethyl-7β-[(2S)-2-(4-aminophenyl)-2-(4-ethyl-2,3-dioxopiperazine-1-carboxamido)-acetamido]-3-cephem-4-carboxylic acid diphenylmethyl ester p-toluenesulphonate are reacted with 3.03 g of (2R)-2-BOC-amino-2-diphenylmethoxycarbonylethoxycarbonyl chloride and 0.76 ml of pyridine in 100 ml of tetrahydrofuran and worked up. The crude product is chromatographed over 400 g of silica gel (500 ml fractions), fractions 1–12 being eluted with toluene/ethyl acetate (1:1), fractions 13–19 with toluene/ethyl acetate (2:3) and the later fractions with ethyl acetate. By reprecipitating fractions 14–25 from $CH_2Cl_2$/ether/hexane, 3-acetoxymethyl-7β-{(2S)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained. $[\alpha]_D^{20} = 19° \pm 1°$ (0.96% in $CHCl_3$), IR: 3570, 3400, 1795, 1750–1700 (wide), 1620, 1608, 1510 cm$^{-1}$ ($CH_2Cl_2$).

UV: 247 (32120; $C_2H_5OH$).

EXAMPLE 66

3.46 g of 3-acetoxymethyl-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are dissolved in 5.9 ml of $CH_2Cl_2$ and 2.15 ml of anisole and, as described in Example 13, reacted with 28.5 ml of trifluoroacetic acid and worked up. 3-Acetoxymethyl-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. Decomposition from 175°. $[\alpha]_D^{20} = +58° \pm 1°$ (0.82% in $H_2O$). IR: 3340 (wide), 1778, 1730, 1687, 1615, 1540 (wide) cm$^{-1}$ (Nujol).

UV: 243 (26250; $H_2O$).

EXAMPLE 67

2.27 g of 3-acetoxymethyl-7β-{(2S)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are dissolved in 3.88 ml of $CH_2Cl_2$ and 1.41 ml of anisole and, in the manner described in Example 13, reacted with 18.7 ml of trifluoroacetic acid and worked up. 3-Acetoxymethyl-7β-{(2S)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. Decomposition from 175°. $[\alpha]_D^{20} = +85° \pm 1°$ (0.88% in $H_2O$). IR: 3300 (wide), 1770, 1720, 1680, 1612, 1530 (wide) cm$^{-1}$ (Nujol). UV: 243 (27900; $H_2O$).

EXAMPLE 68

1.9 g of 3-acetoxymethyl-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt are stirred at 70° for 1½ hours with 0.453 g of isonicotinamide and 4.104 g of sodium iodide as well as 0.447 g of trichloroacetic acid in 2.73 ml of $H_2O$. The reaction mixture is then cooled and introduced into 380 ml of acetone. A precipitate forms which is filtered off, washed with acetone and ether and then dried in a water jet vacuum at 50°. The product is then dissolved in 100 ml of $H_2O$ and the aqueous phase is extracted with 150 ml of ion exchanger LA$_1$ (acetate form, liquid). The separated $H_2O$ phase is then extracted once with hexane and twice with ethyl acetate and is finally concentrated to 20 ml in a rotary evaporator. The product is then precipitated by adding alcohol, filtered with suction and dried. For further purification, reprecipitation is carried out again from water/alcohol. In this manner 3-(4-carbamoylpyridiniomethyl)-7β-{(2R)-2-[4-((2R)-amino-2-carboxyethoxycarbonylamino)-phenyl]-2-(4-ethyl-2,3-dioxopiperazine-1-carboxamido)-acetamido}-3-cephem-4-carboxylate is obtained. Decomposition from 170°.

IR: 3320 (wide), 1778, 1719, 1684, 1619, 1530 (wide) cm$^{-1}$ (Nujol).

UV: 241 (31800; H₂O).

EXAMPLE 69

2.3 g of 3-acetoxymethyl-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt and 1.16 g of 1-(2-dimethylaminoethyl)-5-mercapto-1H-tetrazole are dissolved in 12 ml of twice-distilled and degassed water. The solution is then adjusted to a pH of 6.2 with 1N aqueous NaOH and then stirred at 65° for 4 hours under a nitrogen atmosphere. It is then cooled, adjusted to a pH of 5 with 1N HCl and introduced into 600 ml of ethanol. The resulting precipitate is filtered with suction, washed with alcohol and ether and dried. The crude product is then separated over a column of 100 g of silylated silica gel (Opty-Up C 12; ANTEC AG, CH-4431 Bennwil) and 40 ml fractions are taken. Fractions 1-13 are eluted with H₂O/acetonitrile (97:3), fractions 14-20 with H₂O/acetonitrile (93:7), fractions 21-28 with H₂O/acetonitrile (9:1) and the later fractions with H₂O/acetonitrile (4:1). By concentrating by evaporation and reprecipitating from H₂O/ethanol fractions 33-35, 3-[1-(2-dimethylaminoethyl)-1H-tetrazol-5-ylthiomethyl]-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid is obtained. Decomposition from 165°. $[\alpha]_D^{20} = +34°\pm 1°$ (0.67% in H₂O). IR: 3400 (shoulder), 3280 (wide), 1770, 1720, 1680, 1612, 1515 cm⁻¹ (Nujol).

UV: 244 (30800; H₂O).

EXAMPLE 70

In the manner described in Example 69, 2 g of 3-acetoxymethyl-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt and 0.93 g of 1-carboxymethyl-5-mercapto-1H-tetrazole are reacted in 10 ml of twice-distilled degassed water, worked up and purified by chromatography. By contrast with Example 69, fractions 1-14 are eluted with H₂O and the later fractions are eluted with H₂O/acetonitrile (97:3).

By concentrating fractions 12-18 by evaporation, dissolving the evaporation residue in 10 ml of water and lyophilising, 3-(1-carboxymethyl-1H-tetrazol-5-ylthiomethyl)-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid disodium salt is obtained. Decomposition from 180°.

UV: 244 (30400; H₂O). NMR: inter alia 1.30 (t, J=7, NCH₂CH₃); 5.23 (d, J=5, H-C(6)); 5.50 (s, N(H₂COONa); 5.75 (s, ArCHCONH); 5.92 (d, J=S, H-C(7)); 7.58 (s, 4 arom. H) (CDOOD).

EXAMPLE 71

3.3 g of 3-acetoxymethyl-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are cooled to −75° in 330 ml of absolute tetrahydrofuran. Dry nitrogen is then passed through the solution for 30 minutes while stirring. A solution of 0.081 g of lithium in 15 ml of absolute methanol, which has been pre-cooled to −75°, is then added dropwise at the same temperature in the course of 1 minute, while stirring, in a nitrogen atmosphere, the mixture is stirred for 2 minutes and 0.2 ml of tert.-butyl hypochlorite is added. The reaction mixture is then stirred at −75° for 33 minutes and after 3 and 18 minutes 0.2 and 0.1 ml, respectively, of tert.-butyl hypochlorite are added. There are then added dropwise, in succession, 3.5 ml of glacial acetic acid and 1.5 g of sodium thiosulphate in 2 ml of water and the mixture is slowly warmed to room temperature. It is then concentrated in vacuo to approximately 20 ml, taken up in ethyl acetate, washed with aqueous solutions of NaHCO₃ and NaCl, dried over Na₂SO₄ and concentrated by evaporation. The resulting crude product is chromatographed over 400 g of silica gel (500 ml fractions). Fractions 1-12 are eluted with toluene/ethyl acetate (3:2), and the later fractions with toluene/ethyl acetate (1:1). By reprecipitating fractions 21-36 from CH₂Cl₂/ether/hexane, 3-acetoxymethyl-7α-methoxy-7β-{(2R)-2-[4-((2R)-2-BOC-amino-2-diphenylmethoxycarbonylethoxycarbonylamino)-phenyl}-2-(4-ethyl-2,3-dioxopiperazine-1-carboxamido)-acetamido}-3-cephem-4-carboxylic acid diphenylmethyl ester is obtained. IR: 3380, 3250, 1780, 1740 (shoulder), 1715, 1695 (shoulder), 1610, 1595, 1495 cm⁻¹ (CH₂Cl₂).

EXAMPLE 72

2.0 g of 3-acetoxymethyl-7α-methoxy-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are dissolved in 5 ml of CH₂Cl₂ and 1.3 ml of anisole and, in the manner described in Example 13, reacted with 17 ml of trifluoroacetic acid and worked up. 3-Acetoxymethyl-7α-methoxy-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. Decomposition from 185°. $[\alpha]_D^{20}=+62°\pm 1°$ (0.69% in H₂O). IR: 3320 (wide), 1772, 1730, 1688, 1620, 1520 (wide) cm⁻¹ (Nujol). UV: 241 (23300; H₂O).

EXAMPLE 73

0.8 g of 3-acetoxymethyl-7α-methoxy-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt and 0.286 g of 1-methyl-5-mercapto-1H-tetrazole sodium salt are dissolved in 4 ml of twice-distilled and degassed water. The pH is then adjusted to 6.2 with 1N hydrochloric acid. Then, in the manner described in Example 69, the solution is reacted (reaction duration 5 hours), worked up and chromatographed. By contrast with Example 69, 20 ml fractions are eluted with H₂O/acetonitrile (95:5). By concentrating by evaporation and reprecipitating from H₂O/ethanol fractions 8-20, 3-[(1-methyl-1H-tetrazol-5-yl)-thiomethyl]-7α-methoxy-7β-}(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. Decomposition from 195°. $[\alpha]_D^{20}=+31°\pm 1°$ (0.69% in H₂O). IR: 3450 (shoulder), 3320 (wide), 1775, 1717, 1685, 1618, 1517 cm⁻¹ (Nujol).

UV: 242 (25900; H₂O).

EXAMPLE 74

4.6 g of 3-acetoxymethyl-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester are methoxylated in 450 ml of tetrahydrofuran in the manner described in Example 71 (0.16 g of lithium in 30 ml of methanol, 0.9 ml of tert.-butyl hypochlorite divided into two portions of 0.35 ml and a third portion of 0.2 ml). The resulting crude product is chromatographed over 400 g of silica gel (500 ml fractions). Fractions 1–12 are eluted with toluene/ethyl acetate (3:2) and the later fractions with toluene/ethyl acetate (1:1). By crystallising fractions 13–18 from $CH_2Cl_2$/ether, 3-acetoxymethyl-7α-methoxy-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester is obtained. Decomposition at 162°. $[\alpha]_D^{20} = +34° \pm 1°$ (1.00% in $C_2H_5OH$). IR: 3370, 3250, 1780, 1717, 1690, 1612, 1597, 1500 $cm^{-1}$ ($CH_2Cl_2$). UV: 245 (29300; $CH_3OH$).

EXAMPLE 75

2.7 g of 3-acetoxymethyl-7α-methoxy-7β-[(2R)-2-(4-BOC-aminophenyl)-2-(4-ethyl-2,3-dioxopiperazine-1-carboxamido)-acetamido]-3-cephem-4-carboxylic acid diphenylmethyl ester are dissolved in 4.9 ml of $CH_2Cl_2$ and 1.7 ml of anisole and, in the manner described in Example 13, reacted with 20 ml of trifluoroacetic acid and worked up. 3-Acetoxymethyl-7α-methoxy-7β-[(2R)-2-(4-aminophenyl)-2-(4-ethyl-2,3-dioxopiperazine-1-carboxamido)-acetamido]-3-cephem-4-carboxylic acid sodium salt is obtained. Decomposition from 195°. IR: 3400 (wide), 1773, 1718, 1690, 1618, 1515 $cm^{-1}$ (Nujol). UV: 239 (16800; $H_2O$).

EXAMPLE 76

1.0 g of 3-acetoxymethyl-7α-methoxy-7β-[(2R)-2-(4-aminophenyl)-2-(4-ethyl-2,3-dioxopiperazine-1-carboxamido)-acetamido]-3-cephem-4-carboxylic acid sodium salt is dissolved in 25 ml of acetonitrile/water (1:1) and cooled to 0°. In the course of 30 minutes a solution of 0.77 g of (2R)-2-BOC-amino-2-diphenylmethoxycarbonylethoxycarbonyl chloride in 10 ml of acetonitrile is then added dropwise at 0° while stirring, the pH of the reaction solution being maintained constant at 7 by the continuous addition of 0.1N NaOH (titrator). Stirring is then carried out for 30 minutes under the same conditions. The reaction solution is then adjusted to a pH of 3 with 2N hydrochloric acid, extracted with ethyl acetate, washed neutral with aqueous NaCl solution, dried over $Na_2SO_4$ and concentrated by evaporation in vacuo. The resulting crude product is dissolved in 15 ml of methanol and cooled to 0°. A solution of 1 g of diphenyldiazomethane in 15 ml of $CH_2Cl_2$ is then added dropwise (approximately 15 minutes) while stirring, and stirring is then continued for 3 hours at room temperature. To decompose the excess diphenyldiazomethane, acetic acid is added to the reaction mixture, which is taken up in ethyl acetate, washed with aqueous solutions of $NaHCO_3$ and NaCl (until neutral), dried over $Na_2SO_4$ and concentrated by evaporation. The crude product is chromatographed over 200 g of silica gel on a stepped column (25 ml fractions). Fractions 1–70 are eluted with toluene/ethyl acetate (4:1) and the later fractions with toluene/ethyl acetate (1:1). 3-Acetoxymethyl-7α-methoxy-7β-{(2R)-2-[4-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained from fractions 160–220 and, in direct comparison (IR, NMR, thin layer chromatography) with the material described in Example 71, proves to be identical.

EXAMPLE 77

In the manner described in Example 10, 9.2 g of (2R,S)-2-(4-BOC-aminophenyl)-2-(2-imidazolidone-1-carboxamido)-acetic acid and 9.7 g of 3-acetoxymethyl-7β-amino-3-cephem-4-carboxylic acid diphenylmethyl ester are reacted (3.0 ml of chloroformic acid isobutyl ester; 3.1 ml of N-methylmorpholine, 250 ml of tetrahydrofuran) and worked up. The resulting crude product is reprecipitated from ethyl acetate/ether. 3-Acetoxymethyl-7β-[(2R,S)-(4-BOC-aminophenyl)-2-(2-imidazolidone-1-carboxamido)-acetamido]-3-cephem-4-carboxylic acid diphenylmethyl ester is obtained.

IR: 3340, 3300, 1790, 1725, 1704, 1692, 1670, 1620, 1600, 1515 $cm^{-1}$ ($CH_2Cl_2$). UV: 246 (29100; $C_2H_5OH$).

EXAMPLE 78

In the manner described in Example 11, 15.2 g of 3-acetoxymethyl-7β-[(2R,S)-(4-BOC-aminophenyl)-2-(2-imidazolidone-1-carboxamido)-acetamido]-3-cephem-4-carboxylic acid diphenylmethyl ester are reacted with 7.2 g of p-toluenesulphonic acid monohydrate in 250 ml of acetonitrile and worked up. 3-Acetoxymethyl-7β-[(2R,S)-2-(4-aminophenyl)-2-(2-imidazolidone-1-carboxamido)-acetamido]-3-cephem-4-carboxylic acid diphenylmethyl ester p-toluenesulphonate is obtained.

IR: 3410, 3330, 2640, 1785, 1728, 1665, 1540 $cm^{-1}$ (Nujol). UV: 250 (16600; $C_2H_5OH$).

EXAMPLE 79

15 g of 3-Acetoxymethyl-7β-[(2R,S)-2-(4-aminophenyl)-2-(2-imidazolidone-1-carboxamido)-acetamido]-3-cephem-4-carboxylic acid diphenylmethyl ester p-toluenesulphonate are stirred in 200 ml of tetrahydrofuran together with 2.02 ml of pyridine and 9.9 g of (2R)-2-BOC-amino-2-diphenylmethoxycarbonylethoxycarbonyl chloride for 1 hour at 0°, and worked up in the manner described in Example 12. The crude product is chromatographed over 400 g of silica-gel, 500 ml fractions being taken. Fractions 1–12 are eluted with toluene/ethyl acetate (2:1) and all the later fractions with toluene/ethyl acetate (1:1). By reprecipitating fractions 19–22 from $CH_2Cl_2$/diethyl ether/hexane, 3-acetoxymethyl-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester is obtained. IR: 3400, 3270, 1785, 1725, 1700 (shoulder), 1770, 1600, 1520 $cm^{-1}$ ($CH_2Cl_2$).

UV: 245 (31240; $C_2H_5OH$).

Fractions 23–27 consist of a binary mixture of the above compound with the corresponding 2S-derivative.

By reprecipitating fractions 28–36 from $CH_2Cl_2$/diethylether/hexane, 3-acetoxymethyl-7β-{(2S)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester is obtained. IR: 3400, 3275, 1790, 1725, 1700 (shoulder), 1772, 1605, 1525 $cm^{-1}$ (Nujol). UV: 244 (31000; $C_2H_5OH$).

EXAMPLE 80

1.92 g of 3-acetoxymethyl-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester are methoxylated in 190 ml of tetrahydrofuran in the manner described in Example 71 (0.049 g of lithium in 8 ml of methanol, 0.34 ml of tert.-butyl hypochlorite divided into two portions of 0.12 ml and a third portion of 0.1 ml). The resulting crude product is chromatographed over 200 g of silica gel in a stepped column (20 ml fractions). Fractions 1-110 are eluted with toluene/ethyl acetate (4:1) and all the later fractions with toluene/ethyl acetate (1:1). By reprecipitating fractions 251-340 from $CH_2Cl_2$/diethyl ether/hexane, 3-acetoxymethyl-7α-methoxy-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester is obtained. IR: 3400, 3280, 1781, 1725 (wide) with shoulders at 1695 and 1685, 1610 (shoulder), 1600, 1505 (wide) $cm^{-1}$ ($CH_2Cl_2$). UV: 246 (27900; $C_2H_5OH$).

EXAMPLE 81

2.2 g of 3-acetoxymethyl-7β-{(2S)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester are methoxylated in 220 ml of tetrahydrofuran in the manner described in Example 71 (0.057 g of lithium in 10 ml of methanol, 0.36 ml of tert.-butyl hypochlorite divided into 2 portions each of 0.13 ml and a third portion of 0.1 ml). The resulting crude product is chromatographed over 350 g of silica gel (500 ml fractions). Fractions 1-12 are eluted with toluene/ethyl acetate (3:2), fractions 13-36 with toluene/ethyl acetate (1:1) and all later fractions with toluene/ethyl acetate (1:2). By reprecipitating fractions 13-44 from $CH_2Cl_2$/diethyl ether/hexane, 3-acetoxymethyl-7α-methoxy-7β-{(2S)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester is obtained. $[\alpha]_D^{20} = +58° \pm 1°$ (0.842% in $C_2H_5OH$).

IR: 3400, 3275, 1780, 1722 (wide), 1695 (shoulder), 1680 (shoulder), 1610 (shoulder), 1600, 1500 (wide) $cm^{-1}$ ($CH_2Cl_2$). UV: 246 (28900; $C_2H_5OH$).

EXAMPLE 82

0.55 g of 3-acetoxymethyl-7α-methoxy-7β-{(2R)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester is dissolved in 1 ml of $CH_2Cl_2$ and 0.4 ml of anisole and, in the manner described in Example 13, reacted with 4 ml of trifluoroacetic acid and worked up. 3-Acetoxymethyl-7α-methoxy-7β-{(2R)-2-[4-((2R)-2-amino-2-carboxyethoxycarbonylamino)-phenyl]-2-(2-imidazolidone-1-carboxamido)-acetamido}-3-cephem-4-carboxylic acid sodium salt is obtained. Decomposition from 245°. $[\alpha]_D^{20} = +73° \pm 1°$ (0.848% in $H_2O$). IR: 3300 (wide), 1770, 1730, 1650, 1620, 1535 $cm^{-1}$ (Nujol).

UV: 243 (21600; $H_2O$).

EXAMPLE 83

1.4 g of 3-acetoxymethyl-7α-methoxy-7β-{(2S)-2-[4-((2R)-2-BOC-amino-2-diphenylmethoxycarbonylethoxycarbonylamino)-phenyl]-2-(2-imidazolidone-1-carboxamido)-acetamido}-3-cephem-4-carboxylic acid diphenylmethyl ester is dissolved in 3 ml of $CH_2Cl_2$ and 1 ml of anisole and, in the manner described in Example 13, reacted with 12 ml of trifluoroacetic acid and worked up. 3-Acetoxymethyl-7α-methoxy-7β-{(2S)-2-[4-((2R)-2-amino-2-carboxyethoxycarbonylamino)-phenyl]-2-(2-imidazolidone-1-carboxamido)-acetamido}-3-cephem-4-carboxylic acid sodium salt is obtained. $[\alpha]_D^{20} = +110° \pm 1°$ (0.715% in $H_2O$). IR: 3300, 1772, 1735, 1658, 1623, 1540 $cm^{-1}$ (Nujol). UV: 244 (26400; $H_2O$). Decomposition from 230°.

EXAMPLE 84

In the manner described in Example 70, 2 g of 3-acetoxymethyl-7α-methoxy-7β-{(2R)-2-[4-((2R)-2-aminocarboxyethoxycarbonylamino)-phenyl]-2-(4-ethyl-2,3-dioxopiperazine-1-carboxamido)-acetamido}-3-cephem-4-carboxylic acid sodium salt are reacted in 10 ml of water with 1 g of 1-carboxymethyl-5-mercapto-1H-tetrazole, worked up and purified by chromatography. 3-[(1-carboxymethyl-1-H-tetrazol-5-yl)-thiomethyl]-7α-methoxy-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid disodium salt is obtained. IR: 3430 (shoulder), 3300, 1770, 1721, 1680, 1615, 1515 (wide) $cm^{-1}$ (Nujol).

UV: 244 (29700; $H_2O$).

EXAMPLE 85

In the manner described in Example 69, 2.3 g of 3-acetoxymethyl-7α-methoxy-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt are reacted in 10 ml of water with 1.1 g of 1-dimethylaminoethyl-5-mercapto-1H-tetrazole, worked up and chromatographed. 3-[(1-Dimethylaminoethyl-1H-tetrazol-5-yl)-thiomethyl]-7α-methoxy-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. IR: 3440 (shoulder), 3300, 1768, 1720, 1682, 1617, 1520 (wide) $cm^{-1}$ (Nujol).

UV: 244 (30000; $C_2H_5$ OH).

EXAMPLE 86

A solution of 5 g of HCOONa in 6 ml of HCOOH, preheated to 80°, is added at 80° to a solution of 10 g of 3-aminoacetophenone in 10 ml of HCOOH. After allowing to cool slowly, the mixture is left overnight at room temperature then, at 0°, 44.5 ml of acetic anhydride are added and the mixture is stirred for 4 hours at 0°. 14.4 ml of $H_2O$ are then added dropwise and concentration by evaporation in vacuo is carried out. The product is taken up in ethyl acetate, washed in succession with saturated aqueous solutions of $NaHCO_3$ and NaCl, dried over $Na_2SO_4$ and concentrated by evaporation in vacuo. N-Formyl-3-aminoacetophenone is obtained, which is further processed without purification. M.p. 96°-7°. IR: 3370, 3300 (shoulder), 2870, 1700, 1680, 1590 $cm^{-1}$ ($CH_2Cl_2$).

EXAMPLE 87

A solution of 33.8 g of N-formyl-3-aminoacetophenone in 680 ml of THF is added dropwise in the course of 2 hours to a boiling solution of 33.8 g of LiAlH$_4$ in 1360 ml of THF and the mixture is then boiled under reflux overnight. It is then cooled to 0°, the hydride excess is decomposed by the careful addition of saturated aqueous (NH$_4$)$_2$SO$_4$ solution, the mixture is filtered through Celite, washed with CH$_2$Cl$_2$ and the filtrate is concentrated by evaporation in vacuo. m-(N-Methylamino)-1-phenylethanol is obtained, which is further processed in crude form.

EXAMPLE 88

34.8 g of m-(N-methylamino)-1-phenylethanol are reacted in 600 ml of dioxan/water (1:1) at a pH of 10 (pH held constant by the addition of 2N NaOH by means of a titrator) with 52.5 g of (BOC)$_2$O (room temperature, 16 hours). The reaction mixture is then taken up in ethyl acetate, washed neutral with saturated aqueous NaCl solution, dried over Na$_2$SO$_4$ and concentrated by evaporation in vacuo. The resulting crude product is chromatographed over 1.6 g of silica gel. From the toluene/ethyl acetate (4:1) fractions m-(N-BOC-M-methylamino)-1-phenylethanol is obtained, which is further processed directly. IR: 3620, 3550, 3400, 1700 (shoulder), 1685, 1605, 1595 (shoulder) cm$^{-1}$ (CH$_2$Cl$_2$).

EXAMPLE 89

47.6 g of m-(4-BOC-N-methylamino)-1-phenylethanol are oxidised at 0° in 240 ml of acetone for 5 minutes with 52.7 ml of 8N CrO$_3$ in 8N aqueous H$_2$SO$_4$. The CrO$_3$ excess is then decomposed with methanol, the mixture is taken up in ethyl acetate, washed with saturated aqueous solutions of NaHCO$_3$ and NaCl, dried and concentrated by evaporation in vacuo. The resulting crude product is chromatographed over 750 g of silica gel. With toluene/ethyl acetate (3:2), N-BOC-3-methylaminoacetophenone is obtained. IR: 1705 (shoulder), 1680, 1600 (shoulder) 1585 cm$^{-1}$ (CH$_2$Cl$_2$).

EXAMPLE 90

In the manner described in Example 78, 10 g of 3-aminoacetophenone are reacted with 48.4 g of (BOC)$_2$O, worked up and chromatographed. N-BOC-3-aminoacetophenone is obtained. IR: 3420, 1705, 1680, 1600, 1586 cm$^{-1}$ (CH$_2$Cl$_2$).

EXAMPLE 91

45.7 g of N-BOC-3-methylaminoacetophenone are stirred for 17 hours at 80° with 34 g of SeO$_2$. The precipitated Se is filtered off, the filtrate is concentrated by evaporation in vacuo, dissolved in 100 ml of methanol, 100 ml of water are added and the pH is adjusted to 2 with 2N HCl. The mixture is then extracted with ethyl acetate, washed neutral with saturated NaCl solution, dried over Na$_2$SO$_4$ and concentrated by evaporation in vacuo. Crystallisation from ethyl acetate/methanol yields 2-(3-BOC-methylaminophenyl)-glyoxylic acid. M.p. 115° (decomposition).
IR: 3350, 3300–2300 (wide), 1700 (shoulder), 1685, 1600, 1583 cm$^{-1}$ (CH$_2$Cl$_2$).

EXAMPLE 92

In the manner described in Example 91, 15.2 g of N-BOC-3-aminoacetophenone are reacted with 12.3 g of SeO$_2$ and worked up. 2-(3-BOC-Aminophenyl)-glyoxylic acid is obtained. IR: 3350–2300 (wide), 1700, 1685, 1605, 1580 cm$^{-1}$ (CH$_2$Cl$_2$).

EXAMPLE 93

32.2 g of 2-(3-BOC-methylaminophenyl)-glyoxylic acid are reacted with 13.8 g of hydroxylamine hydrochloride in the manner described in Example 4. Crystallisation from CH$_2$Cl$_2$/CH$_3$OH/ether/hexane yields 2-(3-BOC-methylaminophenyl)-2-hydroxyiminoacetic acid. M.p. 135° (decomposition). IR: 3620, 3600–2300 (wide), 1688, 1600, 1590 (shoulder) cm$^{-1}$ (CH$_2$Cl$_2$).

EXAMPLE 94

11.7 g of 2-(3-BOC-aminophenyl)-glyoxylic acid are reacted with 5 g of hydroxylamine hydrochloride in the manner described in Example 4. 2-(3-BOC-Aminophenyl)-2-hydroxyiminoacetic acid is obtained.
IR: 3610, 3550–2306 (wide), 1690, 1605, 1595 cm$^{-1}$ (CH$_2$Cl$_2$).

EXAMPLE 95

25.4 g of 2-(3-BOC-methylaminophenyl)-2-hydroxyiminoacetic acid are suspended in 300 ml of water and brought into solution by the addition of 2N NaOH (pH 7). The solution is then exhaustively hydrogenated in the presence of 8.6 g of 10% Pd/C catalyst. The catalyst is then filtered off, the filtrate is adjusted to a pH of 4 with 2N HCl, concentrated in vacuo and precipitated by the addition of isopropanol. (R,S)-2-(3-BOC-Methylaminophenyl)-glycine is obtained, which is further processed without purification. M.p. 135° (decomposition). IR: 3330–2200, 1705, 1622, 1597, 1536 cm$^{-1}$ (Nujol).

EXAMPLE 96

3.9 g of 2-(3-BOC-aminophenyl)-2-hydroxyiminoacetic acid are converted in 150 ml of H$_2$O into the sodium salt and exhaustively hydrogenated (2 g of 10% Pd/C catalyst) in the manner described in Example 95. (R,S)-2-(3-BOC-Aminophenyl)-glycine is obtained.
IR: 3365, 3250–2200, 1700, 1620, 1595, 1535 cm$^-$(Nujol).

EXAMPLE 97

(R,S)-2-(3-BOC-Methylaminophenyl)-2-(4-ethyl-2,3-dioxopiperazine-1-carboxamido)-acetic acid is produced in a manner analogous to that in Example 7 from 18.8 g (R,S)-2-(3-BOC-methylaminophenyl)-glycine and 31.3 g of 2,3-dioxo-4-ethylpiperazine-1-carbonyl chloride.

EXAMPLE 98

(R,S)-2-(3-BOC-Aminophenyl)-2-(4-ethyl-2,3-dioxopiperazine-1-carboxamido)-acetic acid is produced in a manner analogous to that in Example 7 from 2.64 g of (R,S)-2-(3-BOC-aminophenyl)-glycine and 4.46 g of 2,3-dioxo-4-ethylpiperazine-1-carbonyl chloride.

EXAMPLE 99

In the manner described in Example 10, 6.1 g of (R,S)-2-(3-BOC-methylaminophenyl)-2-(4-ethyl-2,3-dioxopiperazine-1-carboxamido)-acetic acid and 6.0 g of 3-[(1-methyl-1H-tetrazol-5-yl)-thiomethyl]-7β-amino-3-cephem-4-carboxylic acid diphenylmethyl ester are reacted, worked up and chromatographed. Fractions 1–26 are eluted with toluene/ethyl acetate (1:1) and the later fractions with ethyl acetate (500 ml each). Fractions 16–32 are combined and concentrated by evaporation in vacuo and the evaporation residue is reprecipitated once from CH$_2$Cl$_2$/ether/hexane. 3-[(1-Methyl-1H-tetrazol-5-yl)-thiomethyl]-7β-[(2R,S)-2-(3-BOC-methylaminophenyl)-2-(4-ethyl-2,3-dioxopiperazine-1-carboxamido)-acetamido]-3-cephem-4-carboxylic acid diphenylmethyl ester is obtained. [α]$_D^{20}$ = 85°±1° (0.9% in CHCl$_3$). IR: 3360, 3250, 1785, 1705, 1685, 1602 cm$^{-1}$ (CH$_2$Cl$_2$).

EXAMPLE 100

In the manner described in Example 99, 3.05 g of (R,S)-2-(3-BOC-aminophenyl)-2-(4-ethyl-2,3-dioxopiperazine-1-carboxamido)-acetic acid and 3 g of 3-[(1-methyl-1H-tetrazol-5-yl)-thiomethyl]-7β-amino-3-cephem-4-carboxylic acid diphenylmethyl ester are reacted, worked up and chromatographed. By reprecipitating the corresponding eluates, 3-[(1-methyl-1H-tetrazol-5-yl)-thiomethyl]-7β-[(2R,S)-2-(3-BOC-aminophenyl)-2-(4-ethyl-2,3-dioxopiperazine-1-carboxamido)-acetamido]-3-cephem-4-carboxylic acid diphenylmethyl ester is obtained. IR: 3360, 3240, 1780, 1705, 1680, 1600 cm$^{-1}$ (CH$_2$Cl$_2$).

EXAMPLE 101

In the manner described in Example 11, 7.5 g of 3-[(1-methyl-1H-tetrazol-5-yl)-thiomethyl]-7β-[(2R,S)-2-(3-BOC-methylaminophenyl)-2-(4-ethyl-2,3-dioxopiperazine-1-carboxamido)-acetamido]-3-cephem-4-carboxylic acid diphenylmethyl ester are reacted with 3.1 g of p-toluenesulphonic acid monohydrate in 80 ml of acetonitrile and worked up. 3-[(1-Methyl-1H-tetrazol-5-yl)-thiomethyl]-7β-[(2R,S)-2-(3-methylaminophenyl)-2-(4-ethyl-2,3-dioxopiperazine-1-carboxamido)acetamido]-3-cephem-4-carboxylic acid diphenylmethyl ester p-toluenesulphonate is obtained. [α]$_D^{20}$ = −24°±1° (1.00% in CH$_3$OH). IR: 3450 (shoulder), 3320, 1780, 1715, 1685, 1602 cm$^{-1}$ (Nujol). UV: 252 (21000; C$_2$H$_5$OH).

EXAMPLE 102

In the manner described in Example 11, 3.75 g of 3-[(1-methyl-1H-tetrazol-5-yl)-thiomethyl]-7β-[(2R,S)-2-(3-BOC-aminophenyl)-2-(4-ethyl-2,3-dioxopiperazine-1-carboxamido)-acetamido]-3-cephem-4-carboxylic acid diphenylmethyl ester are reacted with 1.5 g of p-toluenesulphonic acid monohydrate in 37 ml of acetonitrile and worked up. 3-[(1-Methyl-1H-tetrazol-5-yl)-thiomethyl]-7β-[(2R,S)-2-(3-aminophenyl)-2-(4-ethyl-2,3-dioxopiperazine-1-carboxamido)-acetamido]-3-cephem-4-carboxylic acid diphenylmethyl ester p-toluenesulphonate is obtained. IR: 3455 (shoulder), 3320, 1785, 1715, 1690, 1600 cm$^{-1}$ (Nujol). UV: 252 (22000; C$_2$H$_5$OH).

EXAMPLE 103

In the manner described in Example 12, 7.1 g of 3-[(1-methyl-1H-tetrazol-5-yl)-thiomethyl]-7β-[(2R,S)-2-(3-methylaminophenyl)-2-(4-ethyl-2,3-dioxopiperazine-1-carboxamido)-acetamido]-3-cephem-4-carboxylic acid diphenylmethyl ester p-toluenesulphonate are reacted with 5.4 g of (2R)-2-BOC-amino-2-diphenylmethoxycarbonylethoxycarbonyl chloride and 1.16 ml of pyridine in 150 ml of tetrahydrofuran and worked up. The resulting crude product is chromatographed over 600 g of silica gel, 500 ml fractions being taken. The fractions are eluted with toluene/ethyl acetate (1:1). By reprecipitating fractions 19–33 from CH$_2$Cl$_2$/ether/hexane, 3-[(1-methyl-1H-tetrazol-5-yl)-thiomethyl]-7β-{(2R,S)-2-[3-((2R)-2-BOC-amino-2-diphenylmethoxycarbonylethoxycarbonylmethylamino)-phenyl]-2-(4-ethyl-2,3-dioxopiperazine-1-carboxamido)-acetamido}-3-cephem-4-carboxylic acid diphenylmethyl ester is obtained. [α]$_D^{20}$ = −49°±1° (0.88% in CHCl$_3$). IR: 3370, 3250, 1782, 1720–1680 (wide), 1065 cm$^{-1}$ (CH$_2$Cl$_2$).

EXAMPLE 104

In the manner described in Examples 12 and 103, 7 g of 3-[(1-methyl-1H-tetrazol-5-yl)-thiomethyl]-7β-[(2R,S)-2-(3-aminophenyl)-2-(4-ethyl-2,3-dioxopiperazine-1-carboxamido)-acetamido]-3-cephem-4-carboxylic acid diphenylmethyl ester p-toluenesulphonate are reacted with 5.4 g of (2R)-2-BOC-amino-2-diphenylmethoxycarbonylethoxycarbonyl chloride, worked up, chromatographed and precipitated. 3-[(1-Methyl-1H-tetrazol-5-yl)-thiomethyl]-7β-{(2R,S)-2-[3-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester is obtained. IR: 3375, 3225, 1784, 1720–1680 (wide), 1605 cm$^{-1}$ (CH$_2$Cl$_2$).

EXAMPLE 105

5.88 g of 3-[(1-methyl-1H-tetrazol-5-yl)-thiomethyl]-7β-{(2R,S)-2-[3-((2R)-2-BOC-amino-2-diphenylmethoxycarbonylethoxycarbonylmethylamino)-phenyl]-2-(4-ethyl-2,3-dioxopiperazine-1-carboxamido)-acetamido}-3-cephem-4-carboxylic acid diphenylmethyl ester are dissolved in 9.3 ml of CH$_2$Cl$_2$ and 3.4 ml of anisole and, in the manner described in Example 13, reacted with 44.5 ml of CF$_3$COOH and worked up. 3-[(1-Methyl-1H-tetrazol-5-yl)-thiomethyl]-7β-{(2R,S)-2-[3-((2R)-2-amino-2-carboxyethoxycarbonylmethylamino)-phenyl]-2-(4-ethyl-2,3-dioxopiperazine-1-carboxamido)-acetamido}-3-cephem-4-carboxylic acid sodium salt is obtained. [α]$_D^{20}$ = +18°±1° (0.86% in H$_2$O). IR: 3320 (wide), 1770, 1720–1680 (wide), 1620 cm$^{-1}$ (Nujol).

EXAMPLE 106

2.9 g of 3-[(1-methyl-1H-tetrazol-5-yl)-thiomethyl]-7β-{(2R,S)-2-[3-((2R)-2-BOC-amino-2-diphenylmethoxycarbonylethoxycarbonylamino)-phenyl]-2-(4-ethyl-2,3-dioxopiperazine-1-carboxamido)-acetamido}-3-cephem-4-carboxylic acid diphenylmethyl ester are dissolved in 4.5 ml of CH$_2$Cl$_2$ and 1.7 ml of anisole and, in the manner described in Example 13, reacted with 22 ml of CF$_3$COOH and worked up. 3-[(1-Methyl-1H-tetrazol-5-yl)-thiomethyl]-7β-{(2R,S)-2-[3-((2R)-2-amino-2-carboxyethoxycarbonylamino)-phenyl]-2-(4-ethyl-2,3-dioxopiperazine-1-carboxamido)-acetamido}-3-cephem-4-carboxylic acid sodium salt is obtained. IR: 3310 (wide), 1772, 1720–1680 (wide), 1620 cm$^{-1}$ (Nujol).

The following compounds, preferably in the form of their sodium salts, can be produced analogously to the foregoing Examples using corresponding starting materials and intermediates:

EXAMPLE 107

7β-{(2R)-2-[4-((2R)-2-Amino-2-carboxyethoxycarbonylamino)-phenyl]-2-(2-imidazolidone-1-carboxamido)-acetamido}-3-acetoxymethyl-3-cephem-4-carboxylic acid sodium salt,
IR: 3440, 3300, 1772, 1730–1710 (wide), 1655, 1560, 1537, 1250 cm$^{-1}$ (Nujol). UV: 244 (26200) in H$_2$O.

EXAMPLE 108

7β-{(2R)-2-[4-((2R)-2-Amino-2-carboxyethoxycarbonylamino)-phenyl]-2-(2-imidazolidone-1-carboxamido)-acetamido}-3-carbamoyloxymethyl-3-cephem-4-carboxylic acid sodium salt, IR: 3450–3280 (wide), 1769, 1725, 1660, 1535 cm$^{-1}$ (Nujol). UV: 243 (21200) in $H_2O$.

EXAMPLE 109

7β-{(2R)-2-[4-((2R)-2-Amino-2-carboxyethoxycarbonylamino)-phenyl]-2-(2-imidazolidone-1-carboxamido)-acetamido}-3-(4-carbamoylpyridiniomethyl)-3-cephem-4-carboxylate, IR: 3400, 3300, 1770, 1729, 1654, 1560, 1535 cm$^{-1}$ (Nujol). UV: 244 (21000) in $H_2O$.

EXAMPLE 110

7β-{(2R)-2-[4-((2R)-2-Amino-2-carboxyethoxycarbonylamino)-phenyl]-2-(2-imidazolidone-1-carboxamido)-acetamido}-3-(4-methyl-1,2,4-triazol-3-ylthiomethyl)-3-cephem-4-carboxylic acid sodium salt, IR: 3445 (shoulder), 3300, 1768, 1728, 1655, 1561, 1538 cm$^{-1}$ (Nujol). UV: 244 (19800) in $H_2O$.

EXAMPLE 111

7β-{(2R)-2-[4-((2R)-2-Amino-2-carboxyethoxycarbonylamino)-phenyl]-2-(2-imidazolidone-1-carboxamido)-acetamido}-3-(1-carboxymethyl-1H-tetrazol-5-ylthiomethyl)-3-cephem-4-carboxylic acid disodium salt, IR: 3450, 3300, 1770, 1729, 1656, 1560, 1535 cm$^{-1}$ (Nujol). UV: 243 (19720) in $H_2O$.

EXAMPLE 112

7β-{(2R)-2-[4-((2R)-2-Amino-2-carboxyethoxycarbonylamino)-phenyl]-2-(2-imidazolidone-1-carboxamido)-acetamido}-3-(1-sulphomethyl-1H-tetrazol-5-ylthiomethyl)-3-cephem-4-carboxylic acid disodium salt, IR: 3455, 3305, 1775, 1730, 1660, 1560, 1538 cm$^{-1}$ (Nujol). UV: 244 (20150) in $H_2O$.

EXAMPLE 113

7β-{(2R)-2-[4-((2R)-2-Amino-2-carboxyethoxycarbonylamino)-phenyl]-2-(2-imidazolidone-1-carboxamido)-acetamido}-3-(2-methyl-5,6-dioxo-1,4,5,6-tetrahydro-as-triazin-3-ylthiomethyl)-3-cephem-4-carboxylic acid disodium salt.

IR: 3470–3280 (wide), 1765, 1730, 1655, 1560, 1535 cm$^{-1}$ (Nujol) UV: 242 (24200).

EXAMPLE 114

7β-{(2R)-2-[4-((2R)-2-Amino-2-carboxyethoxycarbonylamino)-phenyl]-2-(imidazolidone-1-carboxamido)-acetamido}-3-(4-methyl-5,6-dioxo-1,4,5,6-tetrahydro-as-triazin-3-ylthiomethyl)-3-cephem-4-carboxylic acid disodium salt, IR: 3460–3290 (wide), 1766, 1732, 1657, 1561, 1537 cm$^{-1}$ (Nujol). UV: 242 (22900) in $H_2O$.

EXAMPLE 115

7β-{(2R)-2-[4-((2R)-2-Amino-2-carboxyethoxycarbonylamino)-phenyl]-2-(2-imidazolidone-1-carboxamido)-acetamido}-3-(5-methyl-1,3,4-thiadiazol-2-ylthiomethyl)-3-cephem-4-carboxylic acid sodium salt.

IR: 3445 (shoulder), 3300, 1770, 1730, 1655, 1560, 1537 cm$^{-1}$ (Nujol). UV: 244 (24700) in $H_2O$.

EXAMPLE 116

7β-{(2R)-2-[4-((2R)-2-Amino-2-carboxyethoxycarbonylamino)-phenyl]-2-(2-imidazolidone-1-carboxamido)-acetamido}-3-(3H-1,2,3-triazol-4-ylthiomethyl)-3-cephem-4-carboxylic acid sodium salt, IR: 3450 (shoulder), 3310, 1771, 1732, 1657, 1561, 1537 cm$^{-1}$. UV: 244 (23300).

EXAMPLE 117

7β-{(2R)-2-[4-((2R)-2-Amino-2-carboxyethoxycarbonylamino)-phenyl]-2-(2-imidazolidone-1-carboxamido)-acetamido}-3-[1-(2-dimethylaminoethyl)-1H-tetrazol-5-ylthiomethyl]-3-cephem-4-carboxylic acid sodium salt, IR: 3450–3290 (wide), 1770, 1730, 1655, 1560, 1535 cm$^{-1}$. UV: 242 (20900) in $H_2O$.

EXAMPLE 118

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-acetoxymethyl-3-cephem-4-carboxylic acid sodium salt, IR: 3350, 1770, 1740–1720 (wide), 1662, 1612, 1536, 1383, 1250, 1170 cm$^{-1}$ (Nujol). UV: 244 (26000) in $H_2O$.

EXAMPLE 119

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-carbamoyloxymethyl-3-cephem-4-carboxylic acid sodium salt, IR: 3350–3300 (wide), 1768, 1738, 1661, 1611, 1535, 1383, 1170 cm$^{-1}$ (Nujol). UV: 243 (24900) in $H_2O$.

EXAMPLE 120

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(4-carbamoylpyridiniomethyl)-3-cephem-4-carboxylate, IR: 3350–3290 (wide), 1769, 1740, 1660, 1612, 1534, 1383, 1170 cm$^{-1}$ (Nujol). UV: 244 (21110) in $H_2O$.

EXAMPLE 121

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(4-methyl-1,2,4-triazol-3-ylthiomethyl)-3-cephem-4-carboxylic acid sodium salt, IR: 3350, 1771, 1742, 1663, 1613, 1538, 1385, 1174 cm$^{-1}$ (Nujol). UV: 244 (25900) in $H_2O$.

EXAMPLE 122

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(5-methyl-1,3,4-thiadiazol-2-ylthiomethyl)-3-cephem-4-carboxylic acid sodium salt, IR: 3349, 1769, 1739, 1660, 1610, 1534, 1381, 1169 cm$^{-1}$ (Nujol). UV: 244 (25700) in $H_2O$.

EXAMPLE 123

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(3H-1,2,3-triazol-4-ylthiomethyl)-3-cephem-4-carboxylic acid sodium salt, IR: 3350, 1770, 1741, 1661, 1611, 1536, 1383, 1171 cm$^{-1}$ (Nujol). UV: 244 (25600) in H$_2$O.

EXAMPLE 124

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-[1-(2-dimethylaminoethyl)-1H-tetrazol-5-ylthiomethyl]-3-cephem-4-carboxylic acid sodium salt, IR: 3340 (wide), 1771, 1739, 1660, 1610, 1536, 1382, 1170 cm$^{-1}$ (Nujol). UV: 244 (23200) in H$_2$O.

EXAMPLE 125

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(1-carboxymethyl-1H-tetrazol-5-ylthiomethyl)-3-cephemcarboxylic acid disodium salt, IR: 3350 (wide), 1770, 1741, 1663, 1613, 1537, 1385, 1172 cm$^{-1}$ (Nujol). UV: 243 (22900) in H$_2$O.

EXAMPLE 126

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(1-sulphomethyl-1H-tetrazol-5-ylthiomethyl)-3-cephem-4-carboxylic acid disodium salt.

IR: 3350, 1770, 1740, 1662, 1610, 1535, 1382, 1170 cm$^{-1}$ (Nujol). UV: 244 (24400) in H$_2$O.

EXAMPLE 127

7β-{(2R)-2-[4-((2R)-2-Amino-2-carboxyethoxycarbonylamino)-phenyl]-2-(3-methanesulphonyl-2-imidazolidone-1-carboxamido)-acetamido}-3-(2-methyl-5,6-dioxo-1,4,5,6-tetrahydro-as-triazin-3-ylthiomethyl)-3-cephem-4-carboxylic acid disodium salt, IR: 3340 (wide), 1770, 1740, 1660, 1610, 1535, 1381, 1170 cm$^{-1}$ (Nujol). UV: 244 (27200) in H$_2$O.

EXAMPLE 128

7β-{(2R)-2-[4-((2R)-2-Amino-2-carboxy-ethoxycarbonylamino)-phenyl]-2-(3-methanesulphonyl-2-imidazolidone-1-carboxamido)-acetamido}-3-(4-methyl-5,6-dioxo-1,4,5,6-tetrahydro-as-triazin-3-ylthiomethyl)-3-cephem-4-carboxylic acid disodium salt, IR: 3360 (wide), 1775, 1745, 1665, 1615, 1540, 1385, 1174 cm$^{-1}$ (Nujol). UV: 244 (26900) in H$_2$O.

EXAMPLE 129

7β-{(2R)-2-[4-((2R)-2-Amino-2-carboxyethoxycarbonylamino)-phenyl]-2-(4-ethyl-2,3-dioxopiperazine-1-carboxamido)-acetamido}-3-(4-methyl-1,2,4-triazol-3-ylthiomethyl)-3-cephem-4-carboxylic acid sodium salt, IR: 3440 (shoulder), 3300, 1770, 1720, 1682, 1615, 1520 cm$^{-1}$ (Nujol). UV: 244 (29100) in H$_2$O.

EXAMPLE 130

7β-{(2R)-2-[4-((2R)-2-Amino-2-carboxyethoxycarbonylamino)-phenyl]-2-(4-ethyl-2,3-dioxopiperazine-1-carboxamido)-acetamido}-3-(5-methyl-1,3,4-thiadiazol-2-ylthiomethyl)-3-cephem-4-carboxylic acid sodium salt, IR: 3440, 3310, 1772, 1721, 1685, 1617, 1522 cm$^{-1}$ (Nujol). UV: 244 (28900) in H$_2$O.

EXAMPLE 131

7β-{(2R)-2-[4-((2R)-2-Amino-2-carboxyethoxycarbonylamino)-phenyl]-2-(4-ethyl-2,3-dioxopiperazine-1-carboxamido)-acetamido}-3-(3H-1,2,3-triazol-4-ylthiomethyl)-3-cephem-4-carboxylic acid sodium salt, IR: 3445, 3312, 1775, 1723, 1686, 1619, 1525 cm$^{-1}$ (Nujol). UV: 244 (29500) in H$_2$O.

EXAMPLE 132

7β-{(2R)-2-[4-((2R)-2-Amino-2-carboxyethoxycarbonylamino)-phenyl]-2-(4-ethyl-2,3-dioxopiperazine-1-carboxamido)-acetamido}-3-(1-sulphomethyl-1H-tetrazol-5-ylthiomethyl)-3-cephem-4-carboxylic acid disodium salt, IR: 3450–3300 (wide), 1771, 1722, 1684, 1617, 1521 cm$^{-1}$, (Nujol). UV: 244 (26500) in H$_2$O.

EXAMPLE 133

7β-{(2R)-2-[4-((2R)-2-Amino-2-carboxyethoxycarbonylamino)-phenyl]-2-(4-ethyl-2,3-dioxopiperazine-1-carboxamido)-acetamido}-3-(2-methyl-5,6-dioxo-1,4,5,6-tetrahydro-as-triazin-3-ylthiomethyl)-3-cephem-4-carboxylic acid disodium salt, IR: 3450–3300 (wide) 1770, 1719, 1680, 1613, 1520 cm$^{-1}$ (Nujol). UV: 244 (32100) in H$_2$O.

EXAMPLE 134

7β-{(2R)-2-[4-((2R)-2-Amino-2-carboxyethoxycarbonylamino)-phenyl]-2-(4-ethyl-2,3-dioxopiperazine-1-carboxamido)-acetamido}-3-(4-methyl-5,6-dioxo-1,4,5,6-tetrahydro-as-triazin-3-ylthiomethyl)-3-cephem-4-carboxylic acid disodium salt, IR: 3450–3300 (wide) 1770, 1720, 1681, 1614, 1521 cm$^{-1}$ (Nujol). UV: 244 (31900) in H$_2$O.

EXAMPLE 135

Dry ampoules or phials each containing 0.5 g of {7β-(2R)-2-[4-((2R)-2-amino-2-carboxyethoxycarbonylamino)-phenyl]-2-(4-ethyl-2,3-dioxopiperazine-1-carylamino)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid sodium salt are produced as follows:

7β-{(2R)-2-[4-((2R)-2-amino-2-carboxyethoxycarbonylamino)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid sodium salt: 0.5 g;

mannitol: 0.05 g.

A sterile aqueous solution of 7β-{(2R)-2-[4-((2R)-2-amino-2-carboxyethoxycarbonylamino)-phenyl]-2-(4-ethyl-2,3-dioxopiperazine-1-carboxamido)acetamido}-3-[(1-methyl-1H-tetrazol-5-yl)-thiomethyl]-3-cephem-4-carboxylic acid sodium salt and of the mannitol is sealed under aseptic conditions in 5 ml ampoules or 5 ml phials and examined.

EXAMPLE 136

Dry ampoules or phials each containing 0.5 g of 7β-[(2R)-2-(4-aminophenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid sodium salt are produced as follows: Composition (for 1 ampoule or phial) 7β-[(2R)-2-(4-aminophenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid sodium salt: 0.5 g;

mannitol: 0.05 g;

A sterile aqueous solution of 7β-[(2R)-2-(4-aminophenyl)-2-(4-ethyl-2,3-dioxopiperazine-1-carboxamido)-acetamido]-3-[(1-methyl-1H-tetrazol-5-yl)-thiomethyl]-3-cephem-4-carboxylic acid sodium salt and of the mannitol is sealed under aseptic conditions in 5 ml ampoules or 5 ml phials and examined.

We claim:

1. Compounds of the formula

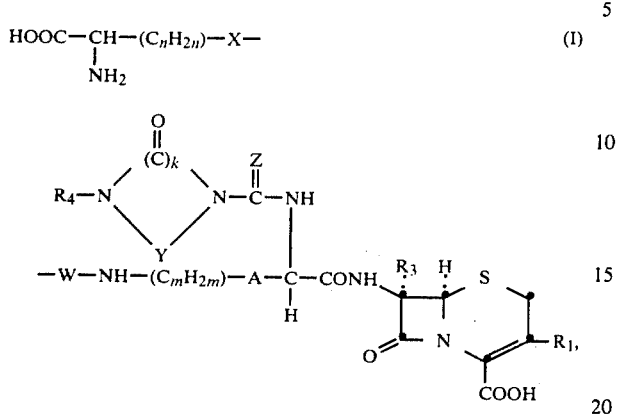

in which
n represents an integer from 1 to 4,
m represents 0 or 1,
X represents oxygen, sulphur or the —NH—group,
W represents —CO—, —CO—NHSO$_2$— or the —SO$_2$NH—CO—group, or X-W together represent —CO— or the —CO—NHSO$_2$—group,
A represents phenylene, thienylene or furylene, or such group substituted by lower alkyl, lower alkoxy and/or halogen,
Z represents oxygen or sulphur,
Y represents lower alkylene,
k represents 1 or 2,
R$_4$ represents hydrogen, lower alkyl, lower alkyl substituted by hydroxy, lower alkanoyloxy, lower alkoxycarbonyloxy, lower alkoxy, lower alkylthio, halogen, amino, di-lower alkylamino, lower alkenyl, lower alkanoyl, lower alkanoyl substituted by halogen, lower alkoxy, lower alkanoyloxy, cyano, benzoyl, benzoyl substituted by lower alkyl, hydroxy, lower alkoxy or chlorine, a pyridinecarboxylic, pyrimidinecarboxylic or pyrazinecarboxylic acid radical, a pyridinecarboxylic, pyrimidinecarboxylic or pyrazinecarboxylic acid radical substituted by hydroxy or chlorine, lower alkoxycarbonyl, benzenesulfonyl, naphthalenesulfonyl, carbamoyl, thiocarbamoyl, iminocarbamoyl (=guanyl), or sulfamoyl, or lower alkylcarbamoyl, thiocarbamoyl, iminocarbamoyl or sulfamoyl,
R$_1$ represents hydrogen, lower alkyl, lower alkoxy, halogen or a group of the formula —CH$_2$—R$_2$ in which R$_2$ is hydroxy or mercapto, lower alkanoyloxy, carbamoyloxy, lower alkylcarbamoyloxy, halogeno-lower alkylcarbamoyloxy, lower alkanoyl-lower alkylcarbamoyloxy, lower alkoxy, imidazolylthio, triazolylthio, tetrazolylthio, thiazolylthio, isothiazolylthio, thiadiazolylthio, thiatriazolylthio, oxazolylthio, isoxazolylthio, oxadiazolylthio, 1-oxidopyridylthio, pyridazinylthio, N-oxidopyridazinylthio, 2-oxo-1,2-dihydropyrimidinylthio, or 5,6-dioxotetrahydro-as-triazinylthio or imidazolylthio, triazolylthio, tetrazolylthio, thiazolylthio, isothiazolylthio, thiadiazolylthio, thiatriazolylthio, oxazolylthio, isoxazolylthio, oxadiazolylthio, 1-oxidopyridylthio, pyridazinylthio, N-oxidopyridazinylthio, 2-oxo-1,2-dihydropyrimidinylthio, or 5,6-dioxotetrahydro-as-triazinylthio substituted by lower alkyl, hydroxy-lower alkyl, lower alkanoyloxy-lower alkyl, halogeno-lower alkyl, carboxy-lower alkyl, lower alkoxycarbonyl-lower alkyl, sulpho-lower alkyl, amidated sulpho-lower alkyl, amino-lower alkyl, mono- or di-lower alkylamino lower alkyl, lower alkanoylamino lower alkyl, halogen, amino, mono- or di-lower alkylamino, lower alkanoylamino, nitro, hydroxy, lower alkoxy, carboxy, lower alkoxycarbonyl, carbamoyl, N-mono- or N,N-di-lower alkyl carbamoyl, cyano, oxo or by oxido, or R$_2$ is tri-lower alkylammonium, pyrimidinium, pyridazinium, thiazolium, quinolinium or pyridinium or pyrimidinium, pyridazinium, thiazolium, quinolinium, or pyridinium mono- or disubstituted by lower alkyl, hydroxy-lower alkyl, amino, 4-aminophenylsulfonamido, hydroxy, halogen, halogen-lower alkyl, carboxyl, lower-alkoxycarbonyl, cyano, carbamoyl, lower alkylcarbamoyl, di-lower alkylcarbamoyl, hydrazinocarbonyl, lower alkylhydrazinocarbonyl, carboxy-lower alkyl, lower alkanoyl, or 1-lower alkylpyrrolidinyl, and R$_3$ represents hydrogen, and wherein the term lower indicates the group thus defined is having one to four carbon atoms, and wherein the carboxyl groups are in the free form or are present as lower alkanoyloxymethoxycarbonyl, amino-lower alkanoylmethoxycarbonyl, phthalidyloxycarbonyl or indanyloxycarbonyl that can be split under physiological conditions, and pharmaceutically acceptable salts of such compounds.

2. Compounds of the formula I according to claim 1, in which the group —(C$_n$H$_{2n}$)— is unbranched, n, m and k are defined as in claim 1, X represents oxygen or the —NH—group, W represents —CO— or the —CO—NHSO$_2$—group, or X-W together represent —CO— or the group —CO—NHSO$_2$—, A represents p-, o- or m-phenylene, 2,5-thienylene or 2,5-furylene, Z represents oxygen or sulfur, Y represents 1,2-ethylene, R$_4$ represents hydrogen, lower alkyl, lower alkyl substituted by hydroxy, lower alkanoyloxy, lower alkoxycarbonyloxy, lower alkoxy, lower alkylthio, halogen, amino, di-lower alkylamino, lower alkenyl, lower alkoxy, lower alkanoyloxy, cyano or phenoxy, benzoyl, benzoyl substituted by lower alkyl, hydroxy, lower alkoxy or chlorine, a pyridinecarboxylic, pyrimidinecarboxylic or pyrazinecarboxylic acid radical, a pyridinecarboxylic, pyrimidinecarboxylic or pyrazinecarboxylic acid radical substituted by hydroxy or chlorine, lower alkoxycarbonyl, benzenesulfonyl, naphthalenesulfonyl, carbamoyl, thiocarbamoyl, iminocarbamoyl (=guanyl), or sulfamoyl, or lower alkylcarbamoyl, thiocarbamoyl, iminocarbamoyl or sulfamoyl, R$_1$ represents hydrogen, lower alkyl, lower alkoxy, halogen or a group of the formula —CH$_2$—R$_2$ in which R$_2$ represents lower alkanoyloxy, carbamoyloxy, lower alkylcarbamoyloxy, triazolylthio, tetrazolylthio, thiazolylthio, thiatriazolylthio, thiadiazolylthio, oxazolylthio, oxadiazolylthio, 5,6-dioxotetrahydro-as-triazinylthio or pyridinio, or triazolylthio, tetrazolylthio, thiazolylthio, thiatriazolylthio, thiadiazolylthio, oxazolylthio, oxadiazolylthio, 5,6-dioxotetrahydro-as-triazinylthio or pyridinio substituted by lower alkyl, N,N-di-lower alkylamino-lower alkyl, carboxy-lower alkyl, sulpho-lower alkyl, amino, carboxy-lower alkanoylamino or carbamoyl, and R₃ represents hydrogen, and pharmaceutically acceptable salts of such compounds.

3. Compounds of the formula I according to claim 1, in which the group —($C_nH_{2n}$)— is unbranched, n, m and k have the meanings given in claim 1, X represents oxygen or the —NH—group, W represents —CO— or the —CO—$NHSO_2$—group, or X-W together represent —CO— or the —CO—$NHSO_2$—group, A represents p-, o- or m-phenylene or, when m is 1, 2,5-thienylene or 2,5-furylene, Y represents 1,2-ethylene, Z represents oxygen, R₄ represents hydrogen; lower alkyl, lower alkyl substituted by hydroxy, lower alkanoyloxy, lower alkoxycarbonyloxy, lower alkoxy, lower alkylthio, halogen, carboxy, amino or di-lower alkylamino; lower alkenyl; lower alkanoyl, lower alkanoyl substituted by chlorine, lower alkoxy, lower alkanoyloxy, cyano or phenoxy; benzoyl, benzoyl substituted by lower alkyl, hydroxy, lower alkoxy or chlorine; a pyridine-, pyrimidine- or pyrazinecarboxylic acid radical or such group substituted by hydroxy or chlorine; lower alkoxycarbonyl; benzenesulphonyl, benzenesulphonyl substituted by chlorine or lower alkyl; or carbamoyl, thiocarbamoyl, iminocarbamoyl (=guanyl) or sulfamoyl, R₁ represents hydrogen, methyl, methoxy, chlorine or a group of the formula —$CH_2$—R₂ in which R₂ represents acetoxy; carbamoyloxy; 1-methyl-1H-tetrazol-5-ylthio, 1-sulphomethyl-1H-tetrazol-5-ylthio, 1-carboxymethyl-1H-tetrazol-5-ylthio or 1-(2-dimethylaminoethyl)-1H-tetrazol-5-ylthio; 2-methyl-1,3,4-thiadiazol-5-ylthio; 2-methyl-5,6-dioxo-1,2,5,6-tetrahydro-as-triazin-3-ylthio or 4-methyl-5,6-dioxo-1,4,5,6-tetrahydro-as-triazin-3-ylthio; or 4-carbamoylpyridinio, and R₃ represents hydrogen, and pharmaceutically acceptable salts of such compounds.

4. Pharmaceutically acceptable preparations containing compounds of the formula I according to claim 1 or pharmaceutically acceptable salts of such compounds having salt-forming groups for use in the treatment of bacterial infections.

5. Method of treating infections caused by gram-positive or gram-negative bacteria which comprises administering to a host a pharmaceutical preparation according to claim 4.

6. Compounds of the formula I according to claim 1, in which the group —($C_nH_{2n}$)— represents methylene, the indices m and k have the meanings indicated, X represents oxygen and W represents a group —CO—, A represents p- or o-phenylene, Y represents 1,2-ethylene, R₄ represents hydrogen, ethyl, or mesyl, Z represents oxygen, R₁ represents hydrogen, methyl, methoxy, chlorine or a group of the formula —$CH_2$—R₂ in which R₂ represents acetoxy; carbamoyloxy; 1-methyl-1H-tetrazol-5-ylthio, 1-sulphomethyl-1H-tetrazol-5-ylthio, 1-carboxymethyl-1H-tetrazol-5-ylthio or 1-(2-1H-tetrazol-5-ylthio; 2-methyl-1,3,4-thiadiazol-5-ylthio; 2-methyl-5,6-dioxo-1,2,5,6-tetrahydro-as-triazin-3-ylthio or 4-methyl-5,6-dioxo-1,4,5,6-tetrahydro-as-triazin-3-ylthio; or 4-carbamoylpyridinio, and R₃ represents hydrogen or methoxy, and pharmaceutically acceptable salts of such compounds.

7. 3[(1-Methyl-1H-tetrazol-5-yl)-thiomethyl]-7β{(2R)-2-[4-((2R)-2-amino-2-carboxyethoxycarbonylamino)-phenyl]-2-(2-imidazolidone-1-carboxamido)-acetamido}-3-cephem-4-carboxylic acid and pharmaceutically acceptable salts thereof according to claim 1.

8. 3-[(1-Methyl-1H-tetrazol-5-yl)-thiomethyl]-7β-{(2R)-2-[4-((2R)-2-amino-2-carboxyethoxycarbonylamino)-phenyl]-2-(3-methanesulphonylamino-2-imidazolidone-1-carboxamido)-acetamido}-3-cephem-4-carboxylic acid and pharmaceutically acceptable salts thereof according to claim 1.

9. 3-[(1-Methyl-1H-tetrazol-5-yl)-thiomethyl]-7β-{(2S)-2-[4-((2R)-2-amino-2-carboxyethoxycarbonylamino)-phenyl]-2-(3-methanesulphonyl-2-imidazolidone-1-carboxamido)-acetamido}-3-cephem-4-carboxylic acid and pharmaceutically acceptable salts thereof according to claim 1.

10. 3-[(1-Methyl-1H-tetrazol-5-yl)-thiomethyl]-7β-{(2R)-2-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid and pharmaceutically acceptable salts thereof according to claim 1.

11. 3-[(1-Methyl-1H-tetrazol-5-yl)-thiomethyl]--7β-{(2S)-[4-((2R)-2-amino-2-carboxyethoxycarbonylamino)-phenyl]-2-(4-ethyl-2,3-dioxopiperazine-1-carboxamido)-acetamido}-3-cephem-4-carboxylic acid and pharmaceutically acceptable salts thereof according to claim 1.

12. 3-[(1-Methyl-1H-tetrazol-5-yl)-thiomethyl]-7β-{(2R,S)-2-[4-((2R)-2-amino-2-carboxyethoxycarbonylamino)-phenyl]-2-(3-methanesulphonyl-2-imidazolidone-1-carboxamido)-acetamido}-3-cephem-4carboxylic acid and pharmaceutically acceptable salts thereof according to claim 1.

13. 7β-{(2R)-2-[4-((2R)-Amino-2-carboxyethyloxycarbonyl-aminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid and pharmaceutically acceptable salts thereof according to claim 1.

14. 7β-{(2S)-2-[4-((2R)-2-Amino-2-carboxyethoxycarbonylaminomethyl)-phenyl]-2-(4-ethyl-2,3-dioxopiperazine-1-carboxamido)-acetamido}-3-[(1-methyl-1H-tetrazol-5-yl)-thiomethyl]-3-cephem-4-carboxylic acid and pharmaceutically acceptable salts thereof according to claim 1.

15. 7β-{(2R)-2-[4-((2R)-2-Amino-2-carboxyethoxycarbonyl-amino)-phenyl]-2-(4-ethyl-2,3-dioxopiperazine-1-carboxamido)-acetamido}-3-carbamoyloxymethyl-3-cephem-4-carboxylic acid and pharmaceutically acceptable salts thereof according to claim 1.

16. 7β-{(2S)-2-[4-((2R)-2-Amino-carboxyethoxycarbonyl-amino)-phenyl]-2-(4-ethyl-2,3-dioxopiperazine-1-carboxamido)-acetamido}-3-carbamoyloxymethyl-3-cephem-4-carboxylic acid and pharmaceutically acceptable salts thereof according to claim 1.

17. 7β-{(2R)-2-[4-((2R)-2-Amino-carboxyethoxycarbonylamino)-phenyl]-2-(4-ethyl-2,3-dioxopiperazine-1-carboxamido)acetamido}-3-[1-(2-dimethylaminoethyl)-1H-tetrazol-5-ylthiomethyl]-3-cephem-4-carboxylic acid and pharmaceutically acceptacle salts thereof according to claim 1.

18. The sodium salts of the compounds according to claim 1.

* * * * *

UNITED STATES PATENT AND TRADEMARK OFFICE
CERTIFICATE OF CORRECTION

PATENT NO. : 4,464,366

DATED : August 7, 1984

INVENTOR(S) : Wehrli et al.

It is certified that error appears in the above-identified patent and that said Letters Patent is hereby corrected as shown below:

| | |
|---|---|
| Abstract, line 5; Col. 1, line 66; Col. 11, line 62; Col. 12, line 22; Col. 83, line 23; Col. 84, line 34; Col. 85, line 4 | Delete "n" and substitute --$\underline{n}$-- |
| Abstract, line 6; Col. 1, line 67; Col. 11, line 62; Col. 11, line 66; Col. 12, lines 22, 26, 27, 65; Col. 42, line 45; Col. 75, lines 11, 16, 25, 31; Col. 83, lines 24, 34, 39; Col. 85, lines 4, 9, 46 | Delete "m" and substitute --$\underline{m}$-- |
| Abstract, line 16; Col. 2, line 9; Col. 11, line 62; Col. 12, line 22; Col. 12, line 62; Col. 42, line 45; Col. 82, line 33; Col. 83, line 35; Col. 85, lines 6, 46 | Delete "k" and substitute --$\underline{k}$-- |
| Col. 2, line 33; Col. 3, line 46; Col. 10, line 12; Col. 11, line 66; Col. 12, lines 26, 67; Col. 24, line 21; Col. 26, lines 57, 68; Col. 28, line 47; Col. 33, lines 61, 68; Col. 35, line 35; Col. 36, line 19; Col. 41, line 57; Col. 42, line 30; Col. 48, line 36; Col. 53, lines 28, 35, 44; Col. 55, lines 1, 6, 16; Col. 57, lines 10, 14, 26, 30, 39, 62; Col. 61, lines 4, 13, 19, 28, 34, 48, 58, 67; Col. 62, lines | Delete "p" and substitute --$\underline{p}$-- |

UNITED STATES PATENT AND TRADEMARK OFFICE
CERTIFICATE OF CORRECTION

PATENT NO. : 4,464,366    Page 2 of 9

DATED : August 7, 1984

INVENTOR(S) : Wehrli, et al

It is certified that error appears in the above-identified patent and that said Letters Patent is hereby corrected as shown below:

5, 20, 61; Col. 63, lines 8,
12, 22, 39; Col. 64, lines
42, 46, 59, 63; Col. 65,
lines 6, 21; Col. 65, line
65; Col. 66, lines 1, 10;
Col. 67, lines 7, 12, 23,
28, 37, 59; Col. 79, lines
29, 33, 41; Col. 77, lines
30, 34, 45, 49, 59; Col. 78,
line 12; Col. 83, line 39;
Col. 85, lines 9, 48

| | |
|---|---|
| Col. 2, line 33, Col. 3, line 46, Col. 11, line 66, Col. 12, lines 26, 67; Col. 84, line 39; Col. 85, lines 9, 48 | Delete "o" and substitute --$\underline{o}$-- |
| Col. 6, line 4 | Delete "pyridmidinylthio" and substitute --pyrimidinylthio-- |
| Col. 6, line 54 | Insert -- - -- in --carboxy-lower -- |
| Col. 11, lines 22, 24, 25; Col. 50, lines 31, 48, 57, 68; Col. 51, line 8; Col. 52, lines 15, 21, 36, 43, 48, 51, 56, 61; Col. 54, lines 45, 55, 65; Col. 55, lines 3, 13, 51, 56; Col. 56, line 35; Col. 59, lines 59, 63; Col. 60, lines 4, 10; Col. 62, lines 20, 22, 27, 33; Col. 64, line 16; Col. 66, line 35; Col. 72, | Delete "R,S" and substitute -- $\underline{R},\underline{S}$ -- |

UNITED STATES PATENT AND TRADEMARK OFFICE
CERTIFICATE OF CORRECTION

PATENT NO. : 4,464,366  Page 3 of 9

DATED : August 7, 1984

INVENTOR(S) : Wehrli, et al

It is certified that error appears in the above-identified patent and that said Letters Patent is hereby corrected as shown below:

lines 11, 18, 26, 31, 38;
Col. 76, lines 29, 40, 45,
48, 53, 56, 61; Col. 77,
lines 3, 12, 18, 26, 32, 41,
47, 56, 68; Col. 78, lines
17, 26, 34, 44, 51; Col. 86,
line 29

| | |
|---|---|
| Col. 11, line 22; Col. 53, line 21; Col. 55, line 37; Col. 56, lines 19, 25, 60, 65; Col. 57, lines 22, 28, 59; Col. 58, lines 3, 29, 35, 63; Col. 59, line 2; Col. 60, lines 46, 50, 63; Col. 62, line 46; Col. 63, lines 4, 9, 36, 41, 67; Col. 64, lines 5, 29, 55, 60; Col. 65, lines 17, 24, 47, 52; Col. 66, lines 57, 63, 20, 25, 57, 60; Col. 68, lines 1, 28, 35; Col. 72, lines 60, 62; Col. 73, lines 28, 43; Col. 74, lines 2, 10; Col. 86, lines 10, 23, 40, 51 | Delete "S" and substitute --$\underline{S}$-- |
| Col. 11, lines 23, 25; Col. 53, lines 13, 32, 42, 46, 57, 67; Col. 54, lines 20, 28 (2 instances), 35 (2 instances); Col. 55, lines 17, 28, 37, 67 (2 instances); Col. 56, lines 7 (2 instances), 19, 26, 51, 59; Col. 57, lines 6, 12, 36, 40, 48, 63; Col. 58, lines | Delete "R" and substitute --$\underline{R}$-- |

UNITED STATES PATENT AND TRADEMARK OFFICE
CERTIFICATE OF CORRECTION

PATENT NO. : 4,464,366

DATED : August 7, 1984

INVENTOR(S) : Wehrli, et al

It is certified that error appears in the above-identified patent and that said Letters Patent is hereby corrected as shown below:

3, 13, 19, 45 (2 instances), 52, 53, 63; Col. 59, lines 2, 12, 17, 32 (2 instances), 40, 50 (2 instances); Col. 60, lines 19, 23 (2 instances), 31 (2 instances), 57 (2 instances), 50, 63; Col. 62, line 37, 57, 62; Col. 63, lines 20, 24, 26 (2 instances), 41, 52 (2 instances), 58 (2 instances), 67; Col. 64, lines 5, 21, 38, 43; Col. 65, lines 3, 7, 9 (2 instances), 22, 24, 33 (2 instances), 38 (2 instances), 47, 52, 62, 67; Col. 66, lines 8, 12 (2 instances), 21 (2 instances), 26 (2 instances), 50, 57; Col. 67, lines 4, 9, 35, 38, 46, 47; Col. 68, lines 1, 11 (2 instances), 18 (2 instances), 28, 36, 44 (2 instances), 63 (2 instances); Col. 69, lines 4 (2 instances), 25 (2 instances), 36 (2 instances), 48 (2 instances), 59 (2 instances); Col. 70, lines 20 (2 instances), 28, 29, 37 (2 instances), 46, 47, 61 (2 instances); Col. 71, lines 3, 15, 24, 31, 38, 43, 67 (2 instances); Col. 72, lines 43, 52 (2 instances), 63; Col. 73, lines 2 (2 instances), 17, 18, 28, 43, 54, 55, 61, 62; Col. 74, lines 3, 10, 20 (2 instances), 27 (2 instances), 38 (2 instances), 45 (2 instances); Col. 77, lines 60, 68; Col. 78, lines 14, 17, 26, 34,

UNITED STATES PATENT AND TRADEMARK OFFICE
CERTIFICATE OF CORRECTION

PATENT NO. : 4,464,366  
DATED : August 7, 1984  
INVENTOR(S) : Wehrli, et al

Page 5 of 9

It is certified that error appears in the above-identified patent and that said Letters Patent is hereby corrected as shown below:

44, 51, 63 (2 instances);
Col. 79, lines 2 (2 instances),
11 (2 instances), 19 (2 instances),
28 (2 instances), 37 (2 instances),
45 (2 instances), 54 (2 instances),
63 (2 instances); Col. 80, lines 2
(2 instances), 12 (2 instances), 20
(2 instances), 29, (2 instances),
38 (2 instances), 46 (2 instances),
55 (2 instances), 64 (2 instances);
Col. 81, lines 5 (2 instances), 14
(2 instances), 23 (2 instances), 32
(2 instances), 41 (2 instances), 50
(2 instances), 58 (2 instances), 67
(2 instances); Col. 82, lines 7 (2
instances), 16 (2 instances), 25 (2
instances), 35 (2 instances); 40 (2
instances), 46 (2 instances), 56, 60,
65; Col. 85, line 62 (2 instances);
Col. 86, lines 4 (2 instances), 10,
16 (2 instances), 23, 29, 34 (2 instances), 40, 46 (2 instances), 51;
56 (2 instances)

| | |
|---|---|
| Col. 29, line 37 | Delete "nbutylphosphine" and substitute -- n-butylphosphine-- |
| Col. 29, line 55 | After "dithia" insert -- - -- |
| Col. 30, line 65 | After "tris" insert -- - -- |
| Col. 33, line 59 | Delete "gem" and substitute --gem-- |
| Col. 34, line 6 | Insert -- - -- between "fluorine" and "containing" |
| Col. 34, line 28 | After "aryl" insert -- - -- |

UNITED STATES PATENT AND TRADEMARK OFFICE
CERTIFICATE OF CORRECTION

PATENT NO. : 4,464,366

DATED : August 7, 1984

INVENTOR(S) : Wehrli, et al

It is certified that error appears in the above-identified patent and that said Letters Patent is hereby corrected as shown below:

| | |
|---|---|
| Col. 46, line 58 | Delete "the" and substitute --their-- |
| Col. 49, line 42 | Delete "he" and substitute --the-- |
| Col. 53, line 56 | End of line, after "me" insert -- - -- |
| Col. 53, line 63 | Delete "1487" and substitute --1486-- |
| Col. 54, line 27 | End of line, after "thiomet" insert -- - -- |
| Col. 55, line 27 | End of line after "th" insert -- - -- |
| Col. 55, line 36 | After "3-[(1" delete "H" |
| Col. 56, line 36 | End of line after "{ " insert -- - -- |
| Col. 56, line 6 | End of line after "th" insert -- - -- |
| Co. 56, line 18 | End of line after "thi" insert -- - -- |
| Col. 58, line 2 | End of line after "(2" insert -- - -- |
| Col. 58, line 52 | End of line after "thiomethyl" insert -- - -- |
| Col. 59, line 1 | End of line after "tetra" insert -- - -- |
| Col. 59, line 39 | End of line after "thiomet" insert -- - -- |
| Col. 59, line 49 | End of line after "H" insert -- - -- |
| Col. 60, line 22 | End of line after "thiomet" insert -- - -- |
| Col. 60, line 36 | End of line after "te" insert -- - -- |

UNITED STATES PATENT AND TRADEMARK OFFICE
CERTIFICATE OF CORRECTION

PATENT NO. : 4,464,366  
DATED : August 7, 1984  
INVENTOR(S) : Wehrli, et al

Page 7 of 9

It is certified that error appears in the above-identified patent and that said Letters Patent is hereby corrected as shown below:

| | |
|---|---|
| Col. 60, line 49 | End of line after "thiomet" insert -- - -- |
| Col. 60, line 57 | End of line after "thiomethyl" insert -- - -- |
| Col. 60, line 62 | End of line after "te" insert -- - -- |
| Col. 61, line 68 | Underline "syn tanti" |
| Col. 63, line 26 | End of line insert -- - -- |
| Col. 63, line 31 | End of line underline -- 3 -- |
| Col. 63, line 41 | After "diphenylm" insert -- - -- |
| Col. 64, line 4 | End of line after "(2" insert -- - -- |
| Col. 65, line 29 | After "CHCl" delete "$_3$" and substitute -- $_3$ -- |
| Col. 67, line 41 | Delete "Th" and substitute --The-- |
| Col. 67, line 68 | After "aceto" insert -- - -- |
| Col. 69, line 47 | After "ylthi" insert -- - -- |
| Col. 69, line 54 | Delete "$CH_3$" and substitute --$CH_{\underline{3}}$-- |
| Col. 69, line 55 | Delete "ArCHCONH" and substitute --Ar$\underline{CH}$CONH-- |
| Col. 70, line 19 | End of line after "{(" insert -- - -- |
| Col. 70, line 60 | End of line after "thiomethyl" insert -- - -- |
| Col. 70, line 61 | After "7β-" delete " } " and substitute -- { -- |
| Col. 73, line 42 | End of line after "$\underline{m}$" insert -- - -- |
| Col. 74, line 20 | End of line after "3" insert -- - -- |

UNITED STATES PATENT AND TRADEMARK OFFICE
CERTIFICATE OF CORRECTION

PATENT NO. : 4,464,366                                           Page 8 of 9

DATED      : August 7, 1984

INVENTOR(S) : Wehrli, et al

It is certified that error appears in the above-identified patent and that said Letters Patent is hereby corrected as shown below:

| | |
|---|---|
| Col. 74, lines 26 and 44 | End of line after "yl" insert -- - -- |
| Col. 74, line 37 | End of line after "a" insert -- - -- |
| Col. 75, line 25 | After "BOC-" delete "M" and substitute --N-- |
| Col. 77, line 7 | Delete "0.9%" and substitute --0.96%-- |
| Col. 78, line 25 | End of line after "thi" insert -- - -- |
| Col. 79, line 45 | End of line after "carboxy-ethoxyc" insert -- - -- |
| Col. 80, lines 46, 55 | End of line insert -- - -- |
| Col. 81, lines 5, 23 | End of line insert -- - -- |
| Col. 82, lines 16, 25 | End of line insert -- - -- |
| Col. 83, line 40 | After "cyano" insert --or phenoxy-- |
| Col. 85, line 54 | After "1-(2-" insert --dimethylaminoethyl-- |
| Col. 86, line 3 | End of line after "(" insert -- - -- |
| Col. 86, line 15 | End of line after " { " insert -- - -- |

UNITED STATES PATENT AND TRADEMARK OFFICE
CERTIFICATE OF CORRECTION

PATENT NO. : 4,464,366

DATED : August 7, 1984

INVENTOR(S) : Wehrli, et al

It is certified that error appears in the above-identified patent and that said Letters Patent is hereby corrected as shown below:

Col. 86, line 32      After "4" insert -- - --

Col. 86, line 34      End of line insert -- - --

Col. 86, line 40      End of line insert -- - --

Signed and Sealed this

Seventeenth Day of September 1985

[SEAL]

Attest:

Attesting Officer

DONALD J. QUIGG

Commissioner of Patents and Trademarks—Designate